(12) United States Patent
Mishani et al.

(10) Patent No.: US 8,461,166 B2
(45) Date of Patent: Jun. 11, 2013

(54) POLYALKYLENE GLYCOL DERIVATIVES OF INHIBITORS OF EPIDERMAL GROWTH FACTOR RECEPTOR TYROSINE KINASE

(75) Inventors: Eyal Mishani, Mevasseret Zion (IL); Samar Dissoki, Jerusalem (IL); Galith Abourbeh, Jerusalem (IL); Alexander Levitzki, Jerusalem (IL)

(73) Assignees: Hadasit Medical Research Services and Development Ltd., Jerusalem (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 1742 days.

(21) Appl. No.: 11/714,760

(22) Filed: Mar. 7, 2007

(65) Prior Publication Data
US 2008/0056990 A1 Mar. 6, 2008

Related U.S. Application Data

(63) Continuation-in-part of application No. PCT/IL2006/001038, filed on Sep. 6, 2006.

(60) Provisional application No. 60/713,757, filed on Sep. 6, 2005.

(51) Int. Cl.
| | | |
|---|---|---|
| A01N 43/54 | (2006.01) | |
| A61K 31/517 | (2006.01) | |
| C07D 239/72 | (2006.01) | |

(52) U.S. Cl.
USPC .......... 514/266.1; 544/283; 544/284; 424/9.6

(58) Field of Classification Search
USPC ................. 544/283, 284; 514/266.1; 424/9.6
See application file for complete search history.

(56) References Cited

U.S. PATENT DOCUMENTS

| | | | |
|---|---|---|---|
| 5,747,498 A | 5/1998 | Schnur et al. | |
| 6,126,917 A | 10/2000 | Mishani et al. | |
| 6,127,374 A | 10/2000 | Bridges | |
| 6,153,617 A | 11/2000 | Bridges | |
| 6,251,912 B1 | 6/2001 | Wissner et al. | |
| 6,562,319 B2 | 5/2003 | Mishani et al. | |
| 2002/0128553 A1 | 9/2002 | Levitzki et al. | |
| 2004/0242604 A1 | 12/2004 | Bhattacharya et al. | |
| 2004/0265228 A1 | 12/2004 | Levitzky et al. | |
| 2005/0153371 A1 | 7/2005 | Grotzfeld et al. | |
| 2008/0096881 A1* | 4/2008 | Hennequin et al. | 514/233.8 |
| 2008/0234263 A1* | 9/2008 | Hennequin et al. | 514/234.5 |

FOREIGN PATENT DOCUMENTS

| | | | |
|---|---|---|---|
| DE | 10307165 | | 9/2004 |
| EP | 0566226 | | 11/1995 |
| WO | WO 00/51991 | | 9/2000 |
| WO | WO 03/068264 | * | 8/2003 |
| WO | WO 2004/064718 | | 8/2005 |
| WO | WO2007/029251 | | 3/2007 |

OTHER PUBLICATIONS

Smaill et al. "Tyrosine Kinase Inhibitors. 17. Irreversible Inhibitors of the Epidermal Growth Factor Receptor: 4-(Phenylamino)Quinazoline- and 4-(Phenylamino)Pyrido[3,2-D]Pyrimidine-6-Acrylamides Bearing Additional Solubilizing Functions", Journal of Medicinal Chemistry, 43: 1380-1397, 2000. Table 1, Compound 19.
Tsou et al. "6-Substituted-4-(3-Bromophenylamino)Quinazolines as Putative Irreversible Inhibitors of the Epidermal Growth Factor Receptor (EGFR) and Human Epidermal Growth Factor Receptor (HER-2) Tyrosine Kinases With Enhanced Antitumor Activity", Journal of Medicinal Chemistry, 44(17): 2719-2734, 2001.
Baselga et al. "ZD1839 ('Iressa') 1,2 as an Anticancer Agent", Drugs, 60(Suppl.1): 33-40, 2000.
Mishani et al. "Novel Carbon-11 Labeled 4-Dimethylamino-But-2-Enoic Acid [4-(Phenylamino)-Quinazoline-6-Y1]-Amides: Potential PET Bioprobes for Molecular Imaging of EGFR-Positive Tumors", Nuclear Medicine and Biology, 31(4): 469-476, 2004.
Communication Pursuant to Article 94(3) EPC Dated Oct. 15, 2010 From the European Patent Office Re.: Application No. 06780468.2.
International Search Report and the Written Opinion Dated Feb. 12, 2007 From the International Searching Authority Re. Application No. PCT/IL2006/001038.
International Preliminary Report on Patentability Dated Mar. 20, 2008 From the International Bureau of WIPO Re.: Application No. PCT/IL2006/001038.
Communication Pursuant to Article 94(3) EPC Dated Jun. 15, 2009 From the European Patent Office Re.: Application No. 06780468.2.
Artega "The Epidermal Growth Factor: From Mutant Oncogene in Nonhuman Cancers to Therapeutic Target in Human Neoplasia", Journal of Clinical Oncology, 19(18): 32s-40s, 2001.
Baselga et al. "ZD1839 ('Iressa') 1,2 as an Anticancer Agent", Drugs, 60(Suppl.1): 33-40, 2000. Ben-David et al. "Radiosynthesis of ML03, A Novel Positron Emission Tomography Biomarker for Targeting Epidermal Growth Factor Receptor Via the Labeling Synthon: [11C] Acryloyl Chloride", Applied Radiation and Isotopes, 58: 209-217, 2003.
Bonasera et al. "Potential 18F-Labeled Biomarkers for Epidermal Growth Factor Receptor Tyrosine Kinase", Nuclear Medicine and Biology, 28: 359-374, 2001.
Faaland et al. "Rapid Uptake of Tyrphostin into A431 Human Epidermoid Cells is Followed by Delayed Inhibition of Epidermal Growth Factor (EGF)-Stimulated EGF Receptor Tyrosine Kinase Activity", Molecular and Cellular Biology, 11 (5): 2697-2703, May 1991.

(Continued)

Primary Examiner — Paul V. Ward

(57) ABSTRACT

Novel epidermal growth factor receptor tyrosine kinase (EGFR-TK) inhibitors, pharmaceutical compositions including same and their use in the treatment of EGFR-TK related diseases or disorders are disclosed. Novel radiolabeled EGFR-TK inhibitors as their use as biomarkers for medicinal radioimaging such as Positron Emission Tomography (PET) and Single Photon Emission Computed Tomography (SPECT) and as radiopharmaceuticals for radiotherapy are further disclosed. The disclosed EGFR-TK inhibitors comprise a polyalkylene glycol moiety and/or a hydroxy-containing moiety and are characterized by improved solubility, biostability and bioavailability. Processes of preparing the disclosed EGFR-TK inhibitors and of radiolabeling same, via, for example, one-step radiosyntheses, are also disclosed.

37 Claims, 10 Drawing Sheets

OTHER PUBLICATIONS

Fry et al. "Specific Irreversible Inactivation of the Epidermal Growth Factor Receptor and ErbB2 by A New Tyrosine Kinase Inhibitor", Proc. Natl. Acad. Sci. USA, 95: 12022-12027, 1998.

Gazit et al. "Tyrphostins IV—Highly Potent Inhibitors of EGF Receptor Kinase. Structure—Activity Relationship Study of 4-Anilidoquinazolines", Bioorganic & Medical Chemistry, 4 (8): 1203-1207, 1996.

Han et al. "Tyrphostin AG 1478 Preferentially Inhibits Human Glioma Cells Expressing Truncated Rather Than Wild-Type Epidermal Growth Factor Receptors". Abstract.

Levitzki et al. "Tyrosin Kinase Inhibition: An Approach to Drug Development", Science, 267: 1782-1788, 1995.

Miyaji et al. "Effect of Tyrophostin on Cell Growth and Tyrosine Kinase Activity of Epidermal Growth Factor Receptor in Human Gliomas", Journal of Neurosurgery, 81: 411-419, 1994.

Nelson et al. "Cytoskeletal and Morphological Changes Associated With the Specific Suppression of the Epidermal Growth Factor Receptor Tyrosine Kinase Activity in A431 Human Epidermoid Carcinoma", Experimental Cell Research, 233: 383-390, 1997.

Paez et al. "EGFR Mutations in Lung Cancer: Correlation With Clinical Response to Gefitinib Therapy", Science, 304: 1497-1500, 2004.

Smaill et al. "Tyrosine Kinase Inhibitors. 15. 4-(Phenylamino)Quinazoline and 4-(Phenylamino)Pyrido[D]Pyrimidine Acrylamides as Irreversible Inhibitors of the ATP Binding Site of the Epidermal Growth Factor Receptor", Journal of Medicinal Chemistry, 42 (10): 1803-1815, 1999.

Smaill et al. "Tyrosine Kinase Inhibitors. 17. Irreversible Inhibitors of the Epidermal Growth Factor Receptor: 4-(Phenylamino)Quinazoline- and 4-(Phenylamino)Pyrido[3,2-D]Pyrimidine-6-Acrylamides Bearing Additional Solubilizing Functions", Journal of Medicinal C hem. 43: 1380-1397, 2000.

Tsou et al. "6-Substituted-4-(3-Bromophenylamino)Quinazolines as Putative Irreversible Inhibitors of the Epidermal Growth Factor Receptor (EGFR) and Human Epidermal Growth Factor Receptor (HER-2) Tyrosine Kinases With Enhanced Antitumor Activity", J. Med. Chem. 44: 2719-2734, 2001.

Response Dated Dec. 21, 2009 to Communication Pursuant to Article 94(3) EPC of Jun. 15, 2009 From the European Patent Office Re.: Application No. 06780468.2.

Dissoki et al. "Modified PEG-Anilinoquinazoline Derivatives as Potential EGFR PET Agents", Journal of labelled Compounds and Radiopharmaceuticals, 12 P., Oct. 29, 2008.

Response Dated Feb. 13, 2011 to Communication Pursuant to Article 94(3) EPC of Oct. 15, 2010 From the European Patent Office Re.: Application No. 06780468.2.

Pal et al. "Molecular Imaging of EGFR Kinase Activity in Tumors With 124I-Labeled Small Molecular Tracer and Positron Emission Tomography", Molecular Imaging and Biology, 8(5): 262-277, Sep. 2006.

Pal et al. "Radiosynthesis and Initial In Vitro Evaluation of [18F]-PEG6-IPQA-A Novel PET Radiotracer for Imaging EGFR Expression-Activity in Lung Carcinomas", Molecular Imaging and Biology, 13(5): 853-861, Oct. 2011.

Communication Pursuant to Article 94(3) EPC Dated Jan. 4, 2012 From the European Patent Office Re.: Application No. 06780468.2.

Communication Pursuant to Article 94(3) EPC Dated Feb. 21, 2013 From the European Patent Office Re.: Application No. 06780468.2.

* cited by examiner a: n = 2
b: n = 4
c: n = 6 a: n = 2
b: n = 4
c: n = 6 a: n = 2
b: n = 4
c: n = 6 n = 2, 4, 6

POLYALKYLENE GLYCOL DERIVATIVES OF INHIBITORS OF EPIDERMAL GROWTH FACTOR RECEPTOR TYROSINE KINASE

RELATED APPLICATIONS

This Application is a continuation-in-part of PCT International Patent Application No. PCT/IL2006/001038 filed Sep. 6, 2006, which claims the benefit of U.S. Provisional Patent Application No. 60/713,757 filed Sep. 6, 2005. The contents of the above Applications are all incorporated herein by reference.

FIELD AND BACKGROUND OF THE INVENTION

The present invention relates to novel compounds and their use in therapy (e.g. cancer therapy) and diagnosis. More particularly, the present invention relates to novel inhibitors of epidermal growth factor receptor tyrosine kinase (EGFR-TK) and their application in the treatment of EGFR-TK related diseases and disorders (e.g. cancer), and to novel radiolabeled inhibitors of EGFR-TK and their application as bioprobes for, e.g., Positron Emission Tomography (PET) and Single Photon Emission Computed Tomography (SPECT), and as radiopharmaceuticals for radiotherapy. The present invention further relates to novel processes of preparing and optionally radiolabeling the EGFR-TK inhibitors.

The presently used anticancer therapy is mostly based on non-specific cytotoxic agents, such as cisplatin, paclitaxel, doxorubicin, topotecan and 5-fluorouracil (5-FU). These cytotoxic agents are mainly directed at inducing DNA damage, inhibiting DNA synthesis or disrupting the cytoskeleton. The toxicity of these agents limits their dosage quantities, which often results in the disease recurrence. In some cases, the maximum tolerated dose is even below the minimum effective dose for tumor regression (Ciardiello, 2000; Renhowe, 2001; Rowinsky, 2000).

The realization that cancer cells differ from normal cells in their aberrant signal transduction has given impetus to cancer researchers to target the cancer cells while searching for cancer therapy and more recently for cancer diagnosis.

Polypeptides such as growth factors, differentiation factors, and hormones often mediate their pleiotropic actions by binding to and activating cell surface receptors with an intrinsic intracellular protein tyrosine kinase activity.

The Epidermal Growth Factor Receptor (EGFR/Her-1/) belongs to the ErbB receptor family involved in proliferation and differentiation of normal and malignant cells (Artega et al., 2001). Overexpression of EGFR and its enhanced signaling are a frequent hallmark of human epithelial cancers, and it contributes to the initiation, progression and/or invasiveness of human cancers (Tokunaga et al., 1995; Shimada et al., 1996; James et al. 2004; Levitzki et al., 2003). Overexpression of Epidermal Growth Factor Receptor (EGFR) is present in at least 70% of human cancers (Seymour, 2001) such as non-small cell lung carcinomas (NSCLC), breast cancers, gliomas, squamous cell carcinoma of the head and neck, and prostate cancer (Raymond et al., 2000, Salomon et al., 1995, Voldborg et al., 1997). Furthermore, correlation between EGFR overexpression and metastasis formation, therapy resistance, poor prognosis and short survival have been recently described (Tokunaga et al., 1995; Shimada et al., 1996, Rae and Lippman, 2004, and Levitzki 2003). As a result, EGFR-TK has become a major target for the development of specific anticancer drugs.

Examples of such FDA approved therapies include reversible EGFR-TK inhibitors, such as gefitinib (Iressa™, ZD1839; AstraZeneca, Wilmington, Pa.) for treatment of locally advanced or metastatic chemotherapy refractory NSCLC and erlotinib (Tarceva™; Genentech, San Francisco, Calif.) for treating locally advanced or metastatic chemotherapy refractory NSCLC and, in addition to gemcitabine, as a first choice treatment of locally advanced, inoperable or metastatic pancreatic cancer. Lapatinib (GW572016, Glaxo-Smithkline) and PKI-166 both are under phase III clinical trials.

Additional anti-EGFR targeted therapies, currently under clinical trials, include, for example, the irreversible inhibitor CI-1033.

Compounds belonging to the 4-Anilinoquinazolines family, which are also referred to herein as 4-(phenylamino) quinazolines, have also been shown to potently and selectively inhibit EGFR-TK activity by binding reversibly to an inner membrane ATP binding site on EGFR-TK, (Faaland et al., 1991; Miyaji et al., 1994; Gazit et al., 1996; Artega et al., 1997; Nelson and Fry, 1997; Johnstrom et al., 1997; Smaill et al., 1999; Tsou et al., 2001; and Han et al., 1996), the prototype for such compounds being the small molecule AG 1478, also known as PD 153035 (Fry et al., 1994; Levitzki and Gazit, 1995), which is presently in clinical development. The FDA approved Iressa described above also belongs to this quinazoline family (Baselga and Averbuch, 2000).

While the above-described agents are reversible EGFR-TK inhibitors, their potency is limited by non-specific binding and rapid blood clearance. Thus, irreversible EGFR-TK inhibitors, which are based on the structure of AG 1478, have been proposed (Fry et al., 1998; Smaill et al., 2000; and U.S. Pat. Nos. 6,153,617 and 6,127,374). PD168393 and PD160678 are representative examples of such irreversible inhibitors. The irreversible binding of these inhibitors was achieved by substituting the 6 or 7 position of the quinazoline ring of an 4-(anilino)quinazoline derivative with an $\alpha,\beta$-unsaturated carboxylic group, preferably an acrylamide group, which binds covalently to the Cys-773 at the EGFR-TK ATP binding site. Some of these compounds showed high potency toward EGFR inhibition in both in vitro and in vivo experiments (Smaill et al., 2000). However, as is detailed hereinunder, more recent studies showed that these irreversible EGFR-TK inhibitors are limited by a relatively low accumulation at EGFR-expressing tumor cells.

Hence, it would be highly advantageous to have irreversible EGFR-TK inhibitors with improved efficacy, which could serve as potent anticancer agents.

In addition to the growing efforts for targeting and inhibiting the EGFR in cancerous cells, the role that EGFR overexpression plays in cancer development is gradually unraveled. Consequently, there has been a growing interest in the use of EGFR-TK inhibitors as radiotracers for molecular imaging of EGFR overexpressing tumors via nuclear medicine modality such as Positron Emission Tomography (PET).

The use of radioactive nuclides for medicinal purposes is well known in the art. Biologically active compounds that bind to specific cell surface receptors or that otherwise modify cellular functions have received some consideration as radiopharmaceuticals, and therefore, when labeled with a radioactive nuclide, such compounds are used as biospecific agents in radioimaging and radiotherapy.

Positron Emission Tomography (PET), a nuclear medicine imagine technology which allows the three-dimensional, quantitative determination of the distribution of radioactivity within the human body, is becoming an increasingly important tool for the measurement of physiological, biochemical, and pharmacological function at a molecular level, both in healthy and pathological states. PET requires the administration to a subject of a molecule labeled with a positron-emitting. nuclide (radiotracer) such as $^{15}O$, $^{13}N$, $^{11}C$, and $^{18}F$, which have half-lives of 2, 10, 20, and 110 minutes, respectively.

Single Photon Emission Computed Tomography (SPECT) is a form of chemical imaging in which emissions from radioactive compounds, labeled with gamma-emitting radionuclides, are used to create cross-sectional images of radioactivity distribution in vivo. SPECT requires the administration to a subject of a molecule labeled with a gamma-emitting nuclide such as $^{99m}Tc$, $^{67}Ga$, $^{111}In$ and $^{123}I$.

The use of nuclear medicine imaging techniques such as Single Photon Emission Compute Tomography (SPECT) and Positron Emission Tomography (PET), along with a suitable radiotracer that binds to EGFR irreversibly, can therefore provide for in vivo drug development and identification of a lead chemical structure to be used as an EGFR-TK biospecific agent for radiotherapy or as a labeled bioprobe for diagnosis by radioimaging. Nuclear imaging can be further used for in vivo mapping and quantification of the receptor-kinase in cancer. Using a labeled EGFR-TK irreversible inhibitor would enable both the identification of patients having tumors overexpressing EGFR, and the study of changes in the levels of EGFR expression during therapy. Such a diagnostic method can lead to a better patient management and differentiation in regards to therapeutic course of action. Moreover, the increasing demand to incorporate diagnostic methods into clinical studies of EGFR-targeted therapies suggests a potential future use of EGFR-labeled inhibitors.

Radiolabeling of 4-anilinoquinazoline EGFR-TK inhibitors has been reported in the art. For example, a radioiodinated analog of PD 153035 and in vitro binding studies therewith in MDA-486 cells have been reported (Mulholland et al., 1995). PD 153035 labeled with carbon-11 in the 6,7-methoxy groups has been evaluated in rats implanted with human neuroblastoma xenografts (SH-SY5Y) but specific uptake was not determined in a blocking study (Johnstrom et al, 1998). PD 153035 was also labeled with carbon-11 specifically at the 7-methoxy position and biodistribution experiments were performed in normal mice, but uptake specificity could not be demonstrated as administration of an enzyme-blocking dose of PD 153035 caused an increase in tracer uptake in the tissues studied (Mulholland et al., 1997). The same abstract reported the labeling of the 7-(2-fluoroethoxy) PD 153035 analog with fluorine-18, but no biological experiments with this tracer were described.

U.S. Pat. No. 6,126,917 (to the present assignee), which is incorporated by reference as if fully set forth herein, Mishani et al., 1999 and Bonasera et al., 2000, all teach reversible inhibitors of EGFR-TK of the 4-anilinoquinazoline family labeled with fluorine-18 on the aniline ring. These compounds were tested in vitro, in vivo and by PET image analysis. While some of these compounds showed effective (reversible) inhibition activity in vitro, they were found to exhibit limited efficiency as tracers for the imaging of EGFR-TK in vivo due to kinetic factors such as $k_{on}$ and $k_{off}$ and rapid blood clearance, as was further demonstrated by an animal PET comparative study between fluorine-18 FDG and these radiolabeled compounds. It is assumed that the discrepancy between the encouraging in vitro results and the discouraging in vivo results derives from the ATP competition at the compounds' binding site.

In order to eliminate this ATP binding competition and thus obtain a better specificity and inhibitory effect of radiolabeled EGFR-TK inhibitors, which would potentially result in higher diagnostic performance and high radiotherapeutic activity in tumor cells expressing EGFR-TK, radiolabeled irreversible inhibitors, based on those described by Smaill et al. (Smaill et al., 2000), were synthesized.

As is taught in U.S. Pat. No. 6,562,319 (to the present assignee), which is incorporated by reference as if fully set forth herein, and in Ben David et al., 2003, acrylamido derivatives of 4-anilinoquinazoline were synthesized, radiolabeled by $^{11}C$ and tested for PET imaging of tumor cells overexpressing EGFR-TK. Indeed, these compounds showed irreversible and fast binding effect toward EGFR in in vitro studies conducted with A431 cells. However, while the ATP binding competition was eliminated and long-term inhibitory effect was obtained with these compounds in vitro, the in vivo studies in tumor bearing rats did not indicate high accumulation of the compounds in the tumor. In further in vivo studies, fast decomposition and clearance, as well as high accumulation of the compounds in the intestine, were observed, suggesting that the performance of this class of compounds is limited by low in vivo bioavailability and degradation.

Therefore, further studies have focused on the design and development of novel derivatives of irreversible inhibitors as PET imaging agent candidates (Mishani et al., 2004). U.S. patent application Ser. No. 10/659,747 (Publication No. 2004/0265228, recently granted), which is incorporated by reference as if fully set forth herein, discloses, for example, a novel group of compounds, the 4-dimethylamino-but-2-enoicacid [4-(phenylamino)-quinazoline-6-yl]-amides. These compounds held a favorable profile, characterized by a remarkable inhibitory potency toward the EGFR, elevated chemical and biological stabilities and sufficient selectivity with respect to other tested tyrosine kinase receptors. The lead compound of this group, referred to as ML04 (see, FIG. 1a), was labeled with $^{11}C$ and $^{18}F$, and its potential as EGFR PET imaging agent was evaluated. However, these irreversible compounds exhibited insufficient bioavailability, characterized by low circulating blood levels after oral administration. This limited performance was attributed to the low solubility of these compounds under physiological conditions and to rapid metabolic pathway caused by the chemical reactivity of the acrylamide and butynamide unsaturated bonds.

In International Patent Application WO 04/064718, which is incorporated by reference as if fully set forth herein, a novel class of irreversible EGFR-TK inhibitors characterized by reduced biodegradation, enhanced bioavailability and hence by improved in vivo performance as compared with the structurally related reversible and irreversible EGFR-TK inhibitors described above, has been disclosed. The compounds belonging to this newly designed class have a leaving group such as α-chloroacetamide or an α-methoxyacetamide group attached to the quinazoline ring. According to the teachings of WO 04/064718, it was found that replacing the α,β-unsaturated side chain of the highly reactive carboxylic moiety, by the less reactive chloro and methoxy groups, which can further act as leaving groups and thus readily react so as to form a covalent bond with the cysteine moiety at the receptor binding site, resulted in potent irreversible inhibitors with enhanced biostability and bioavailability. It was thus found that such newly designed compounds, having an α-chloroacetamide or an α-methoxyacetamide group attached to the quinazoline ring, show high affinity toward EGFR and high ability to irreversibly bind to the receptor, thus indicating their potential as improved EGFR-TK irreversible inhibitors and as a result as improved diagnostic and therapeutic agents. A representative member of this family of irreversible EGFR inhibitors is referred to herein as ML05 (see, FIG. 1b). Nonetheless, the use of these compounds remained limited due to insufficient solubility and biological stability thereof.

There is thus a widely recognized need for, and it would be highly advantageous to have, novel radiolabeled and non-radiolabeled inhibitors of EGFR-TK, devoid of the above limitations.

One common way to increase the blood-residency of proteins is by conjugating the proteins to a non-proteinaceous substance such as polyethylene glycol (PEG). Conjugation of PEG to proteins results in increased molecular size and stearic hindrance of the protein and, as a result, often improves the plasma half-lives and proteolytic-stability of the proteins, and decreases their immunogenicity and hepatic uptake (Chaffee et al., 1992; Pyatak et al., 1980). Conjugation of PEG further increases the solubility of proteins in body fluids.

The prior art, however, fails to teach or suggest conjugation of PEG to EGFR-TK inhibitors such as those described hereinabove.

SUMMARY OF THE INVENTION

The present inventors have now designed and successfully prepared and practiced novel inhibitors of EGFR-TK which are characterized by improved solubility, bioavailability and biostability. These novel inhibitors are based on (4-anilinoquinazolinyl)amide derivatives that have a polyalkylene glycol moiety attached thereto and hence are conjugates of an (4-anilinoquinazolinyl)amide derivative and a polyalkylene glycol moiety. The novel compounds described herein were further designed capable of being radiolabeled at predetermined positions. Thus, processes for efficiently radiolabeling the novel inhibitors of EGFR-TK disclosed herein have been developed and novel radiolabeled inhibitors of EGFR-TK were prepared.

Hence, according to one aspect of the present invention there is provided a compound having the general Formula I:

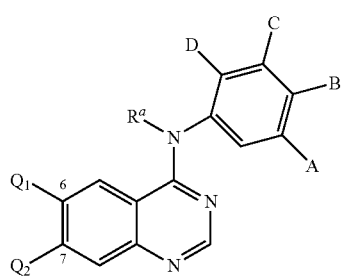

Formula I and comprising a polyalkylene glycol moiety being covalently attached thereto, wherein:

Q1 is X—W(=Y)—Z and Q2 is selected from the group consisting of hydrogen, halogen, alkoxy, hydroxy, thiohydroxy, thioalkoxy, alkylamino and amino or absent, or Q1 is selected from the group consisting of hydrogen, halogen, alkoxy, hydroxy, thiohydroxy, thioalkoxy, alkylamino and amino or absent and Q2 is X—W(=Y)—Z;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;

W is carbon;

Y is selected from the group consisting of oxygen and sulfur;

Z is selected from the group consisting of —R$^2$C=CHR$^3$, —C≡C—R$^3$, —R$^2$C=C=CHR$^3$ and —CR$^4$R$^5$R$^6$;

R$^a$ is selected from the group consisting of hydrogen or alkyl having 1-8 carbon atoms;

A, B, C and D are each independently selected from the group consisting hydrogen and a first derivatizing group;

R$^1$ is selected from the group consisting of hydrogen, and substituted or non-substituted alkyl having 1-6 carbon atoms;

R$^2$ is selected from the group consisting of hydrogen, halogen and alkyl having 1-6 carbon atoms;

R$^3$ is selected from the group consisting of hydrogen, halogen, carboxy, alkenyl, alkoxy, carbonyl, substituted or non-substituted alkyl having 1-6 carbon atoms and substituted or non-substituted phenyl;

R$^4$ is a leaving group; and

R$^5$ and R$^6$ are each independently selected from the group consisting of hydrogen and a second derivatizing group.

According to further features in preferred embodiments of the invention described below, the polyalkylene glycol moiety has a general Formula II:

 Formula II wherein:

m is an integer from 1 to 6;

n is an integer from 1 to 100;

U is O, S or NR'";

V is a third derivatizing group selected from the group consisting of hydroxyl, thiol, amine, alkyl, cycloalkyl, aryl, heteroalicyclic, heteroaryl, halogen, haloalkyl, alkoxy, thioalkoxy, aryloxy, thioaryloxy, alkenyl, alkynyl, amide, carboxylate, thiocarboxylate, sulfinyl, sulfonyl, carbamyl, thiocarbamyl, nitro and cyano; and R', R" and R'" are each independently selected from the group consisting of hydrogen, alkyl, aryl and cycloalkyl.

According to still further features in the described preferred embodiments Q1 is X—W(=Y)—Z, Q2 is absent and the polyalkylene glycol is attached at position 7 of the compound having the Formula I.

According to still further features in the described preferred embodiments the leaving group is selected from the group consisting of alkoxy and halogen.

According to still further features in the described preferred embodiments Z is —CR$^4$R$^5$R$^6$.

According to still further features in the described preferred embodiments Z is selected from the group consisting of —R$^2$C=CHR$^3$, —C≡C—R$^3$ and —R$^2$C=C=CHR$^3$.

According to still further features in the described preferred embodiments the R$^3$ is a substituted alkyl having 1-6 carbon atoms.

According to still further features in the described preferred embodiments the substituted alkyl comprises a substituted amino group.

According to still further features in the described preferred embodiments the substituted amino group comprises a hydroxy-containing moiety such as, for example, one or more hydroxyalkyl groups.

According to still further features in the described preferred embodiments the compound further comprises a hydroxy-containing moiety such as, but not limited to, hydroxy, hydroxyalkyl and an additional polyalkylene glycol moiety.

According to still further features in the described preferred embodiments X is the —NR$^1$— and Y is oxygen.

According to still further features in the described preferred embodiments at least one of A, B, C and D is fluorine, preferably D is fluorine.

According to still further features in the described preferred embodiments A is bromine or iodine.

According to another aspect of the present invention there is provided a pharmaceutical composition comprising as an active ingredient the compound as described hereinabove and a pharmaceutical acceptable carrier.

According to further features in preferred embodiments of the invention described below, the composition is packaged in a packaging material and identified in print, in or on the packaging material, for use in the treatment of an EGFR-tyrosine kinase related disease or disorder.

According to still another aspect of the present invention there is provided a method of treating an EGFR-tyrosine kinase related disease or disorder in a subject in need thereof, the method comprising administering to the subject a therapeutically effective amount of the pharmaceutical composition described herein.

According to yet another aspect of the present invention there is provided a use of the compound described herein in the manufacture of a medicament for treating an EGFR-tyrosine kinase related disease or disorder.

According to still another aspect of the present invention there is provided a method of inhibiting cell proliferation, the method comprising subjecting the cell to the compound described herein.

According to an additional aspect of the present invention there is provided a radiolabeled compound having the general Formula I*:

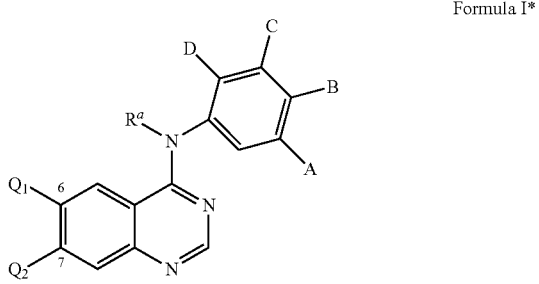

Formula I* and comprising a radiolabeled polyalkylene glycol or a non-radiolabeled polyalkylene glycol moiety being covalently attached thereto,
wherein:

Q1 is X—W(=Y)—Z and Q2 is selected from the group consisting of hydrogen, halogen, alkoxy, hydroxy, thiohydroxy, thioalkoxy, alkylamino and amino or absent, or Q1 is selected from the group consisting of hydrogen, halogen, alkoxy, hydroxy, thiohydroxy, thioalkoxy, alkylamino and amino or absent and Q2 is X—W(=Y)—Z;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;

W is selected from the group consisting of a non-radioactive carbon and a radioactive carbon;

Y is selected from the group consisting of oxygen and sulfur;

Z is selected from the group consisting of —R$^2$C=CHR$^3$, —C=C—R$^3$, —R$^2$C=C=CHR$^3$ and —CR$^4$R$^5$R$^6$;

R$^a$ is selected from the group consisting of hydrogen or alkyl having 1-8 carbon atoms;

A, B, C and D are each independently selected from the group consisting of hydrogen, a first non-radioactive derivatizing group and a first radioactive derivatizing group selected from a radioactive bromine, a radioactive iodine and a radioactive fluorine;

R$^1$ is selected from the group consisting of hydrogen, and substituted or non-substituted alkyl having 1-6 carbon atoms;

R$^2$ is selected from the group consisting of hydrogen, halogen and alkyl having 1-6 carbon atoms;

R$^3$ is selected from the group consisting of hydrogen, halogen, carboxy, alkenyl, alkoxy, carbonyl, substituted or non-substituted alkyl having 1-6 carbon atoms, substituted or non-substituted phenyl and substituted or non-substituted alkyl having 1-6 carbon atoms at least one being a radioactive carbon;

R$^4$ is a leaving group; and

R$^5$ and R$^6$ are each independently selected from the group consisting of hydrogen and a second derivatizing group, the compound comprising at least one radioactive atom.

According to further features in preferred embodiments of the invention described below, the polyalkylene glycol moiety has a general Formula II*:

—[U(CR'R'')m]nV          Formula II* wherein:
m is an integer from 1 to 6;
n is an integer from 2 to 100;
U is O, S or NR''';
V is selected from the group consisting of a radioactive third derivatizing group and a non-radioactive third derivatizing group selected from the group consisting of a radioactive group, hydroxyl, thiol, amine, alkyl, cycloalkyl, aryl, heteroalicyclic, heteroaryl, halogen, haloalkyl, alkoxy, thioalkoxy, aryloxy, thioaryloxy, alkenyl, alkynyl, amide, carboxylate, thiocarboxylate, sulfinyl, sulfonyl, carbamyl, thiocarbamyl, nitro and cyano; and R', R'' and R''' are each independently selected from the group consisting of hydrogen, alkyl, aryl and cycloalkyl.

According to still further features in the described preferred embodiments V is a non-radioactive derivatizing group selected from the group consisting of hydroxy and halogen.

According to still further features in the described preferred embodiments Q1 is X—W(=Y)—Z, Q2 is absent and the polyalkylene glycol moiety is attached at position 7 of the compound having the Formula I.

According to still further features in the described preferred embodiments the leaving group is selected from the group consisting of alkoxy and halogen.

According to still further features in the described preferred embodiments X is —NR$^1$— and Y is oxygen.

According to still further features in the described preferred embodiments W is the radioactive carbon.

According to still further features in the described preferred embodiments at least one of A, B, C and D is the first radioactive derivatizing group.

According to still further features in the described preferred embodiments the at least one radioactive atom forms a part of the polyalkylene glycol moiety.

According to still further features in the described preferred embodiments the polyalkylene glycol moiety has the general Formula II*:

—[U(CR'R'')m]nV          Formula II* and V is the radioactive third derivatizing group.

According to still further features in the described preferred embodiments the radioactive third derivatizing group comprises at least one radioactive atom selected from the group consisting of a radioactive carbon a radioactive fluorine, a radioactive bromine and a radioactive iodine.

According to still further features in the described preferred embodiments V is a radioactive fluorine.

According to still further features in the described preferred embodiments Z is —CR⁴R⁵R⁶:

According to still further features in the described preferred embodiments Z is selected from the group consisting of —R²C=CHR³, —C≡C—R³ and —R²C=C=CHR³.

According to still further features in the described preferred embodiments R³ is a substituted alkyl having 1-6 carbon atoms.

According to still further features in the described preferred embodiments the substituted alkyl comprises a radioactive atom.

According to still further features in the described preferred embodiments the substituted alkyl comprises a substituted amino group.

According to still further features in the described preferred embodiments the substituted amino group comprises a radioactive atom.

According to still further features in the described preferred embodiments the substituted amino group comprises one or more hydroxy-containing moiety or moieties such as, for example, a hydroxyalkyl group.

According to still further features in the described preferred embodiments the radiolabeled compound further comprises at least one hydroxy-containing moiety such as, but not limited to, hydroxy, a hydroxyalkyl and an additional polyalkylene glycol moiety, being covalently attached thereto.

According to still an additional aspect of the present invention there is provided a pharmaceutical composition comprising the radiolabeled compound described herein and a pharmaceutically acceptable carrier.

According to yet an additional aspect of the present invention there is provided a method of monitoring the level of epidermal growth factor receptor within a body of a patient, the method comprising: (a) administering to the patient the radiolabeled compound described herein; and employing a nuclear imaging technique for monitoring a distribution of the compound within the body or within a portion thereof.

According to still an additional aspect of the present invention there is provided a use of the radiolabeled compound described herein in the manufacture of a diagnostic agent for monitoring the level of epidermal growth factor receptor within a body of a patient.

According to another aspect of the present invention there is provided a method of radiotherapy comprising administering to a patient a therapeutically effective amount of the pharmaceutical composition described herein, which comprises the radiolabeled compound as described herein.

According to yet another aspect of the present invention there is provided a use of the radiolabeled compound described herein in the manufacture of a medicament for radiotherapy.

According to still another aspect of the present invention there is provided a method of inhibiting cell proliferation, the method comprising subjecting the cell to the radiolabeled compound described herein.

According to further aspects of the present invention there are provided methods of synthesizing the non-labeled and radiolabeled compounds described herein.

In one particular embodiment, there is provided a method of synthesizing a radiolabeled compound having the general Formula VIII:

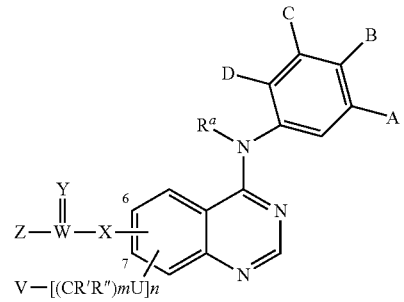

Formula VIII wherein:

X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;

W is carbon;

Y is selected from the group consisting of oxygen and sulfur;

Z is selected from the group consisting of —R²C=CHR³, —C≡C—R³, —R²C=C=CHR³ and —CR⁴R⁵R⁶;

Rᵃ is selected from the group consisting of hydrogen or alkyl having 1-8 carbon atoms;

A, B, C and D are each independently selected from the group consisting hydrogen and a first derivatizing group;

R¹ is selected from the group consisting of hydrogen, and substituted or non-substituted alkyl having 1-6 carbon atoms;

R² is selected from the group consisting of hydrogen, halogen and alkyl having 1-6 carbon atoms;

R³ is selected from the group consisting of hydrogen, halogen, carboxy, alkenyl, alkoxy, carbonyl, a substituted or non-substituted alkyl having 1-6 carbon atoms, and substituted or non-substituted phenyl;

R⁴ is a leaving group;

R⁵ and R⁶ are each independently selected from the group consisting of hydrogen and a second derivatizing group;

m is an integer from 1 to 6;

n is an integer from 2 to 100;

U is O, S or NR'";

V is a radioactive third derivatizing group; and

R', R" and R'" are each independently selected from the group consisting of hydrogen, alkyl, aryl and cycloalkyl, the method comprising:

coupling an 4-anilinoquinazoline derivatized by Rᵃ, A, B, C and D, as defined, and substituted at the quinazoline ring by a first and a second reactive groups, with a polyalkylene glycol derivatized by R', R" and R'" and by V', as defined, and substituted by a third reactive group capable of reacting with the second reactive group, wherein V' is a fifth reactive group, to thereby produce a 4-anilinoquinazoline substituted by the first reactive group and further substituted by the polyalkylene glycol moiety derivatized by the fifth reactive group;

reacting the 4-anilinoquinazoline substituted by the first reactive group and by the polyalkylene glycol moiety derivatized by the fifth group with a reactive carboxylic derivative that comprises the Z at the α position; and converting the fifth reactive group into a radioactive group.

Further according to the present invention there is provided a compound having the general Formula I, as described herein, and comprising at least one hydroxy-containing moiety being covalently attached thereto, The hydroxy-containing moiety can be, for example, hydroxy, a hydroxyalkyl and/or a polyalkylene glycol moiety.

Radiolabeled such compounds, pharmaceutical compositions containing such compounds and methods utilizing such compounds, as described herein, are also provided.

The present invention successfully addresses the shortcomings of the presently known configurations by providing novel, non-labeled and radiolabeled inhibitors of EGFR-TK which are characterized by improved solubility, bioavailability and biostability, and further by providing novel synthetic pathways for producing these non-labeled and radiolabeled inhibitors.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

As used herein, the singular form "a", "an" and "the" include plural references unless the context clearly dictates otherwise. For example, the term "a protein" or "at least one protein" may include a plurality of proteins, including mixtures thereof.

As used herein the term "about" refers to ±10%.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "about" refers to ±10%.

As used herein throughout, the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

(FIG. 3*a*); a scheme presenting the synthetic route for preparing representative examples of compounds according to the present invention (Compounds 10a-c), wherein the synthetic procedures involve reaction with bromo/chlorocrotonylchloride and N,N-DIPEA in THF at 0° C. (a) and reaction with DMA in THF solution (2M) and N,N-DIPEA in THF at 0° C. (b) (FIG. 3*b*); and a scheme presenting the synthetic route for preparing representative examples of compounds according to the present invention (Compounds 60*b* and 73*b*);

DESCRIPTION OF THE PREFERRED EMBODIMENTS

Figure 1A:
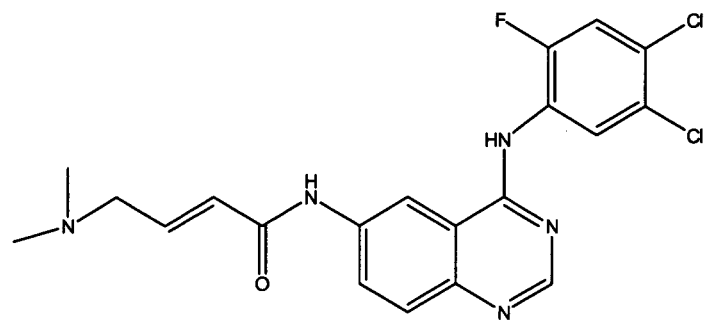
FIG. 1 presents the chemical structures of background art compounds 4-dimethylamino-but-2-enoic acid [4-(3,4-dichloro-6-fluoro-phenylamino)-quinazoline-6-yl]-amide (ML04, FIG. 1*a*) and N-{4-[(3-bromophenyl)amino]-quinazolin-6-yl}-2-chloroacetamide (ML05, FIG. 1*b*)

The present invention is of novel compounds of 4-anilinoquinazoline derivatives and polyalkylene glycols or other hydroxy-containing moieties, which are EGFR-TK inhibitors and can therefore be used in the treatment of EGFR related diseases or disorders, and which can further be radiolabeled and thus used as biomarkers for radioimaging such as Positron Emission Tomography (PET) and Single Photon Emission Computed Tomography (SPECT) and as radiopharmaceuticals for radiotherapy. Specifically, the non-labeled and radiolabeled compounds of the present embodiments can be used as therapeutic agents in the treatment of disorders or diseases, such as a variety of cancers, in which amplification, mutation and/or over expression of EGFR-TK has occurred, whereby the radiolabeled compounds of the present invention can be further used as PET or SPECT biomarkers for quantification, mapping and radiotherapy of such EGFR-TK associated diseases or disorders. The present invention is further of pharmaceutical compositions containing these compounds and of chemical and radio-syntheses of these compounds. The novel EGFR-TK inhibitors of the present embodiments are characterized by enhanced solubility (e.g., in body fluids), biostability and bioavailability due to the presence of a polyalkylene glycol moiety or other hydroxy-containing moiety.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

As discussed in detail hereinabove, overexpression of the EGFR has been linked to cell malignancy, metastasis and poor prognosis, thus rendering it a target for several FDA approved drugs. Unfortunately, these drugs have yielded suboptimal clinical results.

In U.S. Pat. No. 6,562,319, U.S. patent application Ser. No. 09/802,928 (Publication No. 2004/0265228, recently granted), and WO 04/064718 it is disclosed that labeled derivatives of [4-(phenylamino)quinazolinyl]amides (also referred to herein and in the art as (4-anilinoquinazoline-6-yl)amide) family held a remarkable irreversible inhibitory potency toward the EGFR, and moderate chemical and biological stabilities, designating this family of inhibitors as potent candidates for EGFR imaging and related therapy.

While biostability, bioavailability and solubility are important features for tracer qualifications, both in imaging and therapy, EGFR-TK inhibitors characterized by improved biostability, bioavailability and solubility have been sought for.

In a search for such inhibitors, the present inventors have envisioned that coupling a polyalkylene glycol moiety to the potent (4-anilinoquinazolinyl)amides EGFR-TK inhibitors would result in improved solubility, bioavailability and biostability of these compounds.

While reducing the present invention to practice, [4-(phenylamino)-quinazoline-6-yl]-amide derivatives substituted at position 7 by various fluoro-polyethylene glycol (F-PEG) and hydroxy-polyethylene glycol chains were successfully synthesized. Preliminary studies indicated that in intact glioma cells, these novel derivatives exhibited potent autophosphorylation inhibitory activity. Additional preliminary studies revealed that these compounds are characterized by controllable lipophilicity, controlled as desired by, e.g., manipulating the length and substituents of the PEG chain.

These novel compounds were further successfully labeled with fluorine-18 at the PEG chain via novel three-step radiosynthesis route and one-step synthetic route, thus providing an improved pathway for radiolabeling. The obtained radiolabeled compounds have radiochemical purity higher than 99%, and specific activity of 4000 Ci/mmol.

It has thus been demonstrated that [4-(phenylamino)-quinazoline-6-yl]-amide derivatives having a polyalkylene glycol moiety attached thereto exhibit, in addition to high affinity toward EGFR and high ability to bind to the receptor, controllable lipophilicity and water solubility, and can therefore serve as potent EGFR-TK inhibitors and as a result as therapeutic agents with improved pharmacokinetic characteristics.

It has been further demonstrated that by designing such compounds that could be further efficiently subjected to radiolabeling by various radioisotopes, novel radiolabeled EGFR-TK inhibitors, which can serve as improved diagnostic and radiotherapeutic agents, can be prepared.

Thus, according to one aspect of the present invention there are provided novel compounds, each comprising a first moiety and a second moiety covalently linked therebetween.

As used herein, the term "moiety" describes a major portion of a molecule that is covalently attached to another molecule, preferably while maintaining its main structural features. The term "moiety" is also referred to in the art as a "radical", presenting that portion of a molecule that is obtained after covalently linking the molecule to another molecule.

The first moiety in the compounds described herein is a polyalkylene glycol and the second moiety is a 4-anilinoquinazoline derivative having the general Formula I:

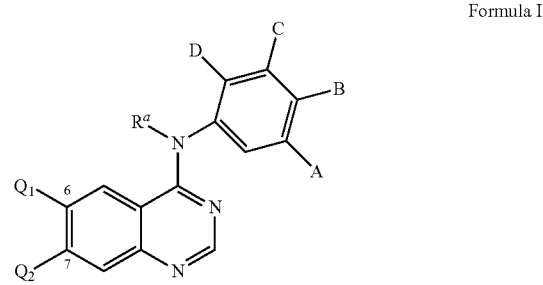

Formula I wherein:

Q1 is X—W(=Y)—Z and Q2 is selected from the group consisting of hydrogen, halogen, alkoxy, hydroxy, thiohydroxy, thioalkoxy, alkylamino and amino or absent, or Q1 is selected from the group consisting of hydrogen, halogen, alkoxy, hydroxy, thiohydroxy, thioalkoxy, alkylamino and amino or absent and Q2 is X—W(=Y)—Z;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;

W is carbon;

Y is selected from the group consisting of oxygen and sulfur;

Z is selected from the group consisting of —R$^2$C=CHR$^3$, —C=C—R$^3$, —R$^2$C=C=CHR$^3$ and —CR$^4$R$^5$R$^6$;

R$^a$ is selected from the group consisting of hydrogen or alkyl having 1-8 carbon atoms;

A, B, C and D are each independently selected from the group consisting hydrogen and a first derivatizing group, as defined herein;

R$^1$ is selected from the group consisting of hydrogen, and substituted or non-substituted alkyl having 1-6 carbon atoms;

R$^2$ is selected from the group consisting of hydrogen, halogen and alkyl having 1-6 carbon atoms;

R$^3$ is selected from the group consisting of hydrogen, halogen, carboxy, alkenyl, alkoxy, carbonyl, substituted or non-substituted alkyl having 1-6 carbon atoms and substituted or non-substituted phenyl;

R$^4$ is a leaving group, as defined herein; and

R$^5$ and R$^6$ are each independently selected from the group consisting of hydrogen and a second derivatizing group, as defined herein.

As used herein, the phrase "polyalkylene glycol" encompasses any compound that comprises a chain of two or more fragments, each including an alkylene chain that is interrupted by an oxygen atom. This phrase, however, further encompasses, according to the present embodiments, analogs of polyalkylene glycols comprised of two or more fragments, each including an alkylene chain that is interrupted by a heteroatom other than oxygen, such as S and/or N. The polyalkylene glycols described herein can therefore be comprised, for example, of fragments of aminoalkyls, hydroxyalkyls (alkoxy), thiohydroxyalkyls (thioalkoxy), and the like, whereby the alkylene chain in each fragment can be further substituted. The fragments composing the polyalkylene glycol can be the same or different, in terms of the length of the alkylene chain, the substituents and/or the heteroatom, and are preferably the same.

Thus, according to preferred embodiments of the present invention, the polyalkylene glycol moiety is represented by the general Formula II:

—[U(CR'R")m]nV    Formula II wherein:

m is an integer from 1 to 6, representing the length of the alkylene chain in each of the fragments composing the polyalkylene glycol moiety;

n is an integer from 2 to 100, representing the number of fragments composing the polyalkylene glycol moiety;

U is O, S or NR'", representing the heteroatom interrupting the alkylene chain in each fragment;

V is a third derivatizing group, representing the end group in the polyalkylene glycol moiety, as is detailed hereinbelow; and R', R" and R'", representing the substituents of the polyalkylene glycol moiety, are each independently selected from the group consisting of hydrogen, alkyl, aryl and cycloalkyl.

Preferably, the polyalkylene glycol moiety is derived from polyalkylene glycol and hence U in Formula II above is O. Further preferably, the polyalkylene glycol moiety is derived from polyethylene glycol (PEG), such that m in Formula II above equals 2. Substituted and non-substituted PEGs, having various chain length (in terms of the number of fragments, n) are commercially available compounds, which are typically known as pharmaceutically acceptable compounds and hence are highly advantageous for use in the context of the present embodiments.

As discussed hereinabove, coupling a polyalkylene glycol to (4-anilinoquinazolinyl)amide derivatives enables to manipulate the lipophilicity and hence the solubility and biostability of the obtained compounds. The lipophilicity of the compounds can thus be controlled as desired by manipulating the features of the polyalkylene glycol moiety, namely, the chain length of the alkylene (m in Formula II above), the number of alkylene fragments (n in Formula II above), the chemical nature of the heteroatom (U in Formula II above), the chemical nature of the substituents (R', R" and R'" in Formula II above) and the chemical nature of the end group (V in Formula II above). Preferably, the polyalkylene glycol moiety is selected such that it decreases the lipophilicity (Log P) of the obtained compounds as compared to non-conjugated (4-anilinoquinazolinyl)amide derivatives, and hence increases the compound solubility in e.g., body fluids, while maintaining its binding characteristics to the EGFR-TK.

Thus, for example, the desired characteristics of the compounds can be controlled by using polyalkylene glycol moieties of various total lengths (namely, various numbers of alkylene fragments, n). Hence, n in Formula II above can be for example any integer from 2 to 100 and even higher (e.g., up to 1000). According to preferred embodiments, n is an integer from 2 to 20, preferably from to 2 to 10 and more preferably from 2 to 6. Relatively short chains are preferred so as to avoid interference with the binding activity of the compounds to EGFR-TK.

The desired characteristics of the compounds can be further controlled, for example, by manipulating the nature of the end group (V in Formula II above). Thus, for example, V can be the natural end group of a selected polyalkylene glycol, namely, a group derived from the interrupting heteroatom (e.g., hydroxy, thiohydroxy or amine). Alternatively, the polyalkylene glycol can be derivatized so as to terminate by other groups, as desired.

Hence, exemplary polyalkylene glycol moieties according to preferred embodiments of the present invention can be selected or derivatized so as to terminate by an end group such as, but not limited to, hydroxyl, thiol, amine, alkyl, cycloalkyl, aryl, heteroalicyclic, heteroaryl, halogen, haloalkyl, alkoxy, thioalkoxy, aryloxy, thioaryloxy, alkenyl, alkynyl, amide, carboxylate, thiocarboxylate, sulfinyl, sulfonyl, carbamyl, thiocarbamyl, nitro and cyano, as these terms are defined herein.

In preferred embodiments of the present invention, the polyalkylene glycol moiety is terminated by a hydroxy group or by a halogen. As is demonstrated in the Examples section that follows, derivatizing the polyalkylene glycol moiety by a halogen or a hydroxy allows an efficient radiolabeling of the compounds.

As is described in the art (see, for example, Smaill et al., 2000, and U.S. Pat. Nos. 6,126,917 and 6,562,319 and WO 04/064718), the level of the biological activity of 4-(phenylamino)quinazoline EGFR-TK inhibitors, whether reversible or irreversible, is influenced by the nature of the derivatizing groups at both the anilino ring and the quinazoline ring thereof. The nature of these derivatizing groups may affect the binding affinity of the compound to the receptor as well as other biological activity parameters such as specificity, metabolism of the compound and kinetic rates. Thus, it was found, for example, that substituting position 7 (see, Formula I above) of the quinazoline ring by various groups affects the biostability and bioavailability of these compounds.

While the compounds of the present embodiments were designed so as to exhibit enhanced bioavailability and/or biostability, preferably, the polyalkylene glycol moiety is attached to the quinazoline ring in the 4-(phenylamino) quinazolinyl moiety.

More preferably, the polyalkylene glycol moiety is attached at position 6 or 7 (see, Formula I above) of the quinazoline ring. According to these embodiments, Q2 or Q1, respectively, is absent.

Thus, according to preferred embodiments, Q1 is X—W(=Y)—Z, Q2 is absent and the polyalkylene glycol is attached at position 7 of the compound having Formula I.

Alternatively, Q2 is X—W(=Y)—Z, Q1 is absent and the polyalkylene glycol is attached at position 6 of the compound having Formula I.

Another factor which was found to influence the binding potency of 4-(phenylamino)quinazolinyl amide derivatives is the position at which the carboxylic group (X—W(=Y)—Z in Formula I above) is attached to the quinazoline ring. A 6-position carboxylic group has higher binding potency to the EGFR-TK ATP site (see, for example, Smaill et al, 1999, Smaill et al., 2000 and U.S. Pat. Nos. 6,153,617 and 6,127,374). Thus, according to another preferred embodiment of the present invention, the X—W(=Y)—Z group of the compound is attached to position 6 of the quinazoline ring, such that Q1 in Formula I above is X—W(=Y)—Z.

According to the presently most preferred embodiments of the present invention, Q1 in Formula I above is X—W(=Y)—Z, Q2 is absent, and the polyalkylene glycol moiety is attached at position 7 of the quinazoline ring.

As discussed hereinabove, studies have shown that substituting the 6 or 7 position of the quinazoline ring of an 4-(anilino)quinazoline derivative with an α,β-unsaturated carboxylic group, preferably an acrylamide group, results in covalent binding to the Cys-773 at the EGFR-TK ATP binding site, whereby the α,β-unsaturated carboxylic group acts as a Michael acceptor, and hence provides for irreversible inhibition of the receptor enzyme.

As used herein, the term "α,β-unsaturated carboxylic group" refers to any group that comprises a —C(=O)— or a —C(=S)— group and is linked at the distal end thereof to an unsaturated group. The carboxylic group forms a part of, for example, an amide, an ester, a hydrazinamide or a ketone.

The term "unsaturated group" refers to a substituted or non-substituted hydrocarbon that comprise at least two carbon atoms and at least one unsaturated bond. Representative examples of an unsaturated group include alkenyl, alkynyl and diene.

Thus, according to preferred embodiments of the present invention, Z in Formula I above represents an unsaturated group such —R$^2$C=CHR$^3$, R$^2$—C≡C—R$^3$ or —R$^2$C=C=CHR$^3$.

In one preferred embodiment, the α,β-unsaturated carboxylic group is an acrylamide group.

The acrylamide group can be further derivatized by a derivatizing group, as defined herein and represented by R$^2$ and R$^3$ in Formula I. The derivatizing group can be, for example, halogen, carboxy, alkenyl, alkoxy, carbonyl, substituted or non-substituted alkyl and substituted or non-substituted phenyl, as these terms are defined herein.

As further discussed hereinabove, additional studies have shown that substituting the acrylamide group by an alkyl, and preferably by an aminoalkyl, provides for improved binding of the 4-anilinoquinazoline to the EGFR.

U.S. patent application Ser. No. 09/802,928 (Publication No. 2004/0265228, recently granted), which is incorporated by reference as if fully set forth herein, discloses, for example, a novel group of compounds, the 4-dimethylamino-but-2-enoicacid [4-(phenylamino)-quinazoline-6-yl]-amides (also referred to herein as 4-(dimethylamino)-N-[4-(phenylamino)-quinazoline-6-yl]-2-butenamide), which held a favorable profile, characterized by a remarkable inhibitory potency toward the EGFR, elevated chemical and biological stabilities and sufficient selectivity with respect to other tested tyrosine kinase receptors. The lead compound of this group is referred to herein and in the art as ML04 (see, FIG. 1a).

Thus, according to another preferred embodiment of the present invention, the α,β-unsaturated carboxylic group is 4-(dialkylamino)-2-butenamide.

Figure 1B:
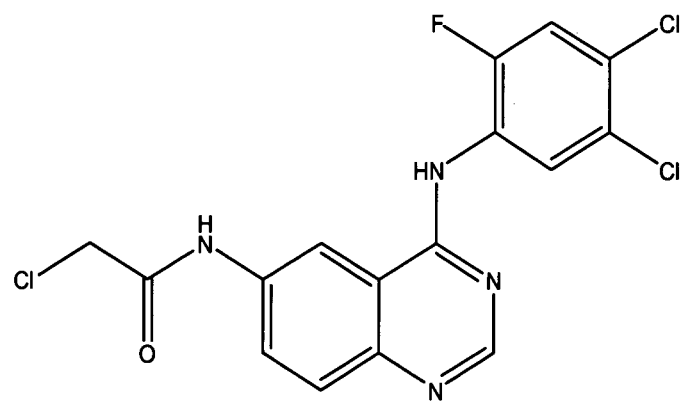

Recent studies have further shown that replacing the α,β-unsaturated side chain of the highly reactive carboxylic moiety, by the less reactive chloro and methoxy groups, which can further act as leaving groups and thus readily reacts so as to form a covalent bond with the cysteine moiety at the receptor binding site, resulted in potent irreversible inhibitors with enhanced biostability and bioavailability. Thus, WO 04/064718 discloses a novel class of irreversible EGFR-TK inhibitors that are based on 4-anilinoquinazoline and have a leaving group such as α-chloroacetamide or an α-methoxyacetamide group attached to the quinazoline ring. A representative member of this family of irreversible EGFR inhibitors is referred to herein and in the art as ML05 (see, FIG. 1b).

Hence, according to another preferred embodiment of the present invention, Z in Formula I above is —CR$^4$R$^5$R$^6$, whereby R$^4$ is a leaving group, as defined herein, and R$^5$ and R$^6$ are optionally derivatizing groups, as defined herein.

As used herein throughout, and is well known in the art, the phrase "leaving group" refers to a chemical moiety that can be easily replaced by a nucleophilic moiety in a nucleophilic reaction. Representative examples of leaving groups include, without limitation, halogen, alkoxy, aryloxy, thioalkoxy, thioaryloxy, sulfinyl, sulfonyl, carboxy and carbamyl, as these terms are defined hereinabove, with halogen and alkoxy being the presently most preferred. Additional examples of leaving groups include, without limitation, azide, sulfonamide, phosphonyl and phosphinyl.

Preferred compounds that have general Formula I above are therefore derivatized 4-(phenylamino)quinazolines (also referred to herein as 4-anilinoquinazolines), substituted at position 6 or 7 of the quinazoline ring by a carboxylic group, which is also defined herein as a X—W(=Y)—Z group, substituted at the α position by an unsaturated group or a leaving group, as defined herein.

In the presently most preferred embodiments of the present invention, the 6-position carboxylic group substituted by a leaving group is an α-chloroacetamide or α-methoxyacetamide group. Thus, preferred compounds according to the present invention are N-[4-(phenylamino)quinazolin-6-yl]-2-chloroacetamides and N-[4-(phenylamino)quinazolin-6-yl]-2-methoxyacetamides, derivatized by the R$^a$, A, B, C and D as these symbols are defined above, and further having a polyalkylene glycol moiety attached at position 7 of the quinazoline ring. These compounds are represented by Formula I hereinabove, wherein Q1 is X—W(=Y)—Z, X is —NH—, Y is oxygen, and Z is —CH$_2$Cl or CH$_2$OCH$_3$, respectively; Q2 is absent and a polyalkylene glycol moiety, as defined herein, is attached at position 7.

Further according to the presently most preferred embodiments of the present invention, the compounds are 4-dimethylamino-but-2-enoicacid [4-(phenylamino)-quinazoline-6- yl]-amides derivatized by the $R^a$, A, B, C and D, as these symbols are defined above, and further having a polyalkylene glycol moiety attached at position 7 of the quinazoline ring. These compounds are represented by Formula I hereinabove, wherein Q1 is X—W(=Y)—Z, X is —NH—, Y is oxygen, and Z is 4-(dialkylamino)-2-butene; Q2 is absent and a polyalkylene glycol moiety, as defined herein, is attached at position 7.

As discussed above, the level of the biological activity of 4-(phenylamino)quinazoline EGFR-TK inhibitors is further influenced by the nature of the derivatizing groups at the anilino ring. Thus, according to a preferred embodiment of the present invention, a derivatizing group is attached to the aniline ring (as is represented in Formula I hereinabove by A, B, C and D as a first derivatizing group) and includes, for example, hydrogen, halogen, alkyl, haloalkyl, hydroxy, alkoxy, carboxy, carbalkoxy, thiohydroxy, thiocarboxy, thioalkoxy, sulfinyl, sulfonyl, amino, alkylamino, carbamyl, nitro and cyano, as these terms are. defined herein.

As is taught, for example, in U.S. Pat. No. 6,126,917, 4-(phenylamino)quinazolines that are derivatized at position 6 of the anilino group by fluorine are potent inhibitors of EGFR-TK. The highest affinity toward the receptor is achieved using 4-[(3,4-dichloro-6-fluorophenyl)amino] quinazolines.

Thus, preferred compounds according to the present invention are those in which $R^a$ is hydrogen, A and B are each chlorine, C is hydrogen and D is fluorine.

As is taught in U.S. Pat. No. 6,562,319 and in U.S. Patent Application having the publication No. 2004/0265228, 4-(phenylamino)quinazolines that are derivatized at position 3 of the anilino group by bromine or iodine are also potent inhibitors of EGFR-TK. These compounds further serve as precursors for radioactive bromine or radioactive iodine labeled compounds, which, as is detailed hereinbelow, are highly potent radiolabeled compounds.

Hence, additional preferred compounds according to the present invention are those in which $R^a$ is hydrogen, A is bromine or iodine and B, C and D are each hydrogen.

The chemical structures of some of the preferred compounds according to the present embodiments are presented in FIG. 2.

As used herein, the phrase "derivatizing group" refers to a chemical moiety, as defined herein, that is covalently linked to another chemical moiety and serves as a substituent of the latter, thus providing a derivative of the another chemical moiety.

The term "halogen", which is also referred to herein as "halo", refers to fluorine, chlorine, bromine or iodine.

As used herein, the term "hydroxy" describes an —OH group.

As used herein, the terms "alkyl" and "alkylene" describe a saturated aliphatic hydrocarbon including straight chain and branched chain groups. Preferably, the alkyl group is a medium size alkyl having 1 to 10 carbon atoms. More preferably, it is a lower alkyl having 1 to 6 carbon atoms. Most preferably it is an alkyl having 1 to 4 carbon atoms. Representative examples of an alkyl group are methyl, ethyl, propyl, isopropyl, butyl, tert-butyl, pentyl and hexyl. Similarly, representative examples of an alkylene group are methylene, ethylene, propylene, isopropylene and butylene.

The alkyl or alkylene group, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, perhalo, trihalomethyl, carboxy, alkoxycarbonyl, thiocarboxy, carbamyl, cyano, nitro, N-piperidinyl, N-piperazinyl, $N_1$-piperazinyl-$N_4$-alkyl, N-pyrrolidyl, pyridinyl, N-imidazoyl, N-morpholino, N-thiomorpholino, N-hexahydroazepine, amino or NRbRc, wherein Rb and Rc are each independently hydrogen, alkyl, hydroxyalkyl, cycloalkyl, aryl, N-piperidinyl, N-piperazinyl, $N_1$-piperazinyl-$N_4$-alkyl, N-pyrrolidyl, pyridinyl, N-imidazoyl, N-morpholino, N-thiomorpholino and N-hexahydroazepine, as these terms are defined herein.

The term "haloalkyl" describes an alkyl group, as defined hereinabove, which is substituted by one or more halogen atoms.

The term "hydroxyalkyl" describes an alkyl group, as defined hereinabove, which is substituted by one or more free hydroxy groups.

As used herein, the term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane.

The term "alkoxy" describes both an —O-alkyl and an —O-cycloalkyl group, as defined hereinabove. Representative examples of alkoxy groups include methoxy, ethoxy, propoxy and tert-butoxy.

The —O-alkyl and the O-cycloalkyl groups, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, perhalo, trihalomethyl, carboxy, alkoxycarbonyl, thiocarboxy, carbamyl, cyano, nitro, N-piperidinyl, N-piperazinyl, $N_1$-piperazinyl-$N_4$-alkyl, N-pyrrolidyl, pyridinyl, N-imidazoyl, N-morpholino, N-thiomorpholino, N-hexahydroazepine, amino or NRbRc, wherein Rb and Rc are each independently hydrogen, alkyl, hydroxyalkyl, N-piperidinyl, N-piperazinyl, $N_1$-piperazinyl-$N_4$-alkyl, N-pyrrolidyl, pyridinyl, N-imidazoyl, N-morpholino, N-thiomorpholino and N-hexahydroazepine, as these terms are defined herein.

The term "thiohydroxy", which is also referred to herein as "thiol", describes a —SH group.

The term "thioalkoxy" describes both an —S-alkyl group, and an —S-cycloalkyl group, as defined herein.

The term "amino" or "amine" describes an —NH$_2$ group.

The term "alkylamino" describes a —NRbRc group wherein Rb and Rc are each independently hydrogen, alkyl, hydroxyalkyl, N-piperidinyl, N-piperazinyl, $N_1$-piperazinyl-$N_4$-alkyl, N-pyrrolidyl, pyridinyl, N-imidazoyl, N-morpholino, N-thiomorpholino and N-hexahydroazepine, as these terms are defined herein, or, alternatively, Rb and Rc are covalently attached one to the other so as to form a cyclic amino compound such as, but not limited to, N-piperidinyl, N-piperazinyl, $N_1$-piperazinyl-$N_4$-alkyl, N-pyrrolidyl, pyridinyl, N-imidazoyl, N-morpholino, N-thiomorpholino and N-hexahydroazepine.

The term "carboxy" or "carboxylate" describes a —C(=O)-ORx group, where Rx is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—Rx group, where Rx is as defined hereinabove.

The term "thiocarbonyl" describes a —C(=S)—Rx group, where Rx is as defined hereinabove.

An "aryl" group describes an all-carbon monocyclic or fused-ring polycyclic (i.e., rings which share adjacent pairs of carbon atoms) group having a completely conjugated pi-electron system. Examples, without limitation, of aryl groups are phenyl, naphthalenyl and anthracenyl.

A "phenyl" group, according to the present invention can be substituted by one to three substituents or non-substituted. When substituted, the substituent group may be, for example, halogen, alkyl, alkoxy, nitro, cyano, trihalomethyl, alkylamino or monocyclic heteroaryl.

The term "heteroaryl" group includes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

A "heteroalicyclic" group describes a monocyclic or fused ring group having in the ring(s) one or more atoms such as nitrogen, oxygen and sulfur. The rings may also have one or more double bonds. However, the rings do not have a completely conjugated pi-electron system.

An "aryloxy" group describes both an —O-aryl and an —O-heteroaryl group, as defined herein.

A "thioaryloxy" group describes both an —S-aryl and an —S-heteroaryl group, as defined herein.

A "trihalomethyl" group describes a —CX$_3$ group, wherein X is a halogen as defined herein. A representative example of a trihalomethyl group is a —CF$_3$ group.

A "perhalo" group describes a group in which all the hydrogen atoms thereof have been replaced by halogen atoms.

A "thiocarboxy" group describes a —C(=S)-ORx group, where Rx is as defined herein.

A "sulfinyl" group describes an —S(=O)—Rx group, where Rx is as defined herein.

A "sulfonyl" group describes an —S(=O)$_2$-Rx group, where Rx is as defined herein.

A "carbamyl" group describes an —OC(=O)-NRxRy group, where Rx is as defined herein and Ry is as defined for Rx.

A "nitro" group refers to a —NO$_2$ group.

A "cyano" group refers to a —C≡N group.

The term "N-piperazinyl", which is also referred to herein as "N-piperazino" refers to a

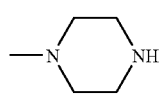

group.

The term "N-piperidinyl" refers to a

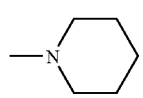

group.

The term "N$_1$-piperazinyl-N$_4$-alkyl" refers to a

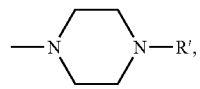

where R' is an alkyl, as defined hereinabove.

The term "N-pyrrolidyl" refers to a

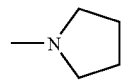

group.

The term "pyridinyl" refers to a

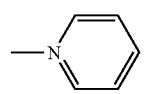

group.

The term "N-imidazoyl" refers to a

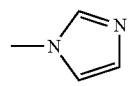

group.

The term "N-morpholino" refers to a

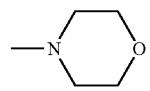

group.

The term "N-thiomorpholino" refers to a

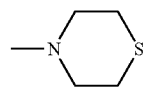

group.

The term "N-hexahydroazepine" refers to a

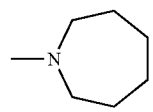

group.

As used herein, the term "azide" refers to a —N$_3$ group.

The term "sulfonamide" refers to a —S(=O)$_2$-NRxRy group, with Rx and Ry as defined herein.

The term "phosphonyl" describes an —O—P(=O)(ORx)$_2$ group, with Rx as defined hereinabove.

The term "phosphinyl" describes a —PRxRy group, with Rx and Ry as defined hereinabove.

The term "silyloxy" describes a —O—Si-RwRqRz, with Rw, Rq and Rz being alkyl, cycloalkyl, halogen, alkoxy, thioalkoxy, aryl, hydroxy, thiol and thioaryloxy.

The carboxylic group (represented by X—W(=Y)—Z in Formula I hereinabove) can be further substituted by one or more derivatizing groups (as is represented in Formula I hereinabove as a second derivatizing group). Such derivatizing groups can be, for example, halogen, alkyl, haloalkyl, hydroxyalkyl, cycloalkyl, heteroalicyclic, aryl, heteroaryl, carboxy, hydroxy, alkoxy, aryloxy, carbonyl, thioalkoxy, thiohydroxy, thioaryloxy, thiocarboxy, thiocarbonyl, sulfinyl, sulfonyl, amino, alkylamino, carbamyl, nitro and cyano, as these terms are defined hereinabove. Alternatively, $R^5$ and $R^6$ can together form a five- or six-membered ring, such as, for example, cycloalkyl, heteroalicyclic, phenyl or heteroaryl, as these terms are defined hereinabove.

Chemical Syntheses:

According to another aspect of the present invention, there is provided a method for synthesizing the compounds described herein.

The method, according to this aspect of the present invention, is effected by coupling an 4-anilinoquinazoline derivatized by $R^a$, A, B, C and D, as described hereinabove, and substituted at the quinazoline ring by a first and a second reactive groups, with a polyalkylene glycol derivatized by R', R'', R''' and V and substituted by a third reactive group that is capable of reacting with the second reactive group, to thereby produce an 4-anilinoquinazoline substituted by the first reactive group and further by the polyalkylene glycol; and reacting the obtained substituted 4-anilinoquinazoline with a reactive carboxylic derivative that comprises the group Z, as described herein, at the α position.

As used herein, the term "reactive" with respect to a group or a derivative refers to a group or derivative which can be easily reacted with another group, so as to form a chemical bond, preferably a covalent bond, or can be easily chemically modified so as to produce a new functional group, which in turn can be easily reacted so as to form a bond or serves to provide the compound with desired features. Representative examples of reactive groups that are suitable for use in the context of the present invention include, without limitation, nitro, amino, hydroxy, alkoxy, aryloxy, thiol, thiohydroxy, silyloxy, sulfonyl, sulfinyl and halogen. Additional examples are described in the Examples section that follows. A carboxylic acid chloride is a representative example of a reactive carboxylic derivative.

The various reactive groups are selected capable of interacting with one another so as to form a bond therebetween, either directly, or upon being converted to another functional or reactive group. Thus, for example, the second reactive group and the third reactive group are selected capable of interacting with one another so as to form covalent bond linking the polyalkylene glycol moiety to the 4-anilinoquinazoline. Similarly, the reactive carboxylic derivative is selected capable of interacting with the first reactive group, so as to attach the carboxylic moiety to the quinazoline ring.

As described hereinabove, in preferred embodiments of the present invention, the X—W(=Y)—Z group is at position 6 or 7, preferably at position 6. Hence, the first reactive group of the quinazoline ring is at position 6 or 7 of the 4-anilinoquinazoline, preferably at position 6.

As further described hereinabove, in preferred embodiments of the present invention, the polyalkylene glycol moiety is attached at position 6 or 7 of the quinazoline ring, preferably at position 7. Hence, the second reactive group is preferably at position 6 or 7 of the 4-anilinoquinazoline, preferably at position 7.

As further discussed hereinabove, in preferred embodiments of the present invention, the carboxylic moiety is attached to the quinazoline ring via an amide bond, formed between the reactive carboxylic derivative and the amine reactive group at the quinazoline ring.

The amine group can be generated by reduction of a nitro reactive group, such that according to a preferred embodiment of the present invention, the first reactive group is a nitro group, and the method further comprising, prior to the reaction with the carboxylic reactive derivative, reducing an 4-anilinoquinazoline substituted by a nitro group and by the polyalkylene glycol moiety, to thereby produce a an 4-anilinoquinazoline substituted by an amino group and further the polyalkylene glycol moiety.

Other methods for attaching a reactive carboxylic derivative to the quinazoline ring are described, for example, in Smaill et al., 2000, U.S. Pat. No. 6,562,319 and in WO 04/064718.

The 4-anilinoquinazoline, derivatized by $R^a$, A, B, C and D, is typically prepared by coupling an aniline derivatized by the $R^a$, A, B, C and D described hereinabove with a 4-chloroquinazoline, which is optionally substituted by one or more reactive group(s), as described, for example, in U.S. Pat. No. 6,562,319, U.S. Patent Application No. 2004/0265228 and WO 04/064718. The 4-chloroquinazoline can therefore be selected or prepared so as to have the first and/or the second reactive groups, or, alternatively, the first and/or the second reactive groups are generated upon said coupling.

The third reactive group, in the reactive derivative of a selected polyalkylene glycol, can form a part of the polyalkylene glycol itself, namely, be, for example, hydroxy, amino or thiol, or, optionally and preferably, can be generated by converting these groups to more reactive groups, as is described in detail in the Examples section that follows.

An exemplary synthetic pathway for producing representative examples of the compounds described herein is presented in FIG. 3.

The Biochemistry:

As is demonstrated in the Examples section that follows, representative examples of the novel compounds of the present embodiments were tested for their binding to EGFR and showed high affinity toward EGFR and substantial irreversible binding thereto. These compounds can therefore efficiently serve for treating diseases or disorders in which inhibiting the activity of EGFR-TK is beneficial.

Hence, according to another aspect of the present invention, there is provided a method of treating an EGFR-TK related disease or disorder. The method according to this aspect of the present invention is effected by administering to a subject in need thereof a therapeutically effective amount of a compound as described herein, either per se, or, more preferably, as a part of a pharmaceutical composition, mixed with, for example, a pharmaceutically acceptable carrier, as is detailed hereinunder.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound or a compound according to the present embodiments and a target EGFR together in such a manner that the compound can affect the catalytic activity of the EGFR-TK either directly; i.e., by interacting with the kinase itself or indirectly; i.e., by interacting with another molecule on which the catalytic activity of the kinase is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this method of the present invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one having ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

Further according to the present invention, there is provided a use of any of the compounds described herein as a medicament, whereby the medicament is preferably for treating an EGFR-TK related disease or disorder.

As used herein, "EGFR-TK related disease or disorder" describes a disease or disorder characterized by inappropriate EGFR-TK activity or over-activity of the EGFR-TK. Inappropriate activity refers to either; (i) EGFR-TK expression in cells which normally do not express EGFR-TKs; (ii) increased EGFR-TK expression leading to unwanted cell proliferation, differentiation and/or growth; or, (iii) decreased EGFR-TK expression leading to unwanted reductions in cell proliferation, differentiation and/or growth. Over-activity of EGFR-TKs refers to either amplification of the gene encoding a particular EGFR-TK or production of a level of EGFR-TK activity which can correlate with a cell proliferation, differentiation and/or growth disorder (that is, as the level of the EGFR-TK increases, the severity of one or more of the symptoms of the cellular disorder increases). Over activity can also be the result of ligand independent or constitutive activation as a result of mutations such as deletions of a fragment of EGFR-TK responsible for ligand binding.

Preferred diseases or disorders that the compounds described herein may be useful in preventing, treating and studying are cell proliferative disorders, such as, but not limited to, papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, hepatocellular carcinoma, leukemia, lymphoma, Hodgkin's disease and Burkitt's disease.

Hence, further according to the present invention there is provided a method of inhibiting cell proliferation by subjecting the cells to any of the compounds described hereinabove. In a preferred embodiment of the invention the cells are of an organism (e.g., a human), whereas subjecting the cells to the compound is effected in vivo. Alternatively, subjecting the cells to the compound is effected in vitro.

Further according to the present invention, there is provided a use of any of the compounds described herein as a medicament, whereby the medicament is preferably for treating medical conditions in which inhibiting cell proliferation is beneficial.

Radiolabeled Compounds:

As is discussed hereinabove, and is further described hereinbelow, irreversible EGFR-TK inhibitors are particularly useful in diagnostic applications such as radioimaging. The novel compounds according to the present embodiments were therefore designed so as to allow radiolabeling thereof at various positions by various radioisotopes. As is exemplified in the Examples section that follows, representative examples of radiolabeled compounds according to the present invention were successfully prepared. The attachment of the polyalkylene glycol moiety advantageously allows, if desired, to perform shorter radiosyntheses by introducing a radiolabeled group at late stages of the synthetic pathway, thus resulting in high radiochemical yield and purity of the obtained radiolabeled compounds.

Hence, according to another aspect of the present invention there is provided a radiolabeled compound, which comprises a first moiety and a second moiety covalently linked therebetween, wherein the first moiety is selected from the group consisting of a radiolabeled polyalkylene glycol and a non-radiolabeled polyalkylene glycol and the second moiety has the general Formula I*:

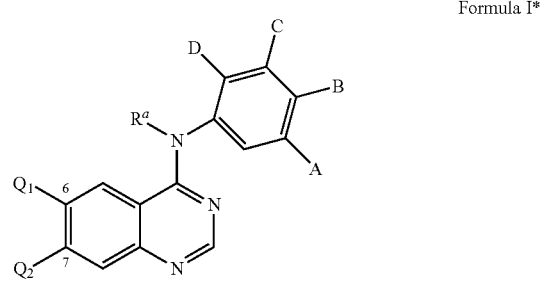

Formula I* wherein:

Q1 is X—W(=Y)—Z and Q2 is selected from the group consisting of hydrogen, halogen, alkoxy, hydroxy, thiohydroxy, thioalkoxy, alkylamino and amino or absent, or Q1 is selected from the group consisting of hydrogen, halogen, alkoxy, hydroxy, thiohydroxy, thioalkoxy, alkylamino and amino or absent and Q2 is X—W(=Y)—Z;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;

W is selected from the group consisting of a non-radioactive carbon and a radioactive carbon;

Y is selected from the group consisting of oxygen and sulfur;

Z is selected from the group consisting of —R$^2$C=CHR$^3$, —C≡C—R$^3$, —R$^2$C=C=CHR$^3$ and —CR$^4$R$^5$R$^6$;

R$^a$ is selected from the group consisting of hydrogen or alkyl having 1-8 carbon atoms;

A, B, C and D are each independently selected from the group consisting of hydrogen, a first non-radioactive derivatizing group and a first radioactive derivatizing group selected from a radioactive bromine, a radioactive iodine and a radioactive fluorine;

R$^1$ is selected from the group consisting of hydrogen, and substituted or non-substituted alkyl having 1-6 carbon atoms;

R$^2$ is selected from the group consisting of hydrogen, halogen and alkyl having 1-6 carbon atoms;

R$^3$ is selected from the group consisting of hydrogen, halogen, carboxy, alkenyl, alkoxy, carbonyl, substituted or non-substituted alkyl having 1-6 carbon atoms, substituted or non-substituted phenyl and substituted or non-substituted alkyl having 1-6 carbon atoms in which at least one of said carbon atoms is a radioactive carbon;

R$^4$ is a leaving group; and

R$^5$ and R$^6$ are each independently selected from the group consisting of hydrogen and a second derivatizing group, whereby the compound comprises at least one radioactive atom.

As used herein, the phrases "radiolabeled compound" or "radioactive atom" (type specified or not) refer to a compound that comprises one or more radioactive atoms or to a radioactive atom with a specific radioactivity above that of background level for that atom. It is well known, in this respect, that naturally occurring elements are present in the form of varying isotopes, some of which are radioactive isotopes. The radioactivity of the naturally occurring elements is a result of the natural distribution of these isotopes, and is commonly referred to as a background radioactive level. However, there are known methods of enriching a certain element with isotopes that are radioactive. The result of such enrichment is a population of atoms characterized by higher radioactivity than a natural population of that atom, and thus the specific radioactivity thereof is above the background level.

Thus, the radiolabeled compounds of the present embodiments have a specific radioactivity that is higher than the corresponding non-labeled compounds, and therefore these radiolabeled compounds can be used as agents for radioimaging and radiotherapy.

Furthermore, the term "non-radioactive", as used herein with respect to an atom or a derivatizing group, refers to an atom or a derivatizing group, as this phrase is defined hereinabove, that does not comprise a radioactive atom and thus the specific radioactivity thereof is of a background level.

The term "radioactive", as used herein with respect to an atom or a derivatizing group, refers to an atom or a derivatizing group that comprises a radioactive atom and therefore the specific radioactivity thereof is above the background level.

Preferred radiolabeled compounds according to the present embodiments include the preferred compounds described hereinabove, radiolabeled by one or more of a radioactive carbon, a radioactive fluorine, a radioactive bromine and a radioactive iodine.

The radioactive carbon is preferably carbon-11. The radioactive fluorine is preferably fluorine-18. The radioactive bromine is preferably bromine-76 or bromine-77. The radioactive iodine is preferably iodine-123, iodine-124 or iodine-131.

According to preferred embodiments of the present invention, the radioactive atoms or groups according to the present embodiments can be any one of the derivatizing groups of the aniline ring, namely, A, B, C or D, or, alternatively, can form a part of the carboxylic group (Z—(W=Y)—), as described in detail in U.S. Pat. No. 6,562,319, U.S. Patent Application No. 2004/0265228 and WO 04/064718.

In one preferred embodiment, the radioactive atom is radioactive bromine such as bromine-76 and bromine-77. Preferably, A is the radioactive bromine. A bromine-76 labeled compound can be used for PET radioimaging, while a bromine-77 labeled compound can be used for radiotherapy.

In another preferred embodiment, the radioactive atom is radioactive iodine such as iodine-123, iodine-124 or iodine-131. Preferably, A is the radioactive iodine. An iodine-123 labeled compound can be used for SPECT radioimaging, an iodine-124 labeled compound can be used for both PET radioimaging and/or radiotherapy and an iodine-131 labeled compound can be used for radiotherapy.

The iodine-124 radioisotope is becoming increasingly significant in PET diagnostic use. It decays ($t_{1/2}$=4.2 days) simultaneously by positron emission (25.6%) and by electron capture (74.4%). Due to its quantity of short-range Auger electrons (9.2/decay) it has also been discussed as a potential therapeutic nuclide.

The substantially longer half-life of this isotope, as compared with the other optional radioisotopes considered, enables a prolonged follow up after injection of the radiolabeled agent. Following autophosphorylation of the receptor, it is degraded with a half-life of 20 hours, thus allowing sufficient receptor-inhibitor binding time for imaging.

In another embodiment, at least one of A, B, C and D is a radioactive fluorine, and the radioactive fluorine is fluorine-18. Preferably, D is fluorine-18.

Further according to preferred embodiments of the invention, W is a radioactive carbon, preferably carbon-11. Alternatively, one or more of the derivatizing groups in Z, namely, R$^2$, R$^3$, R$^5$ or R$^6$ is a radioactive derivatizing group, which includes, for example, a radioactive carbon.

In one preferred embodiment, Z is (CH$_3$)$_2$N—CH$_2$—CH=CH—, and a methyl group in the derivatizing dimethylamino group comprises a radioactive carbon, preferably carbon-11.

In addition, the radiolabeled compounds of the present embodiments can include a radioactive atom at the carboxylic side chain (represented by X—W(=Y)—Z in Formula I* above), such that one or more of R$^2$, R$^3$, R$^5$ and R$^6$ is a radioactive derivatizing group, (defined herein as a second radioactive derivatizing group), which includes any of the radioactive atoms described hereinabove. The second derivatizing group can be, for example, a radioactive fluorine (e.g., fluorine-18) labeled, a radioactive bromine (e.g., bromine-76 or bromine-77) labeled, or a radioactive iodine (e.g., iodine-123, iodine-124 or iodine-131) labeled haloalkyl, cycloalkyl (substituted thereby), or aryl (substituted thereby).

According to particularly preferred embodiments of the present invention, the radioactive atom or group forms a part of the polyalkylene glycol moiety such that in the radiolabeled compound described hereinabove the polyalkylene glycol moiety is radiolabeled.

Preferably, the radiolabeled polyalkylene glycol moiety has the general Formula II*:

  Formula II* wherein m, n, U, R' and R" are as defined herein and V is a radioactive third derivatizing group.

Further preferably, V comprises one or more radioactive atom(s) such as a radioactive carbon, a radioactive fluorine, a radioactive bromine and a radioactive iodine, as detailed hereinabove, most preferably a radioactive fluorine.

As is detailed hereinbelow, a novel radiosynthetic route has been designed and successfully practiced for radiolabeling the EGFR-TK inhibitors described herein by fluorine-18 via incorporation of the radioactive fluorine within the polyalkylene moiety. This novel route enables to perform a three-step radiosynthesis instead of the multi-step radiosynthesis previously described for radiolabeling corresponding EGFR-TK inhibitors by fluorine-18.

Radiosyntheses:

According to another aspect of the present invention, there are provided methods for the syntheses of the radiolabeled compounds described herein.

The radiolabeling of the compounds can be performed using five main alternative strategies as follows:

The first strategy involves the incorporation of fluorine-18 atom within the aniline ring and requires that the radiolabeling be the first step of a multi-step radiosynthesis, as is further detailed in the Examples section that follows.

In this strategy, a radiolabeled compound having the general Formula V:

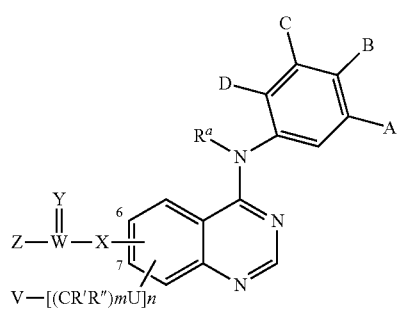

Formula V wherein:

X, Y, Z, $R^a$, $R^1$—$R^6$, m, n, U, R', R" and R'" are as defined herein;

W is carbon; and

A, B, C and D are each independently selected from the group consisting hydrogen, a fluorine-18 and a first derivatizing group, provided that at least one of A, B, C and D is fluorine-18, is prepared by coupling a fluorine-18 labeled 4-anilinoquinazoline derivatized by $R^a$, A, B, C and D as defined hereinabove and substituted at the quinazoline ring by a first and a second reactive groups, with a polyalkylene glycol derivatized by R', R", R'" and V and substituted by a third reactive group capable of reacting with the second reactive group, so as to produce a fluorine-18 labeled 4-anilinoquinazoline substituted by the first reactive group and further by the polyalkylene glycol moiety; and reacting the fluorine-18 labeled 4-anilinoquinazoline substituted by the first reactive group and by the polyalkylene glycol moiety with a reactive carboxylic derivative that comprises Z at the α position.

The general synthetic pathway according to this strategy includes the same procedures as described hereinabove for the non-labeled compounds, while starting from a fluorine-18 labeled aniline.

The second strategy involves the incorporation of radioactive bromine or radioactive iodine within the anilino ring of the 4-(phenylamino)quinazoline, prior to the final step of the synthesis, resulting in an advantageous two-step radiosynthesis.

Thus, according to this strategy, a radiolabeled compound having the general Formula VI:

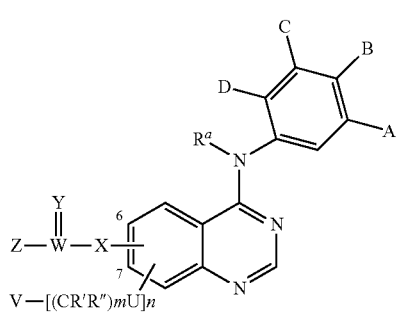

Formula VI wherein:

X, Y, Z, $R^a$, $R^1$—$R^6$, m, n, U, R', R" and R'" are as defined herein;

W is carbon; and

A, B, C and D are each independently selected from the group consisting hydrogen, a radioactive bromine, a radioactive iodine and a first derivatizing group, provided that at least one of A, B, C and D being the radioactive bromine or the radioactive iodine, is prepared by coupling an 4-anilinoquinazoline derivatized by said $R^a$ and by A', B', C' and D', wherein at least one of the A', B', C' and D' is halogen and the others are A, B, C and/or D as previously described, whereby the 4-anilinoquinazoline is substituted at the quinazoline ring by a first and a second reactive groups, with a polyalkylene glycol derivatized by R', R", R'" and V and substituted by a third reactive group capable of reacting with the second reactive group, to thereby produce an 4-anilinoquinazoline derivatized by $R^a$, A', B', C', and D' and substituted by the first reactive group and by the polyalkylene glycol moiety; radiolabeling the 4-anilinoquinazoline derivatized by $R^a$, A', B', C', and D' and substituted by the first reactive group and the polyalkylene glycol moiety with a radioactive bromine or a radioactive iodine, to thereby produce a radioactive bromine labeled or a radioactive iodine labeled 4-anilinoquinazoline derivatized by the $R^a$, A, B, C and D and substituted by the first reactive group and by the polyalkylene glycol moiety; and reacting the radioactive bromine labeled or radioactive iodine labeled 4-anilinoquinazoline substituted by the first reactive group and by the polyalkylene glycol moiety with a reactive carboxylic derivative that comprises Z at the α position.

According to this strategy, the aniline ring is selected so as to have one halogen atom, preferably being A' (corresponding to A in Formula VI above), whereby the other derivatizing groups on the aniline ring, e.g., B', C' and D' are the same as B, C and D in Formula VI. The halogen atom is converted to a radioactive bromine or iodine, as previously described.

The general synthetic pathway according to this strategy includes the same procedures as described hereinabove for the non-labeled compounds, while starting from a suitable halogen-substituted aniline.

The third strategy for radiolabeling according to the present embodiments involves the incorporation of a carbon-11 atom within the α-substituted carboxylic group, which is performed at the final step of the synthesis, thus being an advantageous one-step radiosynthesis.

According to this strategy, a radiolabeled compound having the general Formula VII:

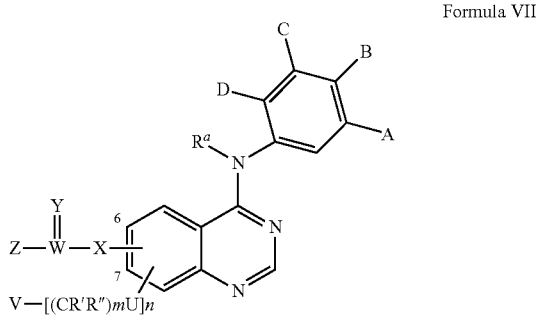

Formula VII wherein:

X is as defined herein;

W is a non-radioactive carbon or carbon-11;

Y and Z are as defined herein;

$R^a$, A, B, C and D, $R^1$ and $R^2$ are as defined herein;

$R^3$ is selected from the group consisting of hydrogen, halogen, carboxy, alkenyl, alkoxy, carbonyl, a substituted or non-substituted alkyl having 1-6 carbon atoms, a substituted or non-substituted phenyl and a substituted or non-substituted alkyl having 1-6 carbon atoms, at least one carbon atom being carbon-11;

$R^4$ is a leaving group;

$R^5$ and $R^6$, m, n, U, V and R', R" and R'" are as defined herein, whereby the compound comprises at least one carbon-11 atom, is prepared by coupling an 4-anilinoquinazoline derivatized by the $R^a$, A, B, C and D and substituted at the quinazoline ring by a first and a second reactive groups, with a polyalkylene glycol substituted by a third reactive group capable of reacting with the second reactive group, to thereby produce an 4-anilinoquinazoline substituted by the first reactive group and further by the polyalkylene glycol moiety; and reacting the 4-anilinoquinazoline substituted by the first reactive group and the polyalkylene glycol moiety with a reactive carboxylic derivative that comprises the Z at the α position and at least one carbon-11 atom.

The general synthetic pathway according to this strategy includes the same procedures as described hereinabove for the non-labeled compounds, whereby the final step involves incorporation of a carbon-11 to the carboxylic group.

The incorporation of carbon-11 to the carboxylic group can be performed by directly reacting a carbon-11 labeled carboxylic derivative having a fourth reactive group, or alternatively, can be performed subsequent to the reacting with the carboxylic derivative, by introducing a carbon-11 derivatizing group to the carboxylic side chain, as previously described (see, for example, U.S. Patent Application having the publication No. 20020128553).

The fourth strategy involves incorporation of a radioactive fluorine (e.g., fluorine-18), a radioactive bromine, a radioactive iodine or a radioactive carbon (e.g., carbon-11) within the polyalkylene glycol moiety, which is performed prior to the two final steps of the synthesis and hence advantageously involves a three-step radiosynthesis.

According to this strategy, a radiolabeled compound having the general Formula VIII:

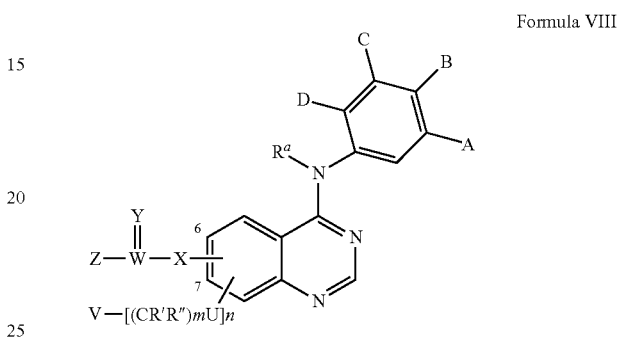

Formula VIII wherein:

X, W, Y and Z are as defined herein;

$R^a$, A, B, C and D, $R^1$—$R^6$, m, n, U, R', R" and R'" are as defined herein; and V is a radioactive third derivatizing group, is prepared by coupling an 4-anilinoquinazoline derivatized by the $R^a$, A, B, C and D and substituted at the quinazoline ring by a first and a second reactive groups, with a polyalkylene glycol derivatized by the R', R" and R'" and by V' and substituted by a third reactive group capable of reacting with the second reactive group, wherein the V' is a fifth reactive group, to thereby produce an 4-anilinoquinazoline substituted by the first reactive group and by the polyalkylene glycol moiety derivatized by the fifth reactive group; converting the fifth reactive group into a radioactive group, to thereby produce a radiolabeled 4-anilinoquinazoline substituted by the first reactive group and further by the polyalkylene glycol moiety derivatized by the radioactive group; and reacting the radiolabeled 4-anilinoquinazoline substituted by the first reactive group and the polyalkylene glycol moiety derivatized by the radioactive group with a reactive carboxylic derivative that comprises the Z at the α position.

The general synthetic pathway according to this strategy includes the same procedures as described hereinabove for the non-labeled compounds, whereby the polyalkylene glycol is selected so as to include a V' group that is capable of being converted to a radioactive group.

In one example, V' is sulfonyl, a highly reactive group that can be readily substituted by fluorine-18.

While practicing the radiosynthesis presented in the fourth strategy hereinabove, it has now been surprisingly found that incorporation of a radiolabeled atom within the polyalkylene glycol moiety can be advantageously effected in a one-step radiosynthesis and hence a fifth radiosynthetic approach can be practiced. The fifth and presently most preferred strategy involves incorporation of a radioactive fluorine (e.g., fluorine-18), a radioactive bromine, a radioactive iodine or a radioactive carbon (e.g., carbon-11) within the polyalkylene glycol moiety, which is performed as the final step of the synthesis and hence advantageously involves a one-step radiosynthesis.

According to this strategy, a radiolabeled compound having the general Formula VIII:

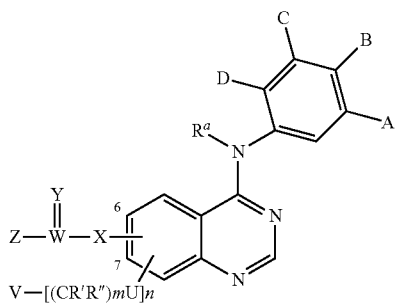

Formula VIII wherein:

X, W, Y and Z are as defined herein;

$R^a$, A, B, C and D, $R^1$—$R^6$, m, n, U, R', R" and R'" are as defined herein; and V is a radioactive third derivatizing group, is prepared by coupling an 4-anilinoquinazoline derivatized by the $R^a$, A, B, C and D and substituted at the quinazoline ring by a first and a second reactive groups, with a polyalkylene glycol derivatized by the R', R" and R'" and by V' and substituted by a third reactive group capable of reacting with the second reactive group, wherein the V' is a fifth reactive group, to thereby produce an 4-anilinoquinazoline substituted by the first reactive group and by the polyalkylene glycol moiety derivatized by the fifth reactive group; reacting the 4-anilinoquinazoline derivatized by the $R^a$, A, B, C and D and substituted by the first reactive group and the polyalkylene glycol moiety derivatized by the fifth reactive group with a reactive carboxylic derivative that comprises the Z at the α position; and converting the fifth reactive group into a radioactive group, to thereby produce a radiolabeled 4-anilinoquinazoline substituted by the first reactive group and further by the polyalkylene glycol moiety derivatized by the radioactive group.

The general synthetic pathway according to this strategy includes the same procedures as described hereinabove for the non-labeled compounds, whereby the polyalkylene glycol is selected so as to include a V' group that is capable of being converted to a radioactive group.

In one example, V' is sulfonyl, a highly reactive group that can be readily substituted by fluorine-18.

Thus, it has been shown that introducing a polyalkylene glycol moiety to the 4-anilinoquinazoline compounds described herein can be further advantageously utilized for enabling to perform radiolabeling of these compounds while utilizing an efficient, one-step radiosynthesis.

General and detailed exemplary radiosynthesis procedures, based on the strategies above, are described in the Examples section that follows.

As is demonstrated in the Examples section that follows, using these strategies, representative examples of fluorine-18 labeled compounds according to the present embodiments have been successfully radiosynthesized.

Radioimaging and Radiotherapy:

The radiolabeled compounds herein described can be used as radioimaging and radiotherapy agents. Carbon-11 labeled, fluorine-18 labeled, bromine-76 labeled and iodine-124 labeled compounds can be used, for example, as biomarkers for PET radioimaging, whereas iodine-123 labeled compounds can be used as biomarkers for SPECT radioimaging. Bromine-77 labeled, iodine-124 and iodine-131 labeled compounds can be used as radiopharmaceuticals for radiotherapy. Thus, the radiolabeled compounds described herein can be used to effect a method of monitoring the level of epidermal growth factor receptor within a body of a patient by administering to the patient any of the carbon-11, fluorine-18, bromine-76, iodine-123 or iodine-124 radiolabeled compounds described herein and employing a nuclear imaging technique, such as positron emission tomography or single photon emission computed tomography, for monitoring a distribution of the compound within the body or within a portion thereof.

Nuclear imaging dosing depends on the affinity of the compound to its receptor, the isotope employed and the specific activity of labeling. Persons ordinarily skilled in the art can easily determine optimum nuclear imaging dosages and dosing methodology.

The bromine-77, iodine-124 and iodine-131 radiolabeled compounds herein described can be used to effect a method of radiotherapy by administering to a patient a therapeutically effective amount, as is defined hereinabove, of a radiolabeled compound as described herein, either per se, or, preferably in a pharmaceutical composition, mixed with, for example, a pharmaceutically acceptable carrier.

Pharmaceutical Compositions:

Any of the compounds described herein, non-labeled and radiolabeled, can be formulated into a pharmaceutical composition which can be used as a medicament for treating a disease or disorder (e.g., cancer therapy), as a medicament for radiotherapy or as a diagnostic agent for imaging. Such a composition includes as an active ingredient any of the compounds described herein and a pharmaceutically acceptable carrier.

As used herein a "pharmaceutical composition" refers to a preparation of one or more of the compounds described herein, with other chemical components such as pharmaceutically suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition.

Routes of administration: Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Composition/formulation: Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which, can be used pharmaceutically. Proper formulation is dependent upon the route of administration chosen.

For injection, the compounds described herein may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the compounds described herein can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds described herein are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile, pyrogen-free water, before use.

The compounds described herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

The pharmaceutical compositions of the present invention may, if desired, be presented in a pack or dispenser device, such as an FDA approved kit, which may contain one or more unit dosage forms containing the active ingredient (the compounds described herein). The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a compound as described herein formulated in a compatible pharmaceutical carrier may also be prepared, placed in an appropriate container, and labeled for treatment of an indicated condition. Suitable conditions indicated on the label may include treatment of cell proliferation disease or disorder such as certain cancers associated with EGFR-TK activity, and radioimaging.

Hence, according to a preferred embodiment of the present invention, the pharmaceutical composition described hereinabove is packaged in a packaging material and identified in print, in or on the packaging material for use in the treatment of an EGFR-TK related disease or disorder, as is described hereinabove, or as a diagnostic agent for radioimaging.

Based on the advantageous effect of incorporating a polyalkylene glycol moiety within a 4-anilinoquinazoline compound as described herein, other moieties that can similarly enhance the solubility, biostability and bioavailability of these compounds can also be introduced thereto. Preferred moieties that can be advantageously utilized in this regard include, for example, hydroxy-containing moieties, thiohydroxy-containing moieties, amino-containing moieties and the like. Such moieties can affect (e.g., decrease) the lipophilicity of the obtained compounds and thus result, for example, in compounds which are characterized by reduced lipophilicity (Log P), enhanced solubility in e.g., body fluids and hence by improved pharmacokinetic characteristics.

As used herein, the term "hydroxy-containing moiety" describes a chemical moiety that comprises one or more free hydroxyl group. Examples include, but are not limited to, a hydroxy group per se, a hydroxyalkyl, as defined herein, a hydroxyalkenyl, a hydroxyalkynyl, and a polyalkylene glycol moiety, as defined herein.

As used herein, the term "thiohydroxy-containing moiety" describe a chemical moiety that comprises one or more free hydroxyl group. Examples include a thiohydroxy group per se, a thiohydroxyalkyl, as defined herein, a thiohydroxyalkenyl, a thiohydroxyalkynyl, and a thio-polyalkylene glycol moiety, as defined herein.

As used herein, the term "amino-containing moiety" describe a chemical moiety that comprises one or more free hydroxyl group. Examples include an amine group per se, an aminoalkyl, as defined herein, an aminoalkenyl, an aminoalkynyl, and an amino polyalkylene glycol moiety, as defined herein.

Thus, further according to the present embodiments there are provided compounds having the general formula I described herein and one or more hydroxy-containing moieties as described herein.

These compounds can thus include one hydroxy-containing moiety or, optionally and preferably, two or more hydroxy-containing moieties being the same or different.

In one embodiment of this aspect of the present invention, the compound comprises at least two hydroxy-containing moieties, at least one being a hydroxyalkyl group and at least one being a polyalkylene moiety, as defined herein. Such compounds can be advantageously utilized for providing radiolabeled compounds, by radiolabeling the polyalkylene glycol moiety via an advantageous radiosynthetic route as described herein, while further exhibiting the desired solubility, biostability and bioavailability, exhibited by the additional hydroxyalkyl group(s).

The hydroxy-containing moiety or moieties can be attached to any available and chemically compatible position of the 4-anilinoquinazoline compound, and preferably to any of positions 5 to 8 of the quinazoline ring. The hydroxy-containing moiety or moieties can thus also form a part of other substituents on the quinazoline ring.

In one preferred embodiment, a hydroxy-containing moiety forms a part of the X—W(=Y)—Z group (see, Q1 or Q2 in the Formulae hereinabove). For example, when Z is —$R^2C$=$CHR^3$, $R^3$ is an alkyl substituted by an amino group and the amino group is further substituted by one or more hydroxyalkyl groups. Such a compound can further comprise a polyalkylene glycol moiety attached thereto, preferably at position 7, as depicted in the Examples section that follows and further exemplified in FIG. 9.

The compounds described in these embodiments can further be radiolabeled as described herein and advantageously utilized in therapeutic and imaging applications, as described herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Chemical Syntheses

Materials and methods:

All chemicals were purchased from Sigma-Aldrich, Fisher Scientific, Merck or J. T. Baker. Chemicals were used as supplied, excluding THF, which was refluxed over sodium and benzophenone and was freshly distilled prior to use.

Mass spectroscopy was performed in EI mode on a Thermo Quest—Finnigan Trace MS-mass spectrometer at the Hadassah-Hebrew University Mass Spectroscopy Facility.

NMR measurements were performed on a Bruker AMX 300 MHz apparatus, using the hydrogenated residue of the deuterated solvents (DMSO-$d_6$, $\delta$=2.5 ppm, $CDCl_3$, $\delta$=7.25 ppm) and TMS as an internal standard for $^1$H-NMR.

Elemental analysis was performed at the Hebrew University Microanalysis Laboratory.

Thin-layer chromatography (TLC) was run on plates of silica gel 60$F_{254}$ (Merck). The compounds were localized at 254 nm using a UV lamp.

HPLC analyses were performed on a reversed-phase system using Waters μBondapak® C-18 analytical and semi-preparative columns, with a mobile phase system composed of 45:35 (v/v) acetonitrile:acetate buffer 0.1 M pH 3.8. Separations were carried out using a Varian 9012Q pump, a Varian 9050 variable wavelength detector operating at 254 nm, and a Bioscan Flow-Count radioactivity detector with a NaI crystal. Specific radioactivities were determined by HPLC, using cold mass calibration lines.

Preparation of (4-anilinoquinazolinyl)amides Substituted by a Polyalkylene Glycol Moiety—General Synthetic Pathway The general synthetic pathway for preparing the compounds described herein is presented is Scheme 1 below. Substituted or non-substituted 4-anilinoquinazoline derivatized at the quinazoline ring by a first and a second reactive groups (L and G, respectively, in Scheme 1), preferably at the 6 and 7 positions, is coupled to a reactive derivative of a polyalkylene glycol having a third reactive group (T in Scheme 1) and optionally a derivatizing (also referred to herein as functional) group (V is Scheme 1), preferably in the presence of a base. The third reactive group is selected capable of reacting with the second reactive group substituting the quinazoline. The obtained compound is thereafter reacted with a reactive derivative of a carboxylic acid (ZW (=Y)M in Scheme 1), wherein M is a fourth reactive group that is capable of reacting with the first reactive group substituting the quinazoline, to thereby obtain the desired compound. The variables presented in Scheme 1 are as defined herein.

Scheme 1

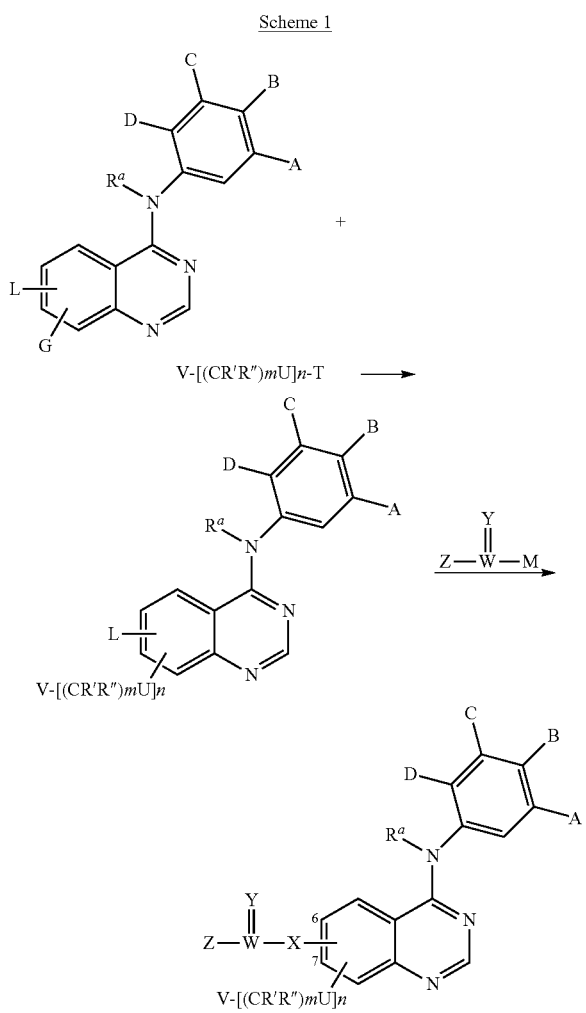

Preparation of Reactive Derivatives of Polyalkylene Glycols—General Procedure Reactive derivatives of polyalkylene glycols, having the general Formula IV below:

T-[U(CR'R")m]nV      Formula IV wherein U, V, R', R", m and n are as defined herein and T is a reactive group (referred to herein as a third reactive group), are prepared by converting a functional group (e.g., hydroxy, thiol, amine) of a corresponding polyalkylene glycol into a reactive group, using well-known procedures.

In one example, a dichloromethane (DCM) solution of a polyalkylene glycol having a hydroxy or thiol functional group is reacted with NaH and then with di-vinylsulfone (molar ratios: OH 1: NaH 5: divinyl sulfone 50, at 0.2 gram PEG/ml DCM), to obtain PEG-vinylsulfone.

In another example, a DCM solution of polyalkylene glycol having a hydroxy or thiol functional group is reacted with acryloyl chloride and triethylamine (molar ratios: OH 1: acryloyl chloride 1.5: triethylamine 2, at 0.2 gram PEG/ml DCM), to obtain PEG-acrylate.

PEG derivatives such as N-hydroxysuccinimide (NHS) esters of PEG carboxylic acids, monomethoxyPEG$_2$-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide are commercially available at various molecular weights [See, e.g., Catalog, Polyethylene Glycol and Derivatives, 2000 (Shearwater Polymers, Inc., Huntsvlle, Ala.)]. If desired, many of the above derivatives are available in a monofunctional monomethoxyPEG (MPEG) form.

In the presently most preferred example, a polyethylene glycol having a hydroxy functional group is reacted with tert-butyldimethylsilyl chloride, in the presence of a base (e.g., imidazole), in a polar solvent (e.g., DMF), as depicted in Scheme 2 below.

Scheme 2

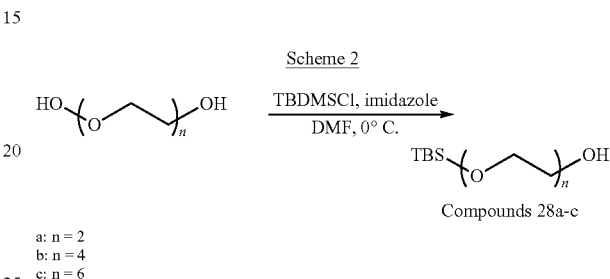

a: n = 2
b: n = 4
c: n = 6

Compounds 28a-c

Preparation of 2-[2-(tert-Butyl-dimethyl-silanyloxy)-ethoxyl-ethanol (Compound 28a)

A solution of imidazole (2.11 grams, 31 mmol) and diethylene glycol (5 grams, 47 mmol) in dry DMF (11 ml) was cooled to 0° C. and stirred for 30 minutes under argon atmosphere. A solution of tert-butyldimethylsilyl chloride (4.72 grams, 31 mmol) in dry DMF (15 ml) was added dropwise and the resulting mixture was maintained for 2 hours at 0° C. and was then allowed to warm up to room temperature. Water (180 ml) was thereafter added and the resulting solution was extracted with ethyl acetate (4×80 ml). The combined organic extracts were washed with brine, the solvent was removed under reduced pressure and the crude product was purified by silica gel chromatography, using ethyl acetate as eluent, to give the product (Compound 28a) as a white oil (4.65 grams, 45% yield).

$^1$H-NMR (CDCl$_3$): δ=3.7-3.78 (m, 4H), 3.53-3.63 (m, 4H), 0.9 (s, 9 H), 0.07 (s, 6 H) ppm.

MS: m/z=221.47 [MH$^+$].

Preparation of 2-{2-[2-(2-(tert-Butyl-dimethyl-silanyloxy)-ethoxy]-ethoxy}-ethoxy)-ethanol (Compound 28b)

Compound 28b was prepared according to the procedure described hereinabove for Compound 28a, using tetraethylene glycol (6 grams, 30 mmol), TBDMSCl (3 grams, 20 mmol), and imidazole (1.4 grams, 20 mmol) in DMF (24 ml), yielding 3.79 grams of the product (41% yield).

$^1$H-NMR (CDCl$_3$): δ=3.53-3.78 (m, 16H), 0.9 (s, 9H), 0.058 (s, 6H) ppm.

MS: m/z=309.05 [MH$^+$].

Preparation of 2-[2-(2-{2-[2-(2-(tert-Butyl-dimethyl-silanyloxy)-ethoxy]-ethoxy}-ethoxy)-ethoxy}-ethoxy]-ethanol (Compound 28c)

Compound 28c was prepared according to the procedure described hereinabove for Compound 6a, using hexaethylene glycol (5 grams, 17.7 mmol), TBDMSCl (1.65 grams, 11 mmol), and imidazole (0.748 grams, 11 mmol) in DMF (26 ml), yielding 1 gram of the product (14% yield).

$^1$H-NMR (CDCl$_3$): δ=3.49-3.7 (m, 24H), 0.83 (s, 9H), 0.045 (s, 6H) ppm.

MS: m/z=420.73 [M$^+$Na].

Preparation of 4-chloro-6-nitroquinazolines Derivatized by a Reactive Group (a Reactive Derivative of 4-chloroquinazoline)—General Procedure 4-Chloro-6-nitroquinazoline substituted by a reactive group is obtained according to the procedure described in Mishani et al. (2005), as depicted in Scheme 3 below:

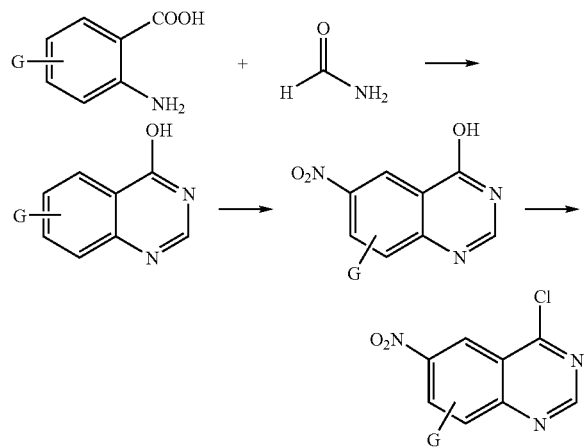

Scheme 3

In brief, 2-aminobezoic acid substituted by a reactive group (G in Scheme 3), is reacted with formamide, at 160° C., for 3 hours. The resulting 4-hydroxyquinazolinesubstituted by the reactive group is then reacted with a mixture of nitric acid and sulfuric acid, to thereby obtain 4-hydroxy-6-nitro-quinazoline substituted by the reactive group. The reactive 4-hydroxy-6-nitroquinazoline is thereafter reacted with thionyl chloride, so as to obtain 4-chloro-6-nitroquinazoline substituted by a reactive group. In these compounds, the nitro group serves as a first reactive group and G is a second reactive group.

Preparation of 4-chloro-7-fluoro-6-nitroquinazoline (Compound 24)

4-Chloro-7-fluor-6-nitroquinazoline was prepared as described in Mishani et al. (2005). In brief, 2-amino-4-fluorobezoic acid was reacted with formamide, at 160° C. for 3 hours. The resulting 7-fluoro-4-hydroxyquinazoline (Compound 22) was then reacted with a mixture of nitric acid and sulfuric acid, at 100° C., for 2 hours, to thereby obtain 7-fluoro-4-hydroxy-6-nitroquinazoline (Compound 23), which was thereafter reacted with thionyl chloride in DMF (reflux, 7 hours), to obtain 4-chloro-fluoro-6-nitroquinazoline (Compound 24, see, FIG. 3).

Preparation of 4-anilino-6-nitroquinazoline (Reactive Derivative of 4-anilinoquinazoline) Substituted by a Reactive Group—General Procedure Aniline or substituted aniline (1 equivalent) is reacted with 4-chloro-6-nitroquinazoline substituted by a reactive group (3.5 equivalents), prepared as described hereinabove, in a polar solvent such as iso-propylalcohol. The product, 6-nitro-4-(phenylamino)quinazoline, substituted by a reactive group and optionally substituted at the aniline ring, is obtained after filtration.

Preparation of 4-[(3,4-dichloro-6-fluoro-phenyl) amino]-7-fluoro-6-nitroquinazoline (Compound 25)

Compound 25 was prepared as described in Mishani et al. (2005). In brief, 3,4-Dichloro-6-fluoroaniline (1 equivalent, prepared as described in U.S. Pat. No. 6,126,917) was reacted with 4-chloro-7-fluoro-6-nitroquinazoline (3.5 equivalents, Compound 24, prepared as described hereinabove), in a mixture of iso-propylalcohol/dichloromethane. After filtration, 4,5-dichloro-2-fluoro-phenyl-(7-fluoro-6-nitro-quinazolin-4-yl)-amine was obtained.

Preparation of 4-[(3-iodophenyl)amino]-7-fluoro-6-nitroquinazoline (Compound 26)

4-chloro-7-fluoro-6-nitroquinazoline (Compound 24, prepared as described hereinabove) and 3-iodoaniline are reacted as described hereinabove for Compound 25, to thereby yield Compound 26.

Preparation of 4-[(3-bromophenyl)amino]-7-fluoro-6-nitroquinazoline (Compound 27)

4-chloro-7-fluoro-6-nitroquinazoline (Compound 24, prepared as described hereinabove) and 3-bromoaniline are reacted as described hereinabove for Compound 25, to thereby yield Compound 27.

Conjugation of a Reactive Polyalkylene Glycol to 4-anilino-6-nitroquinzoline Substituted by a Reactive Group—General Procedure A reactive derivative of polyalkylene glycol (1.5 equivalents), prepared as described hereinabove, is reacted with a 4-anilino-6-nitroquinazoline substituted by a reactive group (1 equivalent), prepared as described hereinabove, in a dry polar solvent such as DMSO, in the presence of a base (3 equivalents), under nitrogen atmosphere at room temperature, as depicted in Scheme 1 above.

Preparation of 2-{2-[4-(4,5-Dichloro-2-fluoro-phenylamino)-6-nitro-quinazoline-7-yloxy]-ethoxy}-ethanol (Compound 29a)

(4,5-Dichloro-2-fluoro-phenyl-(7-fluoro-6-nitro-quinazolin-4-yl)-amine (Compound 25, 0.723 grams, 1.94 mmol), 2-[2-(tert-butyl-dimethyl -silanyloxy)-ethoxy]-ethanol (Compound 28a (0.64 grams, 2.9 mmol) and potassium trimethylsilanolate (0.75 gram, 5.83 mmol) were dissolved in dry DMSO (42 ml) and the resulting mixture was stirred under nitrogen atmosphere for 5 hours at 25° C. The obtained deep crimson mixture was thereafter extracted with ethyl acetate (EtOAc) and water, and the organic phase was washed with NaHCO$_3$ (4%) and brine, and dried over Na$_2$SO$_4$. The solvent was then removed under reduced pressure and the residue was purified by silica gel column chromatography, using a mixture of 2% MeOH in CH$_2$Cl$_2$ as eluent, to obtain Compound 29a (0.217 gram, 24% yield).

$^1$H-NMR (DMSO): δ=10.26 (s, 1H), 9.14 (s, 1H), 8.58 (s, 1H), 7.92 (m, 1H), 7.84 (d, 1H, J=9.6 Hz), 7.52 (s, 1H), 4.6 (m, 1H), 4.42 (m, 2H), 3.8 (m, 2H), 3.49 (m, 3H) ppm.

MS: (m/z)=457.6 [MH⁺].

HR-MS (EI): calculated for $C_{18}H_{15}Cl_2FN_4O_5$: 457.0476, found: 457.0482.

Melting point=149° C.

Preparation of 2-{2-[2-(2-[4-(4,5-Dichloro-2-fluoro-phenylamino)-6-nitro-quinazoline-7-yloxy]-ethoxy]-ethoxy}-ethoxy)-ethanol (Compound 29b):

Compound 29b was prepared as described hereinabove for Compound 29a, using Compound 25 (0.247 gram, 0.8 mmol), 2-{2-[2-(2-(tert-Butyl-dimethyl-silanyloxy)-ethoxy]-ethoxy}-ethoxy)-ethanol (Compound 28b, 0.37 gram, 1.19 mmol), and potassium trimethylsilonate (0.307 gram, 2.39 mmol), dissolved in DMSO (15 ml). The crude residue was purified by silica gel column chromatography, using a mixture of 3% methanol in dichloromethane as eluent, to obtain Compound 29b (0.181 gram, 42% yield).

¹H-NMR(CDCl₃): δ=8.82 (s, 1H), 8.77 (d, 1H, J=0.9 Hz), 8.47 (s, 1H), 7.65 (s, 1H), 7.45 (s, 1H), 7.36 (d, 1H, J=10.2 Hz), 4.4 (t, 2H, J=4.2 Hz), 3.97 (t, 2H, J=4.5 Hz), 3.58-3.99 (m, 12H) ppm.

MS: (m/z)=546.44 [MH°].

HR-MS (EI): calculated for $C_{22}H_{23}Cl_2FN_4O_7$: 545.0995, found: 545.1006.

Preparation of 2-[2-(2-{2-[2-(2-[4-(4,5-Dichloro-2-fluoro-phenylamino)-6-nitro-quinazoline-7-yloxy]-ethoxy]-ethoxy)-ethoxy}-ethoxy]-ethoxy)-ethanol (Compound 29c)

Compound 29c was prepared as described hereinabove for Compound 29a, using Compound 25 (0.596 gram, 1.6 mmol), 2-[2-(2-{2-[2-(2-(tert-Butyl-dimethyl-silanyloxy)-ethoxy]-ethoxy}-ethoxy)-ethoxy}-ethoxy]-ethanol (Compound 28c, 0.957 gram, 2.4 mmol), and potassium trimethylsilonate (0.621 gram, 4.74 mmol) dissolved in DMSO (37 ml). The crude residue was purified by silica gel column chromatography, using a mixture of 2% methanol in dichloromethane as eluent, to obtain Compound 29c (0.568 gram, 56%).

¹H-NMR(CDCl₃): δ=8.64-8.82 (m, 2H), 8.5-8.55 (m, 1H), 7.46 (s, 1H), 7.34 (d, 1H, J=10.5 Hz), 4.39-4.41 (m, 2H), 3.96-3.98 (m, 2H), 3.58-3.78 (m, 20H) ppm.

MS: (m/z)=635.78 [MH⁺].

HR-MS (EI): calculated for $C_{26}H_{31}Cl_2FN_4O_9$: 633.1522, found: 633.1530.

Preparation of 2-{2-[4-(3-iodophenylamino)-6-nitro-quinazoline-7-yloxy]-ethoxy}-ethanol (Compound 30a), 2-[2-[2-(2-[4-(3-iodophenylamino)-6-nitro-quinazoline-7-yloxy]-ethoxy]-ethoxy}-ethoxy)-ethanol (Compound 30b) and 2-[2-(2-{2-[2-(2-[4-(3-iodophenylamino)-6-nitro-quinazoline-7-yloxy]-ethoxy]-ethoxy)-ethoxy}-ethoxy]-ethoxy)-ethanol (Compound 30c)

Compounds 30a, 30b and 30c are prepared as described hereinabove for Compounds 29a-c, respectively, using Compound 26 as the starting material.

Preparation of 2-{2-[4-(3-bromophenylamino)-6-nitro-quinazoline-7-yloxy]-ethoxy}-ethanol (Compound 31a), 2-{2-[2-(2-[4-(3-bromophenylamino)-6-nitro-quinazoline-7-yloxy]-ethoxy]-ethoxy}-ethoxy)-ethanol (Compound 31b) and 2-[2-(2-{2-[2-(2-[4-(3-bromophenylamino)-6-nitro-quinazoline-7-yloxy]-ethoxy]-ethoxy)-ethoxy}-ethoxy]-ethoxy)-ethanol (Compound 31c)

Compounds 31a, 31b and 31c are prepared as described hereinabove for Compounds 29a-c, respectively, using Compound 27 as the starting material.

Preparation of 4-anilino-6-nitroquinzolines Coupled to a Polyalkylene Glycol Terminating with Fifth Reactive Group—General Procedure 4-Anilino-6-nitroquinzoline substituted by a polyalkylene glycol moiety that is terminating with a functional group (e.g., hydroxy, thiol, amine) is reacted with a compound containing the fifth reactive group, preferably in the presence of a base (large molar excess).

In an example, the fifth reactive group is hydroxy-succinimide and a polyalkylene glycol terminating with an amine group is reacted with succinic anhydride.

In another example, the fifth reactive group is sulfonate and a polyalkylene glycol terminating with a hydroxy or thiol group is reacted with a sulfonyl chloride.

In still another example, the fifth reactive group is fluoro and a polyalkylene glycol terminating with a hydroxy or thiol group is reacted with DAST, as is detailed hereinafter.

Preparation of Methanesulfonic Acid 2-{2-[4-(4,5-Dichloro-2-fluoro-phenylamino)-6-nitro-quinazolin-7-yloxy]-ethoxy}-ethyl ester (Compound 32a)

Compound 29a (0.035 gram, 0.076 mmol) was dissolved in dichloromethane (4.3 ml) and triethylamine (0.032 gram, 3.82 mmol) was added to the resulting solution. Methanesulfonyl chloride (MsCl, 0.025 gram, 0.022 mmol) was then added and the resulting mixture was stirred at room temperature for 3 hours. The mixture was thereafter extracted twice with CH₂Cl₂, washed with brine and dried over sodium sulfate. The crude residue was purified by silica gel column chromatography, using a mixture of 2% methanol in dichloromethane as eluent, to give Compound 32a (0.012 gram, 29% yield).

¹H-NMR(CDCl₃): δ=8.82-8.84 (m, 2H), 8.45 (s, 1H), 7.56 (m, 1H), 7.46 (s, 1H), 7.35 (d, 1H, J=10.2 Hz), 4.38-4.41 (m, 4H), 3.99-4.02 (m, 2H), 3.88-3.99 (m, 2H), 3.06 (s, 3H) ppm.

MS: (m/z)=536.81 [MH⁺].

HR-MS (EI): calculated for $C_{19}H_{17}Cl_2FN_4O_7S$: 535.0215, found: 535.0219.

Preparation of Methanesulfonic Acid 2-[2-(2-{2-[4-(4,5-Dichloro-2-fluoro-phenylamino)-6-nitro-quinazoline-7-yloxy]-ethoxy}-ethoxy)-ethoxy]-ethyl ester (Compound 32b)

Compound 32b was prepared as described hereinabove for Compound 32a, using Compound 29b (0.023 gram, 0.043 mmol), methanesulfonyl chloride (0.014 gram, 0.12 mmol) and triethylamine (0.021 gram, 0.021 mmol) in dichloromethane (2.3 ml), yielding 0.015 gram of the product (55% yield).

¹H-NMR(CDCl₃): δ=8.83 (s, 1H), 8.76 (d, 1H, J=7.8 Hz), 8.48 (s, 1H), 7.65 (s-br, 1H), 7.44 (s, 1H), 7.34 (d, 1H, J=10.5 Hz), 4.33-4.4 (m, 4H), 3.97 (t, 2H, J=4.5 Hz), 3.65-3.77 (m, 10H), 3.06 (s, 3H) ppm.

MS: (m/z)=625.53 [MH⁺].

HR-MS (EI): calculated for $C_{23}H_{25}Cl_2FN_4O_9S$: 623.0725, found: 623.0731.

Preparatin of Methanesulfonic Acid 2-(2-{2-[2-(2-{2-[4-(4,5-Dichloro-2-fluoro-phenylamino)-6-nitro-quinazolin-7-yloxy]-ethoxy}-ethoxy)-ethoxy]-ethoxy}-ethoxy-)-ethyl ester (Compound 32c)

Compound 32c was prepared as described hereinabove for Compound 32a, using Compound 29c (0.067 gram, 0.1 mmol), methanesulfonyl chloride (0.036 gram, 0.32 mmol) and triethylamine (0.053 gram, 0.53 mmol) in dichloromethane (6.7 ml), yielding 0.02 gram of the product (26% yield).

¹H-NMR(CDCl₃): δ=8.82 (s-br, 1H), 8.68 (d, 1H, J=7.8 Hz), 8.53 (s, 1H), 7.75 (s-br, 1H), 7.42 (s, 1H), 7.36 (d, 1H, J=10.2 Hz), 4.34-4.4 (m, 4H), 3.96 (t, 2H, J=4.5 Hz), 3.61-3.66 (m, 18H), 3.073 (s, 3H) ppm.

MS: (m/z)=713.89 [MH°].

HR-MS (EI): calculated for $C_{27}H_{33}Cl_2FN_4O_{11}S$: 711.1242, found: 711.1248.

Preparation of Methanesulfonic Acid 2-{2-[4-(3-iodophenylamino)-6-nitro-quinazolin-7-yloxy]-ethoxy}-ethyl ester (Compound 33a), Methanesulfonic Acid 2-[2-(2-{2-[4-(3-iodophenylamino)-6-nitro-quinazoline-7-yloxy]-ethoxy}-ethoxy)-ethoxy]-ethyl ester (Compound 33b) and Methanesulfonic Acid 2-(2-{2-[2-(2-{2-[4-(3-iodophenylamino)-6-nitro-quinazolin-7-yloxy]-ethoxy}-ethoxy)-ethoxy]-ethoxy-)-ethyl ester (Compound 33c)

Compounds 33a, 33b and 33c are prepared as described hereinabove for Compounds 32a-c, respectively, using Compounds 30a-c, respectively, as the starting materials.

Preparation of Methanesulfonic Acid 2-{2-[4-(3-bromophenylamino)-6-nitro-quinazolin-7-yloxy]-ethoxy}-ethyl ester (Compound 34a), Methanesulfonic Acid 2-[2-(2-{2-[4-(3-bromophenylamino)-6-nitro-quinazoline-7-yloxy]-ethoxy}-ethoxy)-ethoxy]-ethyl ester (Compound 34b) and Methanesulfonic Acid 2-(2-{2-[2-(2-{2-[4-(3-bromophenylamino)-6-nitro-quinazolin-7-yloxy]-ethoxy}-ethoxy)-ethoxy]-ethoxy-ethoxy-)-ethyl ester (Compound 34c)

Compounds 34a, 34b and 34c are prepared as described hereinabove for Compounds 32a-c, respectively, using Compounds 31a-c, respectively, as the starting materials.

Preparation of (4,5-Dichloro-2-fluoro-phenyl)-{7-[2-(2-fluoro-ethoxy)-ethoxy]-6-nitro-quinazolin-4-yl}-amine (Compound 35a)

DAST (0.16 gram, 1 mmol) was added slowly to a cooled solution (−78° C.) of Compound 29a (0.047 gram, 0.1 mmol) in dichloromethane (2 ml) and the resulting mixture was allowed to warm to room temperature and was thereafter stirred for 12 hours. The reaction mixture was then poured to a saturated solution of sodium bicarbonate), diluted with water, extracted thrice with dichloromethane, washed with brine, and dried over sodium sulfate. Removal of the solvent under reduced pressure afforded Compound 35a (0.036 gram, 78% yield) having a purity of 94%, as determined by HPLC. The compound was used in the following procedures without further purification.

¹H-NMR(DMSO): δ=10.3 (s-br, 1H), 9.18 (s-br, 1H), 8.6 (s-br, 1H), 7.82-7.95 (m, 2H), 7.58 (s-br, 1H), 4.59-4.62 (m, 1H), 4.4-4.44 (m, 3H), 3.75-3.3.85 (m, 3H), 3.7-3.72 (m, 1H) ppm.

MS: (m/z)=460.37 [MH⁺].

Melting point=162-164° C.

HR-MS (EI): calculated for $C_{18}H_{14}Cl_2F_2N_4O_4$: 459.0423, found: 459.0419.

Preparation of 4,5-Dichloro-2-fluoro-phenyl)-[7-(2-{2-[2-(2-fluoro-ethoxy)-ethoxy]-ethoxy}-ethoxy)-6-nitro-quinazolin-4-yl]-amine (Compound 35b)

Compound 35b was prepared as described hereinabove for Compound 35a, using Compound 29b (0.05 gram, 0.09 mmol), and DAST (0.147 gram, 0.9 mmol), in dichloromethane (1.5 ml), yielding 0.042 gram of a product (83% yield), having 90% purity.

¹H-NMR (CDCl₃): δ=8.8 (s, 1H), 8.64 (d, 1H, J=7.5 Hz), 8.53 (s, 1H), 7.83 (s-br, 1H), 7.35 (s, 1H), 7.32 (s, 1H), 4.58 (m, 1H), 4.42 (m, 1H), 4.3 (m, 2H), 3.95 (m, 2H), 3.68-3.75 (m, 12H) ppm.

MS: (m/z)=548.47 [MH⁺].

HR-MS (EI): calculated for $C_{22}H_{22}Cl_2F_2N_4O_6$: 547.0948, found: 547.0952.

Preparation of (4,5-Dichloro-2-fluoro-phenyl)-(7-{2-[2-(2-{2-[2-(2-(fluoro-ethoxy}-ethoxy]-ethoxy}-ethoxy)-ethoxy]-ethoxy}-6-nitro-quinazolin-4-yl)-amine (Compound 35c)

Compound 35c was prepared as described hereinabove for Compound 35a, using Compound 29c (0.072 gram, 0.11 mmol), and DAST (0.182 gram, 0.11 mmol), in dichloromethane (3 ml), yielding 0.06 gram of a product (86% yield), having 89% purity.

¹H-NMR (CDCl₃): ϵ=8.82 (s-br, 1H), 8.68 (d, 1H, J=7.8 Hz), 8.54 (s, 1H), 7.76 (s-br, 1H), 7.44 (s, 1H), 7.34 (d, 1H, J=10.2 Hz), 4.6-4.63 (m, 1H), 4.38-4.47 (m, 3H), 3.95-3.98 (m, 2H), 3.95-3.69 (m, 18H) ppm.

MS: (m/z)=637.49 [MH°].

HR-MS (EI): calculated for $C_{26}H_{30}Cl_2F_2N_4O_8$: 635.1416, found: 635.1422.

Preparation of (3-iodophenyl)-{7-[2-(2-fluoro-ethoxy)-ethoxy]-6-nitro-quinazolin-4-yl}-amine (Compound 36a), (3-iodophenyl)-[7-(2-{2-[2-(2-fluoro-ethoxy)-ethoxy]-ethoxy}-ethoxy)-6-nitro-quinazolin-4-yl]-amine (Compound 36b) and (3-iodophenyl)-(7-{2-[2-(2-{2-[2-(2-(fluoro-ethoxy}-ethoxy]-ethoxy}-ethoxy)-ethoxy]-ethoxy}-6-nitro-quinazolin-4-yl)-amine (Compound 36c)

Compounds 36a, 36b and 36c are prepared as described hereinabove for Compounds 35a-c, using Compounds 30a-c, respectively, as starting materials.

Preparation of (3-bromophenyl)-{7-[2-(2-fluoro-ethoxy)-ethoxy]-6-nitro-quinazolin-4-yl}-amine (Compound 37a), (3-bromophenyl)-[7-(2-{2-[2-(2-fluoro-ethoxy)-ethoxy]-ethoxy}-ethoxy)-6-nitro-quinazolin-4-yl]-amine (Compound 37b) and (3-bromophenyl)-(7-{2-[2-(2-{2-[2-(2-(fluoro-ethoxy}-ethoxy]-ethoxy}-ethoxy)-ethoxy]-ethoxy}-6-nitro-quinazolin-4-yl)-amine (Compound 37c)

Compounds 37a, 37b and 37c are prepared as described hereinabove for Compounds 35a-c, using Compounds 31a-c, respectively, as starting materials.

Preparation of 4-anilino-6-aminoquinzoline Substituted by a Polyalkylene Glycol Terminating with a Reactive Group—General Procedure A solution of a 6-nitro-4-(phenylamino)quinazoline substituted by a polyalkylene glycol derivative terminating with a fifth reactive group, prepared as described hereinabove, in ethanol/water is reacted at reflux temperature with hydrazine hydrate and Raney®Nickel (Ra—Ni). The reaction mixture is filtered and evaporated, to give the corresponding 6-amino-4-(phenylamino)quinazoline substituted by a polyalkylene glycol moiety terminating with a reactive group.

Preparation of $N^4$-(4,5-dichloro-2-fluoro-phenyl)-7-[2-(2-fluoro-ethoxy)-ethoxy]-quinazolin-4,6-diamine (Compound 38a)

Compound 35a (0.036 gram, 0.078 mmol) was dissolved in a 9:1 mixture of EtOH:H$_2$P (6 ml) at 85° C., a solution of hydrazine monohydrate (0.31 mmol, 15.18 µl) in a Ra—Ni solution (500 µl) was added and the reaction mixture was stirred for 1 hour. The obtained solution was cooled and thereafter filtered over Celite®e. The filtrate was evaporated under reduced pressure to afford Compound 28a (0.018 gram, 53.7% yield), having 92% purity, as determined by HPLC. Compound 38a was used in the following procedures without further purification.
$^1$H-NMR(DMSO): δ=9.3 (s-br, 1H), 8.4 (s, 1H), 8.25 (s-br, 1H), 7.93 (m, 1H), 7.74 (d, 1H, J=9.9 Hz), 7.27 (s, 1H), 7.09 (s, 1H), 5.39 (s-br, 2H), 4.62-4.64 (m, 1H), 4.26-4.29 (m, 3H), 3.88-3.9 (m, 3H), 3.79-3.81 (m, 1H) ppm.
MS: (m/z)=430.45 [MH$^+$].
Melting point=126° C.
HR-MS (EI): calculated for C$_{18}$H$_{16}$Cl$_2$F$_2$N$_4$O$_2$: 429.065, found: 429.0646.

Preparation of $N^4$-(4,5-Dichloro-2-fluoro-phenyl)-(2-{2-[2-(2-Fluoro-ethoxy)-ethoxy]-ethoxy}-ethoxy)-quinazoline-4,6-diamine (Compound 38b)

Compound 38b was prepared as described hereinabove for Compound 38a, using Compound 35b (0.12 gram, 0.21 mmol), hydrazine monohydrate (0.87 mmol, 42.56 µl) and Ra—Ni solution (700 µl) in a 9:1 mixture of ethanol/water (23 ml), yielding 0.085 grams of a product (75% yield) having a 90% purity.
$^1$H-NMR(CDCl$_3$): δ=8.62 (s, 1H), 8.58 (s, 1H), 8.3 (s, 1H), 7.5 (s-br, 1H), 7.29 (d, 1H, J=10.8 Hz), 5.2 (s-br, 2H), 4.34-4.36 (m, 2H), 3.9-3.93 (m, 2H), 3.39-3.68 (m, 12H) ppm.
MS: (m/z)=518 [MH$^+$].
HR-MS (EI): calculated for C$_{22}$H$_{24}$Cl$_2$F$_2$N$_4$O$_4$: 517.1163, found: 517.1157.

Preparation of $N^4$-(4,5-Dichloro-2-fluoro-phenyl)-7-{2-[2-(2-{2-[2-(2-fluoro-ethoxy)-ethoxy]-ethoxy}-ethoxy)-ethoxy]-ethoxy}-quinazoline-4,6-diamine (Compound 38c)

Compound 38c was prepared as described hereinabove for Compound 38a, using Compound 35c (0.045 gram, 0.07 mmol), hydrazine monohydrate (0.28 mmol, 13.7 µl) and Ra—Ni solution (400 µl) in a 9:1 mixture of ethanol/water (8.8 ml), yielding 0.029 gram of a product (68% yield) having a 88% purity.
$^1$H-NMR(CDCl$_3$): δ=8.97 (d, 1H, J=8.1 Hz), 8.61 (s, 1H), 7.26 (d, 1H, J=9.3 Hz), 7.19 (s, 2H), 7.03 (s, 1H), 4.6-4.63 (m, 1H), 4.45-4.47 (m, 1H), 4.3-4.33 (m, 3H), 3.93-3.96 (m, 3H), 3.65-3.79 (m, 16H) ppm.
MS: (m/z)=607.62 [MH$^+$].
HR-MS (EI): calculated for C$_{26}$H$_{32}$Cl$_2$F$_2$N$_4$O$_6$: 605.1726, found: 605.1721.

Preparation of $N^4$-(3-iodophenyl)-7-[2-(2-fluoro-ethoxy)-ethoxy]-quinazoline-4,6-diamine (Compound 39a), $N^4$-(3-iodophenyl)-(2-{2-[2-(2-Fluoro-ethoxy)-ethoxy]-ethoxy}-ethoxy)-quinazoline-4,6-diamine (Compound 39b) and $N^4$-(3-iodophenyl)-7-{2-[2-(2-{2-[2-(2-fluoro-ethoxy)-ethoxy]-ethoxy}-ethoxy)-ethoxy]-ethoxy}-quinazoline-4,6-diamine (Compound 39c)

Compounds 39a, 39b and 39c are prepared as described hereinabove for Compounds 38a-c, respectively, using Compounds 36a-c, respectively, as starting materials.

Preparation of $N^4$-(3-bromophenyl)-7-[2-(2-fluoro-ethoxy)-ethoxy]quinazoline-4,6-diamine (Compound 40a), N -(3-bromophenyl)-(2-{2-[2-(2-Fluoro-ethoxy)-ethoxy]-ethoxy}-ethoxy)-quinazoline-4,6-diamine (Compound 40b) and $N^4$-(3-bromophenyl)-7-{2-[2-(2-{2-[2-(2-fluoro-ethoxy)-ethoxy]-ethoxy}-ethoxy)-ethoxy]-ethoxy}-quinazoline-4,6-diamine (Compound 40c)

Compounds 40a, 40b and 40c are prepared as described hereinabove for Compounds 38a-c, respectively, using Compounds 37a-c, respectively, as starting materials.

Preparation of 4-anilino-6-aminoquinzoline Substituted by a Polyalkylene Glycol Moiety—General Procedure A solution of a 6-nitro-4-(phenylamino)quinazoline substituted by a polyalkylene glycol, prepared as described hereinabove, in ethanol/water is reacted at reflux temperature with hydrazine hydrate and Raney® Nickel (Ra—Ni). The reaction mixture is filtered and evaporated, to give the corresponding 6-amino-4-(phenylamino)quinazoline substituted by a polyalkylene glycol moiety (terminating with a hydroxyl group).

Preparation of $N^4$-(4,5-dichloro-2-fluoro-phenyl)-7-[2-ethoxy-ethoxy]-quinazoline-4,6-diamine (Compound 41a)

Compound 29a is dissolved in a 9:1 mixture of EtOH:H$_2$O at 85° C., a solution of hydrazine monohydrate in a Ra—Ni solution is added and the reaction mixture is stirred for 1 hour.

The obtained solution is cooled and thereafter filtered over Celite®. The filtrate is evaporated under reduced pressure to afford Compound 41a.

Preparation of $N^4$-(4,5-Dichloro-2-fluoro-phenyl)-(2-{2-[2-(2-ethoxy)-ethoxy]-ethoxy}-ethoxy)-quinazoline-4,6-diamine (Compound 41b):

Compound 41b is prepared as described hereinabove for Compound 41a, using Compound 29b a starting material.

Preparation of $N^4$-(4,5-Dichloro-2-fluoro-phenyl)-7-{2-[2-(2-{2-[2-ethoxy-ethoxy]-ethoxy}-ethoxy)-ethoxy]-ethoxy}-quinazoline-4,6-diamine (Compound 41c)

Compound 41c was prepared as described hereinabove for Compound 41a, using Compound 29c as a starting material.

Preparation of $N^4$-(3-iodophenyl)-7-[2-ethoxy-ethoxy]-quinazoline-4,6-diamine (Compound 42a), $N^4$-(3-iodophenyl)-(2-{2-[2-ethoxy-ethoxy]-ethoxy}-ethoxy)-quinazoline-4,6-diamine (Compound 42b) and $N^4$-(3-iodophenyl)-7-{2-[2-(2-t{-[2-ethoxy)-ethoxy]-ethoxy}-ethoxy)-ethoxy]-ethoxy}-quinazoline-4,6-diamine (Compound 42c)

Compounds 42a, 42b and 42c are prepared as described hereinabove for Compounds 41a-c, respectively, using Compounds 30a-c, respectively, as starting materials.

Preparation of $N^4$-(3-bromophenyl)-7-[2-ethoxy-ethoxy]-quinazoline-4,6-diamine (Compound 43a), $N^4$-(3-bromophenyl)-(2-{2-[2-(ethoxy)-ethoxy]-ethoxy}-ethoxy)-quinazoline-4,6-diamine (Compound 43b) and $N^4$-(3-bromophenyl)-7-{2-[2-(2-{2-[2-(ethoxy)-ethoxy]-ethoxy}-ethoxy)-ethoxy]-ethoxy}-quinazoline-4,6-diamine (Compound 43c)

Compounds 43a, 43b and 43c are prepared as described hereinabove for Compounds 41a-c, respectively, using Compounds 31a-c, respectively, as starting materials.

Preparation of [4-(phenylamino)-quinazoline-6-yl]amides Substituted by a Polyalkylene Glycol Moiety—General Procedure A 4-(phenylamino)-6-aminoquinazoline substituted by a polyalkylene glycol moiety, prepared as described hereinabove, is reacted with α,β-unsaturated carboxylic acid or with a derivative thereof, or with a reactive carboxylic derivative substituted at the α position by a leaving group, at 0° C. in THF, in the presence of a chemically reactive base such as tertiary amine, to give the final product, according to any of the procedures described in U.S. Pat. Nos. 6,562,319, U.S. patent application Ser. No. 09/802,928 (Publication No. 2004/0265228, recently granted), and WO 04/064718.

Optionally, 4-(phenylamino)-6-aminoquinazoline substituted by a polyalkylene glycol moiety, prepared as described hereinabove, is reacted with α, β-unsaturated acyl chloride that is terminated with a reactive halogen group, at 0° C. in THF, in the presence of a tertiary amine, and the obtained product is then reacted with a substituted alkyl at 0° C. in THF and purified by silica gel chromatography, to give a substituted [4-(phenylamino)-quinazoline-6-yl]alkylamide, further substituted by a polyalkylene glycol moiety as a final product. Further optionally, the obtained product is further reacted thereafter with a reactive compound such as alkyl iodide, at 40° C., to give the final product, as described in U.S. patent application Ser. No. 09/802,928 ((Publication No. 2004/0265228).

Using the above general procedure, the following exemplary [4-(phenylamino)-quinazoline-6-yl]amides substituted by a polyalkylene glycol moiety, according to the present embodiments, are prepared:

2-Chloro-N-{4-(4,5-Dichloro-2-fluoro-phenylamino)-7-[2-(2-fluoro-ethoxy)-ethoxy]-quinazoline-6-yl}-acetamide (Compound 1a);

2-Chloro-N-[4-(4,5-Dichloro-2-fluoro-phenylamino)-7-(2-{2-[2-(2-fluoro-ethoxy)-ethoxy]-ethoxy}-ethoxy)-quinazoline-6-yl]-acetamide (Compound 1b);

2-Chloro-N-(4-(4,5-Dichloro-2-fluoro-phenylamino)-7-{2-[2-(2-{2-[2-(2-fluoro-ethoxy)-ethoxy]-ethoxy}-ethoxy)-ethoxy]-ethoxy}-quinazoline-6-yl)-acetamide (Compound 1c);

2-Chloro-N-{4-(3-iodophenylamino)-7-[2-(2-fluoro-ethoxy)-ethoxy]-quinazoline-6-yl}-acetamide (Compound 2a);

2-Chloro-N-[4-(3-iodophenylamino)-7-(2-{2-[2-(2-fluoro-ethoxy)-ethoxy]-ethoxy}-ethoxy)-quinazoline-6-yl]-acetamide (Compound 2b);

2-Chloro-N-(4-(3-iodophenylamino)-7-{2-[2-(2-{2-[2-(2-fluoro-ethoxy)-ethoxy]-ethoxy}-ethoxy)-ethoxy]-ethoxy}-quinazoline-6-yl)-acetamide (Compound 2c);

2-Chloro-N-{4-(3-bromophenylamino)-7-[2-(2-fluoro-ethoxy)-ethoxy]-quinazoline-6-yl}-acetamide (Compound 3a);

2-Chloro-N-[4-(43-bromophenylamino)-7-(2-{2-[2-(2-fluoro-ethoxy)-ethoxy]-ethoxy}-ethoxy)-quinazoline-6-yl]-acetamide (Compound 3b);

2-Chloro-N-(4-(3-bromophenylamino)-7-{2-[2-(2-{2-[2-(2-fluoro-ethoxy)-ethoxy]-ethoxy}-ethoxy)-ethoxy]-ethoxy}-quinazoline-6-yl)-acetamide (Compound 3c);

2-Methoxy-N-{4-(4,5-Dichloro-2-fluoro-phenylamino)-7-[2-(2-fluoro-ethoxy)-ethoxy]-quinazoline-6-yl}-acetamide (Compound 4a);

2-Methoxy-N-[4-(4,5-Dichloro-2-fluoro-phenylamino)-7-(2-{2-[2-(2-fluoro-ethoxy)-ethoxy]-ethoxy}-ethoxy)-quinazoline-6-yl]-acetamide (Compound 4b);

2-Methoxy-N-(4-(4,5-Dichloro-2-fluoro-phenylamino)-7-{2-[2-(2-{2-[2-(2-fluoro-ethoxy)-ethoxy]-ethoxy}-ethoxy)-ethoxy]-ethoxy}-quinazoline-6-yl)-acetamide (Compound 4c);

2-Methoxy-N-{4-(3-iodophenylamino)-7-[2-(2-fluoro-ethoxy)-ethoxy]-quinazoline-6-yl}-acetamide (Compound 5a);

2-Methoxy-N-[4-(3-iodophenylamino)-7-(2-{2-[2-(2-fluoro-ethoxy)-ethoxy]-ethoxy}-ethoxy)-quinazoline-6-yl]-acetamide (Compound 5b);

2-Methoxy-N-(4-(3-iodophenylamino)-7-{2-[2-(2-{2-[2-(2-fluoro-ethoxy)-ethoxy]-ethoxy}-ethoxy)-ethoxy]-ethoxy}-quinazoline-6-yl)-acetamide (Compound 5c);

2-Methoxy-N-{4-(3-bromophenylamino)-7-[2-(2-fluoro-ethoxy)-ethoxy]-quinazoline-6-yl}-acetamide (Compound 6a);

2-Methoxy-N-[4-(3-bromophenylamino)-7-(2-{2-[2-(2-fluoro-ethoxy)-ethoxy]-ethoxy}-ethoxy)-quinazoline-6-yl]-acetamide (Compound 6b);

2-Methoxy-N-(4-(3-bromophenylamino)-7-{2-[2-(2-{2-[2-(2-fluoro-ethoxy)-ethoxy]-ethoxy}-ethoxy)-ethoxy]-ethoxy}-quinazoline-6-yl)-acetamide (Compound 6c);

N-{4-(4,5-Dichloro-2-fluoro-phenylamino)-7-[2-(2-fluoro-ethoxy)-ethoxy]-quinazoline-6-yl}-acrylamide (Compound 7a);

N-[4-(4,5-Dichloro-2-fluoro-phenylamino)-7-(2-{2-[2-(2-fluoro-ethoxy)-ethoxy]-ethoxy}-ethoxy)-quinazoline-6-yl]-acrylamide (Compound 7b);

N-(4-(4,5-Dichloro-2-fluoro-phenylamino)-7-{2-[2-(2-{2-[2-(2-fluoro-ethoxy)-ethoxy]-ethoxy}-ethoxy)-ethoxy]-ethoxy}-quinazoline-6-yl)-acrylamide (Compound 7c);

N-{4-(3-iodophenylamino)-7-[2-(2-fluoro-ethoxy)-ethoxy]-quinazoline-6-yl}-acrylamide (Compound 8a);

N-[4-(3-iodophenylamino)-7-(2-{2-[2-(2-fluoro-ethoxy)-ethoxy]-ethoxy}-ethoxy)-quinazoline-6-yl]-acrylamide (Compound 8b);

N-(4-(3-iodophenylamino)-7-{2-[2-(2-{2-[2-(2-fluoro-ethoxy)-ethoxy]-ethoxy}-ethoxy)-ethoxy]-ethoxy}-quinazoline-6-yl)-acrylamide (Compound 8c);

N-{4-(3-bromophenylamino)-7-[2-(2-fluoro-ethoxy)-ethoxy]-quinazoline-6-yl}-acrylamide (Compound 9a);

N-[4-(3-bromophenylamino)-7-(2-{2-[2-(2-fluoro-ethoxy)-ethoxy]-ethoxy}-ethoxy)-quinazoline-6-yl]-acrylamide (Compound 9b);

N-(4-(3-bromophenylamino)-7-{2-[2-(2-{2-[2-(2-fluoro-ethoxy)-ethoxy]-ethoxy}-ethoxy)-ethoxy]-ethoxy}-quinazoline-6-yl)-acrylamide (Compound 9c);

4-dimethylamino-but-2-enoic acid {4-(4,5-Dichloro-2-fluoro-phenylamino)-7-[2-(2-fluoro-ethoxy)-ethoxy]-quinazoline-6-yl}-amide (Compound 10a);

4-dimethylamino-but-2-enoic acid {4-(4,5-Dichloro-2-fluoro-phenylamino)-7-(2-{2-[2-(2-fluoro-ethoxy)-ethoxy]-ethoxy}-ethoxy)-quinazoline-6-yl}-amide (Compound 10b);

4-dimethylamino-but-2-enoic acid {(4-(4,5-Dichloro-2-fluoro-phenylamino)-7-{2-[2-(2-{2-[2-(2-fluoro-ethoxy)-ethoxy]-ethoxy}-ethoxy)-ethoxy]-ethoxy}-quinazoline-6-yl}-amide (Compound 10c);

4-dimethylamino-but-2-enoic acid {4-(3-iodophenylamino)-7-[2-(2-fluoro-ethoxy)-ethoxy]-quinazoline-6-yl}-amide (Compound 11a);

4-dimethylamino-but-2-enoic acid [4-(3-iodophenylamino)-7-(2-{2-[2-(2-fluoro-ethoxy)-ethoxy]-ethoxy}-ethoxy)-quinazoline-6-yl]-amide (Compound 11b);

4-dimethylamino-but-2-enoic acid {(4-(3-iodophenylamino)-7-{2-[2-(2-{2-[2-(2-fluoro-ethoxy)-ethoxy]-ethoxy}-ethoxy)-ethoxy]-ethoxy}-quinazoline-6-yl}-amide (Compound 11c);

4-dimethylamino-but-2-enoic acid {4-(3-bromophenylamino)-7-[2-(2-fluoro-ethoxy)-ethoxy]-quinazoline-6-yl}-amide (Compound 12a);

4-dimethylamino-but-2-enoic acid [4-(43-bromophenylamino)-7-(2-{2-[2-(2-fluoro-ethoxy)-ethoxy]-ethoxy}-ethoxy)-quinazoline-6-yl]-amide (Compound 12b); and 4-dimethylamino-but-2-enoic acid (4-(3-bromophenylamino)-7-{2-[2-(2-{2-[2-(2-fluoro-ethoxy)-ethoxy]-ethoxy}-ethoxy)-ethoxy]-ethoxy}-quinazoline-6-yl)-amide (Compound 12c).

Figure 2A:
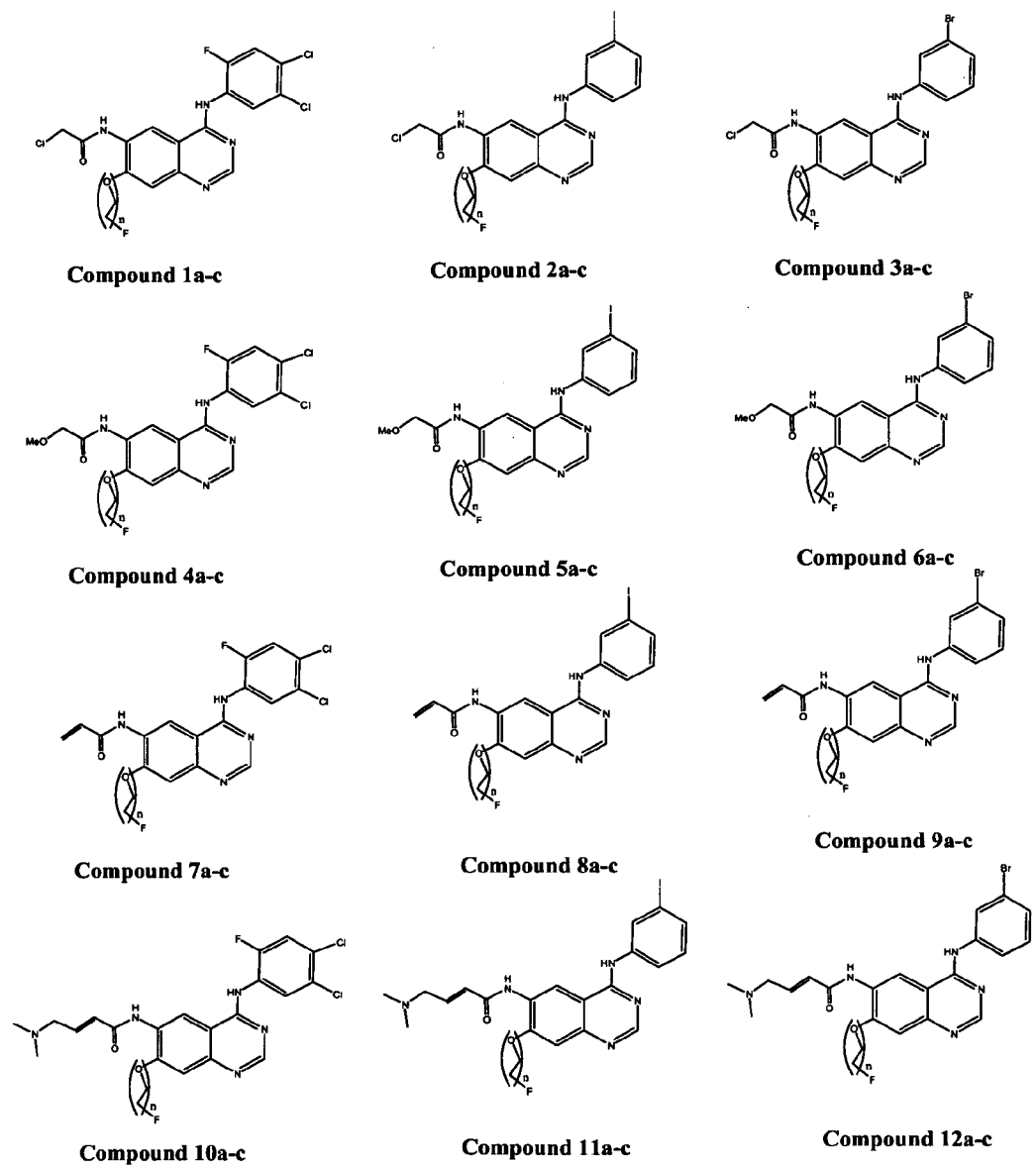
FIGS. 2*a* and *b* present the chemical structures (2D) of exemplary compounds (Compounds 1(a-c)-12(a-c) in FIG. 2*a* and Compounds 51(a-c)-62(a-c) in FIG. 2*b*) according to preferred embodiments of the present invention.

The chemical structures of these compounds are presented in FIG. 2a.

Additional derivatives or analogs of [4-(phenylamino)-quinazoline-6-yl]amides substituted by other polyalkylene glycol moieties, optionally terminating with functional groups other than fluoro (e.g., hydroxy, alkoxy, thiol, amine), are similarly prepared, using the general procedures described hereinabove.

Such derivatives or analogs of [4-(phenylamino)-quinazoline-6-yl]amides substituted by a polyalkylene glycol moiety that terminates by a hydroxy group are typically prepared by reacting compounds 41(a-c), 42(a-c) or 43(a-c) with α,β-unsaturated carboxylic acid or with a derivative thereof, or with a reactive carboxylic derivative substituted at the α position by a leaving group, as described hereinabove.

Thus, the following additional exemplary [4-(phenylamino)-quinazoline-6-yl]amides substituted by a polyalkylene glycol moiety, according to the present embodiments, are prepared:

2-Chloro-N-{4-(4,5-Dichloro-2-fluoro-phenylamino)-7-[2-(2-ethoxy)ethoxy]-quinazoline-6-yl}-acetamide (Compound 51a);

2-Chloro-N-[4-(4,5-Dichloro-2-fluoro-phenylamino)-7-(2-{2-[2-(2-ethoxy)-ethoxy]-ethoxy}-ethoxy)-quinazoline-6-yl]-acetamide (Compound 51b);

2-Chloro-N-(4-(4,5-Dichloro-2-fluoro-phenylamino)-7-{2-[2-(2-{2-[2-(2-ethoxy)-ethoxy]-ethoxy}-ethoxy)-ethoxy]-ethoxy}-quinazoline-6-yl)-acetamide (Compound 51c);

2-Chloro-N-{4-(3-iodophenylamino)-7-[2-(2-ethoxy)-ethoxy]-quinazoline-6-yl}-acetamide (Compound 52a);

2-Chloro-N-[4-(3-iodophenylamino)-7-(2-{2-[2-(2-ethoxy)-ethoxy]-ethoxy}-ethoxy)-quinazoline-6-yl]-acetamide (Compound 52b);

2-Chloro-N-(4-(3-iodophenylamino)-7-{2-[2-(2-{2-[2-(2-ethoxy)-ethoxy]-ethoxy}-ethoxy)-ethoxy]-ethoxy}-quinazoline-6-yl)-acetamide (Compound 52c);

2-Chloro-N-{4-(3-bromophenylamino)-7-[2-(2-ethoxy)-ethoxy]-quinazoline-6-yl}-acetamide (Compound 53a);

2-Chloro-N-[4-(43-bromophenylamino)-7-(2-{2-[2-(2-ethoxy)-ethoxy]-ethoxy}-ethoxy)-quinazoline-6-yl]-acetamide (Compound 53b);

2-Chloro-N-(4-(3-bromophenylamino)-7-{2-[2-(2-{2-[2-(2-ethoxy)-ethoxy]-ethoxy}-ethoxy)-ethoxy]-ethoxy}-quinazoline-6-yl)-acetamide (Compound 53c);

2-Methoxy-N-{4-(4,5-Dichloro-2-fluoro-phenylamino)-7-[2-(2-ethoxy)-ethoxy]-quinazoline-6-yl}-acetamide (Compound 54a);

2-Methoxy-N-[4-(4,5-Dichloro-2-fluoro-phenylamino)-7-(2-{2-[2-(2-ethoxy)-ethoxy]-ethoxy}-ethoxy)-quinazoline-6-yl]-acetamide (Compound 54b);

2-Methoxy-N-(4-(4,5-Dichloro-2-fluoro-phenylamino)-7-{2-[2-(2-{2-[2-(2-ethoxy)-ethoxy]-ethoxy}-ethoxy)-ethoxy]-ethoxy}-quinazoline-6-yl)-acetamide (Compound 54c);

2-Methoxy-N-{4-(3-iodophenylamino)-7-[2-(2-ethoxy)-ethoxy]-quinazoline-6-yl}-acetamide (Compound 5a);

2-Methoxy-N-[4-(3-iodophenylamino)-7-(2-{2-[2-(2-ethoxy)-ethoxy]-ethoxy}-ethoxy)-quinazoline-6-yl]-acetamide (Compound 55b);

2-Methoxy-N-(4-(3-iodophenylamino)-7-{2-[2-(2-{2-[2-(2-ethoxy)-ethoxy]-ethoxy}-ethoxy)-ethoxy]-ethoxy}-quinazoline-6-yl)-acetamide (Compound 55c);

2-Methoxy-N-{4-(3-bromophenylamino)-7-[2-(2-ethoxy)-ethoxy]-quinazoline-6-yl}-acetamide (Compound 56a);

2-Methoxy-N-[4-(3-bromophenylamino)-7-(2-{2-[2-(2-ethoxy)-ethoxy]-ethoxy}-ethoxy)-quinazoline-6-yl]-acetamide (Compound 56b);

2-Methoxy-N-(4-(3-bromophenylamino)-7-{2-[2-(2-{2-[2-(2-ethoxy)-ethoxy]-ethoxy}-ethoxy)-ethoxy]-ethoxy}-quinazoline-6-yl)-acetamide (Compound 56c);

N-{4-(4,5-Dichloro-2-fluoro-phenylamino)-7-[2-(2-ethoxy)-ethoxy]-quinazoline-6-yl}-acrylamide (Compound 57a);

N-[4-(4,5-Dichloro-2-fluoro-phenylamino)-7-(2-{2-[2-(2-ethoxy)-ethoxy]-ethoxy}-ethoxy)-quinazoline-6-yl]-acrylamide (Compound 57b);

N-(4-(4,5-Dichloro-2-fluoro-phenylamino)-7-{2-[2-(2-{2-[2-(2-ethoxy)-ethoxy]-ethoxy}-ethoxy)-ethoxy]-ethoxy}-quinazoline-6-yl)-acrylamide (Compound 57c);

N-{4-(3-iodophenylamino)-7-[2-(2-ethoxy)-ethoxy]-quinazoline-6-yl}-acrylamide (Compound 58a);

N-[4-(3-iodophenylamino)-7-(2-{2-[2-(2-ethoxy)-ethoxy]-ethoxy}-ethoxy)-quinazoline-6-yl]-acrylamide (Compound 58b);

N-(4-(3-iodophenylamino)-7-{2-[2-(2-{2-[2-(2-ethoxy)-ethoxy]-ethoxy}-ethoxy)-ethoxy]-ethoxy}-quinazoline-6-yl)-acrylamide (Compound 58c);

N-{4-(3-bromophenylamino)-7-[2-(2-ethoxy)-ethoxy]-quinazoline-6-yl}-acrylamide (Compound 59a);

N-[4-(3-bromophenylamino)-7-(2-{2-[2-(2-ethoxy)-ethoxy]-ethoxy}-ethoxy)-quinazoline-6-yl]-acrylamide (Compound 59b);

N-(4-(3-bromophenylamino)-7-{2-[2-(2-{2-[2-(2-ethoxy)-ethoxy]-ethoxy}-ethoxy)-ethoxy]-ethoxy}-quinazoline-6-yl)-acrylamide (Compound 59c);

4-dimethylamino-but-2-enoic acid {4-(4,5-Dichloro-2-fluoro-phenylamino)-7-[2-(2-ethoxy)-ethoxy]-quinazoline-6-yl}-amide (Compound 60a);

4-dimethylamino-but-2-enoic acid {4-(4,5-Dichloro-2-fluoro-phenylamino)-7-(2-{2-[2-(2-ethoxy)-ethoxy]-ethoxy}-ethoxy)-quinazoline-6-yl}-amide (Compound 60b);

4-dimethylamino-but-2-enoic acid {(4-(4,5-Dichloro-2-fluoro-phenylamino)-7-{2-[2-(2-{2-[2-(2-ethoxy)-ethoxy]-ethoxy}-ethoxy)-ethoxy]-ethoxy}-quinazoline-6-yl}-amide (Compound 60c);

4-dimethylamino-but-2-enoic acid {4-(3-iodophenylamino)-7-[2-(2-ethoxy)-ethoxy]-quinazoline-6-yl}-amide (Compound 61a);

4-dimethylamino-but-2-enoic acid [4-(3-iodophenylamino)-7-(2-{2-[2-(2-ethoxy)-ethoxy]-ethoxy}-ethoxy)-quinazoline-6-yl]-amide (Compound 61b);

4-dimethylamino-but-2-enoic acid {(4-(3-iodophenylamino)-7-{2-[2-(2-{2-[2-(2-ethoxy)-ethoxy]-ethoxy}-ethoxy)-ethoxy]-ethoxy}-quinazoline-6-yl}-amide (Compound 61c);

4-dimethylamino-but-2-enoic acid {4-(3-bromophenylamino)-7-[2-(2-fluoro-ethoxy)-ethoxy]-quinazoline-6-yl}-amide (Compound 62a);

4-dimethylamino-but-2-enoic acid [4-(43-bromophenylamino)-7-(2-{2-[2-(2-ethoxy)-ethoxy]-ethoxy}-ethoxy)-quinazoline-6-yl]-amide (Compound 62b); and 4-dimethylamino-but-2-enoic acid (4-(3-bromophenylamino)-7-{2-[2-(2-{2-[2-(2-ethoxy)-ethoxy]-ethoxy}-ethoxy)-ethoxy]-ethoxy}-quinazoline-6-yl)-amide (Compound 62c).

Figure 2B:
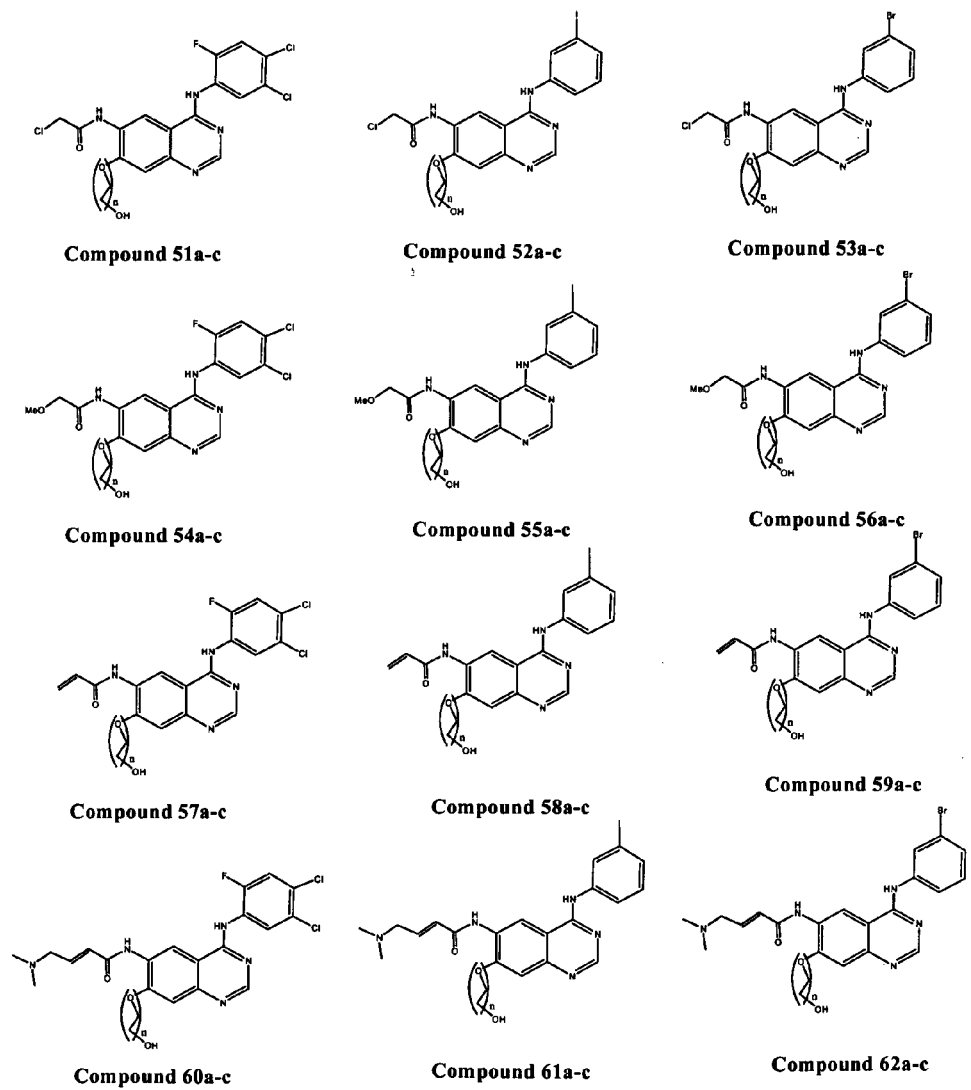

The chemical structures of these compounds are presented in FIG. 2b.

Figure 3A:
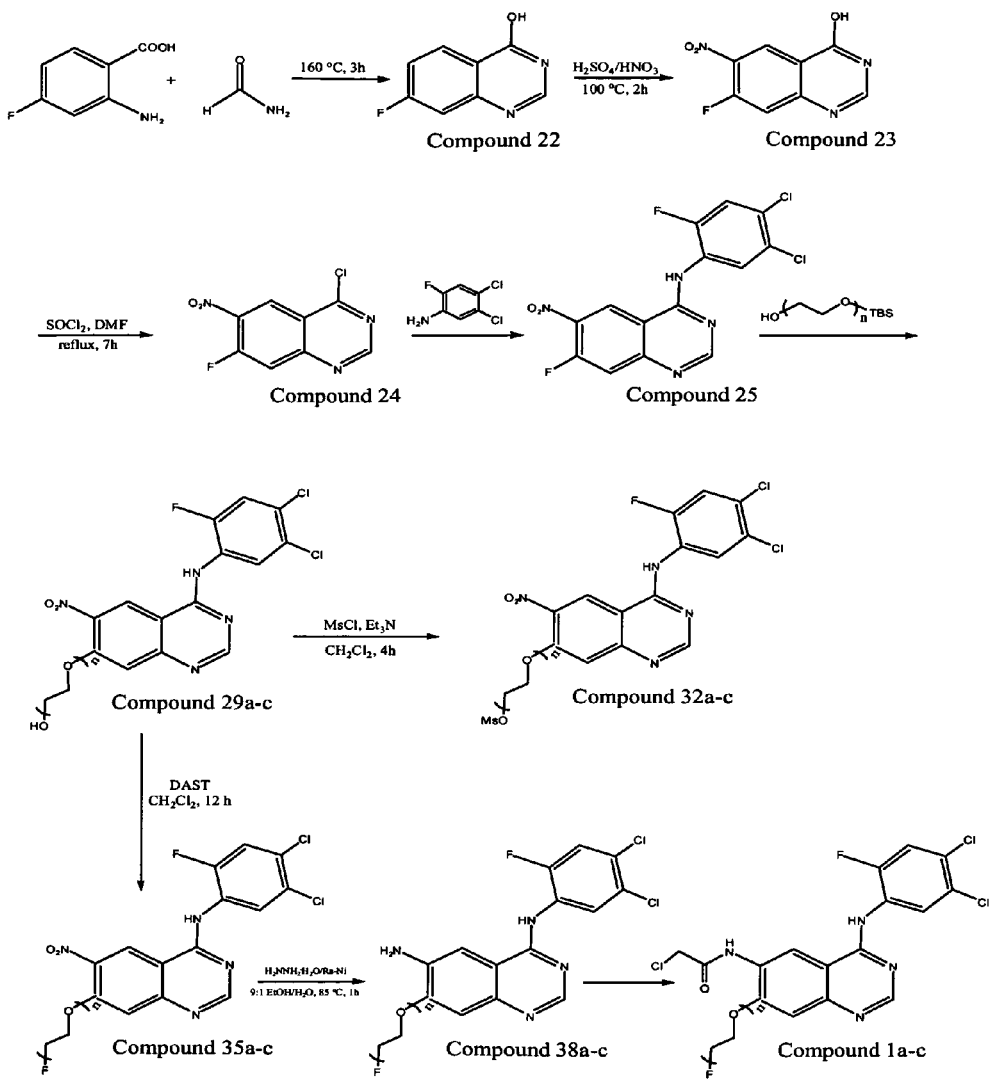
FIGS. 3*a-c* are a scheme presenting the synthetic route for preparing representative examples of compounds according to the present invention (Compounds 1a-c), wherein the last synthetic procedure involves reaction with ClC(=O)CH$_2$Cl and N,N-DIPEA in THF at 0° C.

As a representative example, the preparation of Compounds 1a-c is depicted in FIG. 3a. The overall syntheses of these compounds is described hereinbelow.

Preparation of 2-Chloro-N-{4-(4,5-Dichloro-2-fluoro-phenylamino) -7-[2-(2-fluoro-ethoxy)-ethoxy]-quinazoline-6-yl}-acetamide (Compound 1a)

Compound 38a (0.07 gram, 0.16 mmol) was dissolved in dry THF (7 ml) and the solution was stirred in an ice bath for 10 minutes. Diisopropylethylamine (DIPEA) (0.326 mmol, 56.8 µl) and chloroacetylchloide (0.326 mmol, 25.9 µl) were thereafter added and the resulting mixture was stirred for 1 hour at 0° C. and the solvent was thereafter removed under reduced pressure. The obtained residue was extracted with EtOAc (3×25 ml) and washed with NaHCO$_3$ (4%) (3×10 ml). The combined extracts were dried over Na$_2$SO$_4$, filtered and evaporated. The crude product was purified by silica gel chromatography, using a mixture of 1.5% MeOH in CH$_2$Cl$_2$ as eluent, to obtain Compound 1a (0.03 gram, 37% yield).

$^1$H NMR (DMSO): δ=9.89 (s-br, 1H), 9.66 (s-br, 1H), 8.85 (s, 1H), 8.42 (s-br, 1H), 7.75-7.84 (m, 2H), 7.33 (s-br, 1H), 4.6-4.63 (m, 1H), 4.47 (s, 2H), 4.38 (m, 3H), 3.88-3.91 (m, 2H), 3.79-3.82 (m, 1H), 3.69-3.71 (m, 1H) ppm.

MS: (m/z)=507.07 [MH$^+$].

Melting point=167-169° C.

HR-MS (EI): calculated for C$_{20}$H$_{17}$Cl$_3$F$_2$N$_4$O$_3$: 505.0412, found: 505.0413.

Preparation of 2-Chloro-N-[4-(4,5-Dichloro-2-fluoro-phenylamino)-7-(2-{2-[2-(2-fluoro-ethoxy)-ethoxy]-ethoxy}-ethoxy)-quinazoline-6-yl]-acetamide (Compound 1b)

Compound 1b was prepared as described hereinabove for Compound 1a, using Compound 38b (0.085 gram, 0.16 mmol), DIPEA (0.33 mmol, 57.8 µl) and chloroacetylchloride (0.33 mmol, 26.4 µ) in THF (11 ml), as starting materials, to give 0.025 gram (26% yield) of the product.

$^1$H-NMR(CDCl$_3$): δ=9.43 (s, 1H), 9.02 (s, 1H), 8.76 (s, 1H), 7.3-7.34 (m, 2H), 4.63 (m, 1H), 4.48 (m, 1H), 4.41 (m, 2H), 4.3 (s, 2H), 4 (m, 2H), 3.68-3.77 (m, 10H) ppm.

MS: (m/z)=594.8 [MH$^+$].

Melting point=135-137° C.

HR-MS (EI): calculated for C$_{24}$H$_{25}$Cl$_3$F$_2$N$_4$O$_5$: 593.0920, found: 593.0937.

Preparation of 2-Chloro-N-(4-(4,5-Dichloro-2-fluoro-phenylamino)-7-{2-[2-(2-{2-[2-(2-fluoro-ethoxy)-ethoxy]-ethoxy}-ethoxy)-ethoxy]-ethoxy}-quinazoline-6-yl)-acetamide (Compound 1c)

Compound 1c was prepared as described hereinabove for Compound 1a, using Compound 38c (0.13 gram, 0.21 mmol), DIPEA (0.43 mmol, 75.1 µl) and chloroacetylchloride (0.43 mmol, 34.3 µl in THF (18 ml), yielding 0.03 gram of the product (21% yield).

$^1$H-NMR(CDCl$_3$): δ=9.45 (s, 1H), 9.01 (s, 1H), 8.85 (d, 1H, J=7.8 Hz), 8.75 (s, 1H), 7.53 (s-br, 1H), 7.33 (s, 1H), 4.61-4.64 (m, 1H), 4.45-4.48 (m, 1H), 4.37-4.41 (m, 2H), 4.3 (s, 2H), 3.97-4 (m, 2H), 3.64-3.75 (m, 18H) ppm.

MS: (m/z)=684.07 (MH+).

Melting point=109-111° C.

HR-MS (EI): calculated for C$_{28}$H$_{33}$Cl$_3$F$_2$N$_4$O$_7$: 681.1484, found: 681.1461.

Figure 3B:
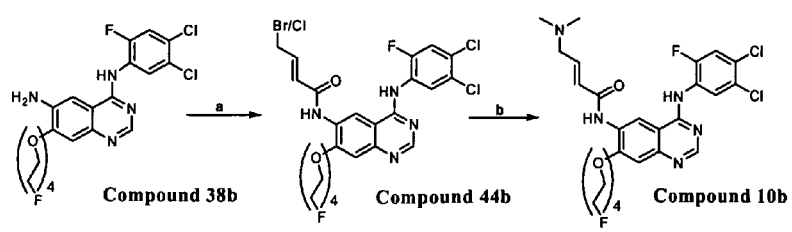

In another representative example, the preparation of Compound 10b is described hereinbelow and is further depicted in FIG. 3b.

Preparation of 4-Bromo/Chloro-but-2-enoic acid[4-(4,5-dichloro-2-fluoro-phenylamino)-7-(2-{2-[2-(2-fluoro-ethoxy)-ethoxy]-ethoxy}-ethoxy) -quinazoline-6-yl]-amide (Compound 44b)

Compound 38b (0.036 gram, 0.069 mmol) was dissolved in dry THF (1 ml), and added dropwise to a solution of 4-bromo/chloro-but-2-enoyl chloride (0.034 gram, 0.2 mmol) in THF (0.5 ml) at 0° C. Diisopropylethylamine (DIPEA) (0.2 mmol, 36.2 µl) was added to the cooled solution, and the reaction mixture was stirred for 1 hour. The solvent was thereafter evaporated and the residue was extracted with EtOAc (3×25 ml) from water. The combined extracts were washed with brine (5 ml), dried (Na$_2$SO$_4$), filtered and evaporated. The crude product was purified by silica gel chromatography, using a mixture of 2% MeOH in DCM as eluent, to obtain Compound 44b (0.028 gram, 60% yield).

$^1$H NMR (CDCl$_3$): δ=9.15(s, 1H), 8.86 (d, 1H, J=7.8 Hz), 8.73 (s, 1H), 8.65 (s-br, 1H), 7.56 (s-br, 1H), 7.32 (t, 1H), 7.06-7.13 (dt, 1H, J=5.7; 6 Hz), 6.41-6.47 (dm, 1H), 4.6-4.63 (m, 1H), 4.44-4.47 (m, 1H), 4.38-4.41 (m, 3H), 3.99-4.02 (m, 3H), 3.65-3.78 (m, 10H) ppm.

MS: (m/z)=621.3/665.2 (MH+).

Mp=95-96° C.

HRMS (EI): calcd. for C$_{26}$H$_{27}$BrCl$_3$F$_2$N$_4$O$_5$: 619.1103, 663.061 found: 619.1093, 663.0599.

Preparation of 4-Dimethylamino-but-2-enoic acid [4-(4,5-dichloro-2-fluoro-phenylamino)-7-(2-{2-[2-(2-fluoro-ethoxy)-ethoxy]-ethoxy}-ethoxy)-quinazoline-6-yl]-amide (Compound 10b)

Compound 44b (0.028 gram, 0.042 mmol) dissolved in THF (1 ml), was added dropwise to a cooled solution of dimethylamine (2 ml) in THF (2 M), and diisopropylethylamine (0.18 mmol, 31.4 μ) was added. The reaction mixture was stirred at 0° C. for 30 minutes, and then heated at 60° C. for additional 30 minutes. The solvent was thereafter evaporated, and the residue was extracted with ethyl acetate (3×20 ml). The combined extracts were washed with sodium bicarbonate solution (4%) (1×10 ml) and brine (1×5 ml), dried over Na$_2$SO$_4$, filtered and evaporated. The crude product was purified by silica gel chromatography, using a mixture of 10% MeOH in DCM as eluent, to obtain Compound 10b (0.012 gram, 45% yield).

$^1$H NMR (CDCl$_3$): δ=9.17(s, 1H), 8.8-8.83 (m, 1H), 8.72 (s, 1H), 8.5 (s, 1H), 7.6 (s-br, 1H), 7.3 (s, 1H) 7.037 (m, 1H), 6.27-6.32 (m, 1H), 4.62 (m, 2H), 4.46 (m, 1H), 4.4 (m, 2H), 4.0 (m, 2H), 3.68-3.76 (m, 10H), 3.16-3.18 (m, 2H), 2.31 (s, 6H) ppm.

MS: (m/z)=628.93 (MH+).

Mp=119-120° C.

HRMS (EI): calcd. for C$_{28}$H$_{33}$Cl$_2$F$_2$N$_5$O$_5$: 628.1893; found: 628.1905.

Anal. (C$_{28}$H$_{33}$Cl$_2$F$_2$N$_5$O$_5$.1.5H$_2$O): Calcd. C, 51.29; H, 5.34; N, 10.68; Found. C, 51.71; H, 5.67; N, 9.76.

Compounds 10a and 10c are similarly prepared, using Compounds 38a and 38c as a starting material, respectively.

Compounds 11a-c and 12a-c are similarly prepared, using Compounds 39a-c and 40a-c, as a starting material, respectively.

Figure 3C:
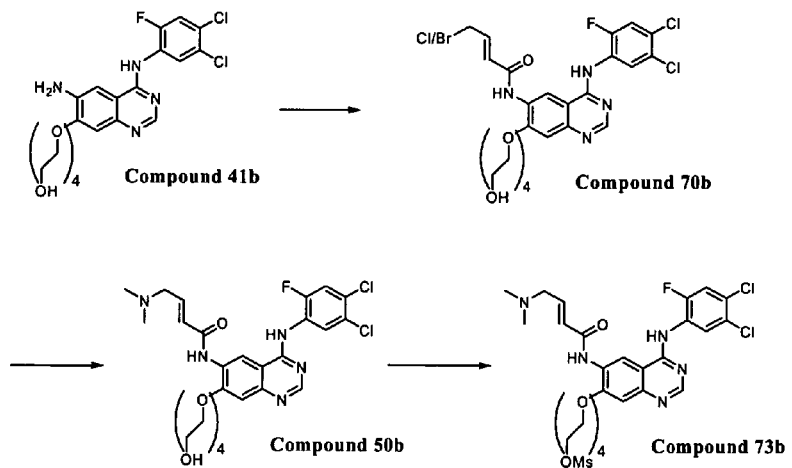

In another representative example, the preparation of Compound 60b is described hereinbelow and is further depicted in FIG. 3c.

Preparation of 4-Bromo/Chloro-but-2-enoic acid[4-(4,5-dichloro-2-fluoro-phenylamino)-7-(2-{2-[2-(2-ethoxy)-ethoxy]-ethoxy}-ethanol) -quinazoline-6-yl]-amide (Compound 70b)

Compound 41b (0.2 gram, 0.39 mmol), prepared as described hereinabove, was dissolved in dry THF (1 ml), and added dropwise to a solution of 4-bromo/chloro-but-2-enoyl chloride (0.13 gram, 0.79 mmol) in THF (1.3 ml) at 0° C. The reaction mixture was stirred for 1 hour, the solvent was thereafter evaporated and the residue was extracted with DCM (3×40 ml) from water. The combined extracts were washed with brine (15 ml), dried (Na$_2$SO$_4$), filtered and evaporated. The crude product was purified by silica gel chromatography, using a mixture of 5% MeOH in DCM as eluent, to obtain Compound 17b (0.11 gram, 42% yield).

$^1$H-NMR (CDCl$_3$): δ=9.19 (s, 1H), 9.14 (s, 1H), 8.8 (d, 1H, J=15.6 Hz), 8.71 (s, 1H), 7.32 (s, 1H), 7.28 (s, 1H), 6.52 (s-br, 1H), 6.47 (s-br, 1H), 4.39 (m, 3H), 4.27-4.29 (m, 1H), 3.4 (m, 3H), 3.61-3.75 (m, 11H).

MS: (m/z)=619.47/663.27 (MH+).

HRMS (EI): calcd. for C$_{26}$H$_{28}$BrCl$_3$FN$_4$O$_6$: 617.1158/661.0627, found: 617.1137/661.0632.

Mp=127-130° C.

Preparation of 4-Dimethylamino-but-2-enoic acid [4-(4,5-dichloro-2-fluoro-phenylamino)-7-(2-{2-[2-(2-ethoxy)ethoxy]-ethoxy}-ethanol)-quinazoline-6-yl]-amide (Compounds 60b)

Compound 70b (0.128 gram, 0.193 mmol) dissolved in THF (2 ml), was added dropwise to a cooled solution of dimethylamine (2 ml) in THF (2M), and diisopropylethylaine (0.386 mmol, 67.3 μl) was added to the solution. The reaction mixture was stirred at 0° C. for 1 hour. The solvent was thereafter evaporated, and the residue was extracted with DCM (3×20 ml). The combined extracts were washed with sodium bicarbonate solution (4%) (1×10 ml) and brine (1×10 ml), dried over Na$_2$SO$_4$, filtered and evaporated. The crude product was purified by silica gel chromatography, using a mixture of 15% MeOH in DCM as eluent, to obtain Compound 60b (0.034 gram, 28% yield).

$^1$H-NMR (CDCl$_3$): δ=9.26 (s, 1H), 9.16 (s, 1H), 8.8 (d, 1H, J=6 Hz), 8.71 (s, 1H), 7.63 (s-br, 1H), 7.32 (m, 1H), 6.46 (m, 1H), 6.41 (m, 1H), 4.37-4.39 (m, 2H), 3.98-4 (m, 2H), 3.59-3.76 (m, 12H), 3.16-3.19 (m, 2H), 2.32 (s, 6H) ppm.

MS: (m/z)=626.73 (MH+).

HRMS (EI): calcd. for C$_{28}$H$_{34}$Cl$_2$FN$_5$O$_6$: 626.1929; found: 626.1948.

Anal. (C$_{28}$H$_{34}$Cl$_2$FN$_5$O$_6$.3H$_2$O): Calcd.: C, 49.41; H, 5.88; N, 10.29; Found. C, 49.44; H, 5.64; N, 9.73.

Mp=120-121° C.

Compounds 60a and 60c are similarly prepared, using Compounds 41a and 41c, as a starting material, respectively.

Similarly, Compounds 61a-c and 62a-c are similarly prepared, using Compounds 42a-c and 43a-c, as starting materials, respectively.

The functional hydroxy group at the terminus of the polyalkylene glycol moiety can be activated by esterification with methanesulfonic acid, as described hereinafter and exemplified in FIG. 3c.

Preparation of 4-Dimethylamino-but-2-enoic acid [4-(4,5-Dichloro-2-fluoro-phenylamino)-Methanesulfonic acid-7-(2-{2-[2-(2-ethoxy)ethoxyl-ethoxy-ethyl ester)-quinazoline-6-yl]-amide (Compound 73b)

Compound 60b (0.015 gram, 0.024 mmol) was dissolved in dichloromethane (1.5 ml) and triethylamine (0.048 mmol, 6.64 μl) was added. Methanesulfonyl chloride (0.048 mmol, 3.7 μl) was then added and the reaction mixture was stirred at room temperature for 1.5 hour. The solvent was thereafter evaporated and the residue was extracted twice with DCM. The combined extracts were washed with brine, dried over sodium sulfate. Compound 73b was thus obtained in 71% yield and had 98% purity, and was used without any further purification.

$^1$H-NMR (CDCl$_3$): δ=9.71 (s, 1H), 9.25 (s, 1H), 8.58 (s, 1H), 8.06-8.09 (m, 1H), 7.56 (s, 1H), 7.32 (d, 1H, J=15 Hz), 6.9-7.05 (m, 2H), 4.32-4.35 (m, 2H), 4.2 (m, 2H), 3.96-3.98 (m, 3H), 3.64-3.72 (m, 9H), 3.08 (s, 3H), 2.92 (s, 6H), 2.84 (s, 2H) ppm.

MS: (m/z)=704.33 (MH+).
HRMS (EI): calcd. for 704.1735; Found: 704.1724

Figure 9:
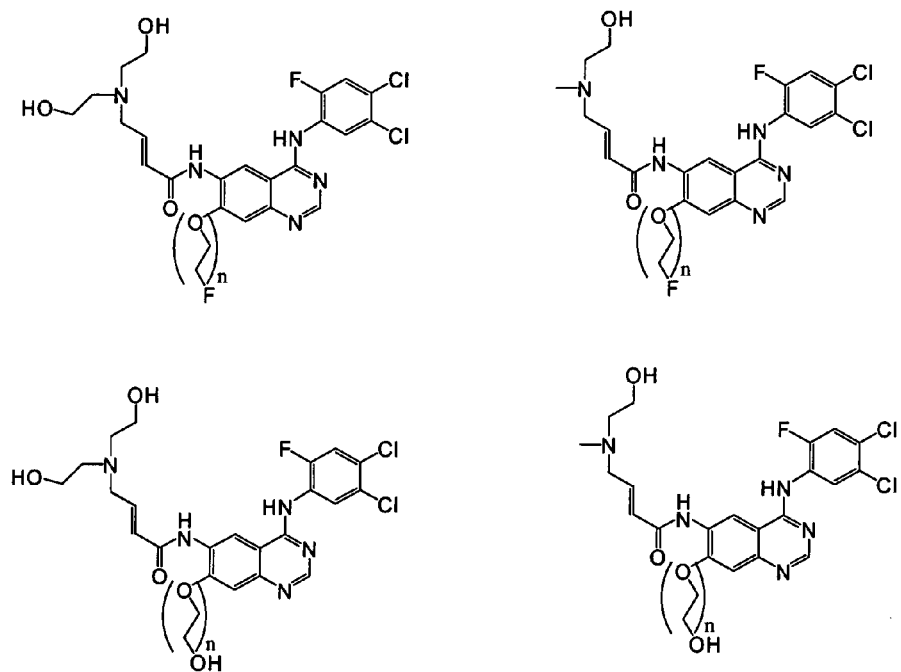
FIG. 9 presents the chemical structures (2D) of exemplary compounds having one or more hydroxy-containing moieties and a polyethylene glycol moiety, according to preferred embodiments of the present invention.

Preparation of Derivatized 4-dimethylamino-but-2-enoic acid [4-(phenylamino)-quinazoline-6-yl]-amide Having a Polyethylene Glycol Moiety and a Hydroxyethyl Moiety or Moieties Attached Thereto The chemical structures of exemplary derivatized 4-dimethylamino-but-2-enoic acid [4-(phenylamino)-quinazoline-6-yl]-amides having a polyethylene glycol moiety and a hydroxyethyl moiety or moieties attached thereto are presented in FIG. 9. Such compounds are prepared, for example, by reacting Compounds 44a-c or 70a-c with ethanol amine or diethanolamine.

As a representative example, (E)-N-(7-(2-fluoroethoxy)-4-(4,5-dichloro-2-fluorophenylamino)quinazolin-6-yl)-4-(bis(2-hydroxyethyl)amino)but-2-enamide was prepared as follows: Compound 44b (0.0088 gram, 0.0013 mmol) dissolved in THF (10 µl), was added dropwise to a cooled solution of diethanolamine (0.026 mmol, 2.53 µl) in THF (10 µl), and DMF (2.64 µl) was added to the solution. The reaction mixture was stirred at 0° C. for 30 minutes, and then heated at 60° C. for additional 30 minutes. The solvent was thereafter evaporated and the residue was extracted with ethyl acetate (3×20 ml). The combined extracts were washed with saturated sodium bicarbonate solution (1×10 ml) and brine (1×5 ml), dried over $MgSO_4$, filtered and evaporated.

MS (m/z): 688.4 (MH+).

Radiosyntheses

Radiosyntheses, using fluorine-18, were carried out on a [$^{18}$F] module (Nuclear-Interface, Munster, Germany).

Generation of Fluorine-18: Fluorine-18 was produced on a cyclotron IBA 18/9 by irradiation of a 2 ml water target using a 17 Mev proton beam on 97%-enriched [$^{18}$O]water by the [$^{18}$O(p,n) $^{18}$F] nuclear reaction and was transferred to the appropriate hot cell.

Generation of carbon-11 $CO_2$: [carbon-11]-$CO_2$ is produced by the $^{14}$N(p, α) $^{11}$C nuclear reaction on a mixture of $N_2$/0.5% $O_2$ as a target.

Generation of carbon-11 methyl iodide: carbon-11 methyl iodide is produced according to a known procedure (Mishani et al., 2001).

Generation of iodine-124 sodium iodide: $^{124}$I-NaI is purchased as a 0.02 M solution from Ritverc GmBH, Russia.

HPLC separations were carried out using a Varian 9012Q pump, a Varian 9050 variable wavelength detector operating at 254 nm and a Bioscan Flow-Count radioactivity detector with a NaI crystal.

The radiolabeled compounds were purified on a reverse phase system using a C18-reverse phase-prep column and the following mobile phase system: 48% $CH_3CN$ in 52% acetate buffer (pH=3.8), at 15 ml/minute flow rate. Eluent fractions (2.5 ml) were collected on a fraction collector (FC205, Gilson). Analysis of formulated radiotracers was performed on C18 column µ Bondapak analytical column, using 40% $CH_3CN$ in 60% acetate buffer (pH=3.8) as elute, at a flow rate of 1.7 ml/min Radiotracers formulation was performed as follows: The product was collected in a vial that contained 50 ml water and 1 ml NaOH (1 M). The solution was passed through a pre-washed (10 ml water) activated C18 cartridge, and washed with 10 ml sterile water. The product was eluted using 1 ml ethanol followed by 5 ml of saline.

Preparation of Radiolabeled 4-anilinoquinazolinyl amides Substituted by a Polyalkylene Glycol Moiety—General Procedure I Radiolabeling of the compounds described herein is performed based on the procedures described in U.S. Pat. Nos. 6,562,319, U.S. patent application Ser. No. 09/802,928 (Publication No. 2004/0265228, recently granted), and WO 04/064718.

Preparation of carbon-11 Labeled Compounds

Carbon-11 labeled compounds are prepared by reacting a 6-amino-4-anilinoquinazoline substituted by a polyalkylene glycol moiety with a carbon-11 labeled α,β-unsaturated acyl chloride, at 0° C. in THF, in the presence of a chemically reactive base such as tertiary amine.

Alternatively, a 6-amino-4-anilinoquinazoline substituted by a polyalkylene glycol moiety is reacted with a reactive α,β-unsaturated carboxylic derivative, which is terminating with a second reactive group, so as to produce a compound substituted by an α,β-unsaturated carboxylic group terminating with the second reactive group, which is then reacted with a reactive substituted alkyl having 1-6 carbon atoms and thereafter with a carbon-11 labeled reactive compound.

Further alternatively, a f 6-amino-4-anilinoquinazoline substituted by a polyalkylene glycol moiety is reacted with a carbon-11 labeled reactive carboxylic derivative substituted at the α position by a leaving group, at 0° C. in THF, in the presence of a chemically reactive base such as tertiary amine.

Preparation of fluorine-18 Labeled Compounds

A fluorine-18 labeled aniline derivative is prepared by reacting a [F-18]fluoride ion with the corresponding dinitrobenzene derivative and then reducing the fluorine-18 labeled fluoronitrobenzene. The fluorine-18 labeled aniline derivative is reacted with 4-chloroquinazoline that is substituted by a first (e.g., nitro) and a second reactive group, so as to produce a reactive fluorine-18 labeled 4-(phenylamino)quinazoline, which is then coupled to a reactive derivative of polyalkylene glycol and reacted with carboxylic acid derivative, as described hereinabove.

Preparation of Radioactive Bromine or Radioactive Iodine Labeled Compounds

Radioactive bromine and radioactive iodine labeled compounds are prepared by reacting a f 6-amino-4-anilinoquinazoline substituted by a polyalkylene glycol, and derivatized by a halogen at the aniline ring, prepared as described hereinabove using a halogen-derivatized aniline, with bis-tributyltin, using tetrakis(triphenylphosphine)palladium as catalyst and reacting thereafter the obtained stanylated product with a radioactive bromine or a radioactive iodine, in the presence of an oxidizing agent, so as to produce a reactive radioactive bromine labeled or radioactive iodine labeled 4-(phenylamino)quinazoline; and reacting the resulting radioactive bromine labeled or radioactive iodine labeled compound with a reactive derivative of carboxylic group, as described herein.

Preparation of Radiolabeled 4-anilinoquinazolinyl amides Substituted by a Polyalkylene Glycol Moiety—General Procedure II In an alternative synthetic pathway, radiolabeled compounds according to the present embodiments are prepared by radiolabeling the polyalkylene glycol moiety. Thus, for example, a 6-nitro-4-anilinoquinazoline substituted by a polyalkylene glycol moiety terminating with a reactive group, prepared as described hereinabove, is converted into a 6-nitro-4-anilinoquinazoline substituted by a polyalkylene glycol derivative terminating with a radioactive group or atom, which is thereafter reacted as described hereinabove to produce the final product.

Preparation of fluorine-18 Labeled Compounds

A 6-nitro-4-anilinoquinazoline substituted by a polyalkylene glycol derivative terminating with a reactive group, prepared as described hereinabove, is reacted with a [F-18]fluoride ion, so as to produce a [F-18]-labeled 6-nitro-4-anilinoquinazoline substituted by a radiolabeled polyalkylene glycol moiety, which is then reacted with hydrazine hydrate and Ra—Ni so as to produce a [F-18]-labeled 6-amino-4-anilinoquinazoline substituted by the radiolabeled polyalkylene glycol moiety. The [F-18]-labeled compound is thereafter reacted with a reactive carboxylic acid derivative, as described herein, so as to produce the final product.

Preparation of Radioactive Bromine or Radioactive Iodine Labeled Compounds

A 6-nitro-4-anilinoquinazoline substituted by a polyalkylene glycol derivative terminating with a halide (halogen) group, prepared as described hereinabove, is reacted with bistributyltin, using tetrakis(triphenylphosphine)palladium as catalyst and the obtained stanylated product is thereafter reacted with a radioactive bromine or a radioactive iodine, in the presence of an oxidizing agent, so as to produce a radioactive bromine labeled or radioactive iodine labeled 6-nitro-4-anilinoquinazoline substituted by a radiolabeled polyalkylene glycol moiety. The radiolabeled compound is then reacted with hydrazine hydrate and Ra—Ni so as to produce a radiolabeled 6-amino-4-anilinoquinazoline substituted by a radiolabeled polyalkylene glycol moiety, which is thereafter reacted with a reactive carboxylic acid derivative, as described herein, so as to produce the final product.

Preparation of fluorine-18 Labeled (4,5-Dichloro-2-fluoro-phenyl)-{7-[2-(2-fluoro-ethoxy)-ethoxy]-6-nitro-quinazolin-4-yl}-amine (fluorine-18 Labeled Compound 35a)

[$^{18}$O]H$_2$O/$^{18}$F$^-$, generated as described hereinabove, was trapped and then transferred through an ion exchange column (pre-activated with 0.8 ml EtOH and 3 ml HPLC water), and eluted with a 0.5 ml solution of potassium carbonate (2.5 mg/0.5 ml water) and 1 ml Kryptofix®222 (18 mg/ml CH$_3$CN). The solvent was thereafter removed by azeotropic distillation at 95° C. under reduced pressure for 3 minutes, to thereby afford an $^{18}$F-fluoride ion. A solution of Compound 32a (6 mg/0.4 ml DMSO) was added to the reactor containing the dried $^{18}$F-fluoride ion and the resulting solution was heated at 120° C. for 10 minutes. The reaction mixture was thereafter cooled to 30° C. 13 ml of water were added thereto, and the obtained solution was loaded on a C-18 cartridge (Waters Sep-Pak, preactivated with 5 ml EtOH and 10 ml of sterile water). Fluorine-18 labeled Compound 35a was eluted with EtOH (2 ml) and the product, in 60% radiochemical yield (decay corrected), was collected in a vial in the module, after 35 minutes.

Fluorine-18 labeled Compound 35a was then injected to a reverse-phase HPLC C-18 analytical column, using as a mobile phase a mixture of 55% acetate buffer 0.1M (pH=3.8) and 45% CH$_3$CN, at a flow rate of 1 ml/minute), and its purity was determined as 93% radiochemical purity (retention time=25 minutes).

Preparation of fluorine-18 Labeled 4,5-Dichloro-2-fluoro-phenyl)-[7-(2-{2-[2-(2-fluoro-ethoxy)-ethoxy]-ethoxy}-ethoxy)-6-nitro-quinazolin-4-yl]-amine (fluorine-18 Labeled Compound 35b)

Fluorine-18 Compound 35b was prepared as described hereinabove for Compound 35a, using Compound 29b as the starting material. Radiochemical yield was 62% (decay corrected) and radiochemical purity was 97% (retention time=24.4 minutes).

Preparation of fluorine-18 Labeled (4,5-Dichloro-2-fluoro-phenyl)-(7-{2-[2-(2-{2-[2-(2-(fluoro-ethoxy)-ethoxy]-ethoxy}-ethoxy)-ethoxy]-ethoxy}-6-nitro-quinazolin-4-yl)-amine (fluorine-18 Labeled Compound 35c)

Fluorine-18 labeled Compound 35c was prepared as described hereinabove for Compound 35a, using Compound 29c as the starting material. Radiochemical yield was 65% (decay corrected) and radiochemical purity was 93% (retention time=24.8 minutes).

Preparation of fluorine-18 Labeled (3-iodophenyl)-{7-[2-(2-fluoro-ethoxy)-ethoxy]-6-nitro-quinazolin-4-yl}-amine (fluorine-18 Labeled Compound 36a), fluorine-18 Labeled (3-iodophenyl)-[7-(2-{2-[2-(2-fluoro-ethoxy)-ethoxy]-ethoxy}-ethoxy)-6-nitro-quinazolin-4-yl]-amine (fluorine-18 Labeled Compound 36b) and fluorine-18 Labeled (3-iodophenyl)-(7-{2-[2-(2-{2-[2-(2-(fluoro-ethoxy)-ethoxy]-ethoxy}-ethoxy)-ethoxy]-ethoxy}-6-nitro-quinazolin-4-yl)-amine (fluorine-18 Labeled Compound 36c)

Fluorine-18 labeled Compounds 36a, 36b and 36c are prepared as described hereinabove for Compounds 35a-c, using Compounds 30a-c, respectively, as starting materials.

Preparation of fluorine-18 Labeled (3-bromophenyl)-{7-[2-(2-fluoro-ethoxy)-ethoxy]-6-nitro-quinazolin-4-yl}-amine (fluorine-18 Labeled Compound 37a), fluorine-18 Labeled (3-bromophenyl)-[7-(2-{2-[2-(2-fluoro-ethoxy)-ethoxy]-ethoxy}-ethoxy)-6-nitro-quinazolin-4-yl]-amine (fluorine-18 Labeled Compound 37b) and fluorine-18 Labeled (3-bromophenyl)-(7-{2-[2-(2-{2-[2-(2-(fluoro-ethoxy)-ethoxy]-ethoxy}-ethoxy)-ethoxy]-ethoxy}-6-nitro-quinazolin-4-yl)-amine (fluorine-18 Labeled Compound 37c)

Fluorine-18 labeled Compounds 37a, 37b and 37c are prepared as described hereinabove for Compounds 35a-c, using Compounds 31a-c, respectively, as starting materials.

Preparation of fluorine-18 Labeled N$^4$-(4,5-dichloro-2-fluoro-phenyl)-7-[2-(2-fluoro-ethoxy)-ethoxy]-quinazoline-4,6-diamine (fluorine-18 Labeled Compound 38a)

Hydrazine monohydrate (200 μl) was added to a reactor containing a 9:1 ethanol/water solution (200 μl) and Ra—Ni (400 µl). A solution of fluorine-18 labeled Compound 35a in ethanol was thereafter added and the resulting mixture was heated at 60° C. for 7 minutes, to give fluorine-18 labeled Compound 38a in 37% radiochemical yield (decay corrected).

Fluorine-18 labeled Compound 38a was diluted with water (10 ml) and the solution was passed through a C-18 cartridge, the column was dried under argon for 5 minutes, and the product was eluted with 2 ml of dry THF and collected in a vial.

The radiochemical purity was determined by a reverse-phase HPLC C-18 analytical column using as a mobile phase a mixture of 55% acetate buffer 0.1M (pH=3.8) and 45% $CH_3CN$, at a flow rate of 1 ml/minute), as 90% radiochemical purity (retention time=14 minutes).

Preparation of fluorine-18 Labeled $N^4$-(4,5-Dichloro-2-fluoro-phenyl)-(2-{2-[2-(2-Fluoro-ethoxy)-ethoxy]-ethoxy}-ethoxy)-quinazoline-4,6-diamine (fluorine-18 Labeled Compound 38b)

Fluorine-18 labeled Compound 38b was prepared as described hereinabove for Compound 38a, using Compound 35b as the starting material.

Radiochemical yield was 40% (decay corrected) and radiochemical purity was 87% (retention time=17 minutes).

Preparation of fluorine-18 Labeled $N^4$-(4,5-Dichloro-2-fluoro-phenyl)-7-{2-[2-(2-{2-[2-(2-fluoro-ethoxy)-ethoxy]-ethoxy}-ethoxy)-ethoxy]-ethoxy}-quinazoline-4,6-diamine (fluorine-18 Labeled Compound 38c)

Fluorine-18 labeled Compound 38c was prepared as described hereinabove for Compound 38a, using Compound 35c as the starting material.

Radiochemical yield was 50% (decay corrected) and radiochemical purity was 90% (retention time=14.26 minutes).

Preparation of fluorine-18 labeled $N^4$-(3-iodophenyl)-7-[2-(2-fluoro-ethoxy)-ethoxy]-quinazoline-4,6-diamine (fluorine-18 Labeled Compound 39a), fluorine-18 Labeled $N^4$-(3-iodophenyl)-(2-{2-[2-(2-Fluoro-ethoxy) -ethoxy]-ethoxy}-ethoxy)-quinazoline-4,6-diamine (fluorine-18 Labeled Compound 39b) and fluorine-18 Labeled $N^4$-(3-iodophenyl)-7-{2-[2-(2-{2-[2-(2-fluoro-ethoxy)-ethoxy]-ethoxy}-ethoxy)-ethoxy]-ethoxy}-quinazoline-4,6-diamine (fluorine-18 Labeled Compound 39c)

Fluorine-18 labeled Compounds 39a, 39b and 39c are prepared as described hereinabove for Compounds 38a-c, respectively, using. Compounds 36a-c, respectively, as starting materials.

Preparation of fluorine-18 Labeled $N^4$-(3-bromophenyl)-7-[2-(2-fluoro-ethoxy)-ethoxy]-quinazoline-4,6-diamine (fluorine-18 Labeled Compound 40a), fluorine-18 Labeled $N^4$-(3-bromophenyl)-(2-{2-[2-(2-Fluoro-ethoxy)-ethoxy]-ethoxy}-ethoxy)-quinazoline-4,6-diamine (fluorine-18 Labeled Compound 40b) and fluorine-18 Labeled $N^4$-(3-bromophenyl)-7-{2-[2-(2-{2-[2-(2-fluoro-ethoxy)-ethoxy]-ethoxy}-ethoxy)-ethoxy]-ethoxy}-quinazoline-4,6-diamine fluorine-18 Labeled (Compound 40c)

Compounds 40a, 40b and 40c are prepared as described hereinabove for Compounds 38a-c, respectively, using Compounds 37a-c, respectively, as starting materials.

Preparation of fluorine-18 Labeled Compounds 1-12(a-c)

Fluorine-18 labeled Compounds 1-12 (a-c) are prepared from fluorine-18 labeled Compounds 38a-c, 39a-c and 40a-c, using the general procedures described hereinabove.

Figure 4:
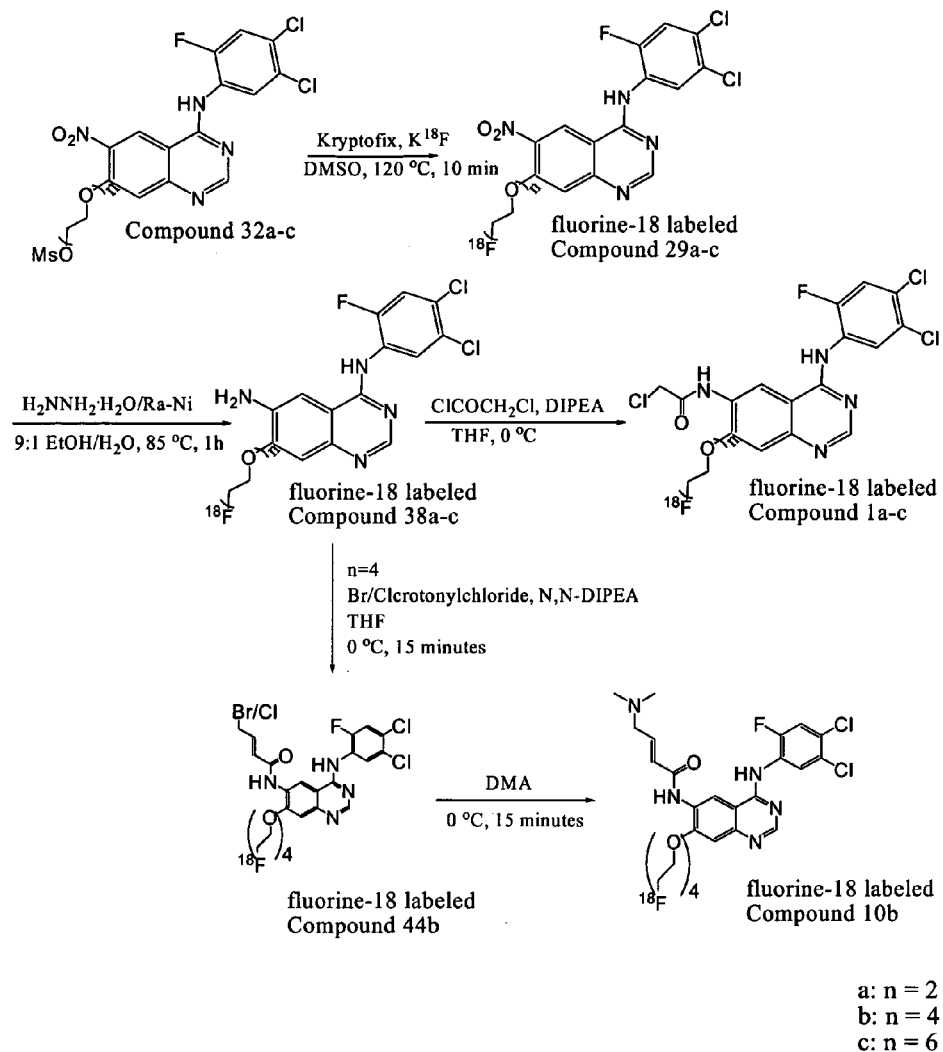
FIG. 4 is a scheme presenting a representative radiosynthetic route for preparing representative examples of fluorine-18 labeled compounds according to the present embodiments (fluorine-18 labeled Compounds 1a-c and 10b)

As a representative example, the preparation of fluorine-18 labeled Compounds 1a-c is depicted in FIG. 4.

Preparation of fluorine-18 Labeled 2-Chloro-N-{4-(4,5-Dichloro-2-fluoro-phenylamino)-7-[2-(2-fluoro-ethoxy)-ethoxy]-quinazoline-6-yl}-acetamide (fluorine-18 labeled Compound 1a)

A solution of fluorine-18 labeled Compound 38a in THF (2 ml) was cooled to 0° C. for 5 minutes, and a solution of N,N-diisopropylethylamine (DIPEA) (40 µl/ml THF, 200 µl), and a solution of chloroacetylchloride (100 µl/0.5 ml THF, 600 µl) were added to the vial. The reaction mixture was stirred for 20 minutes at 0° C. Monitoring the radiochemical yield was performed by evaporating the solvent to a volume of 300 µl, dissolving the residue in a 1:1 mixture of $CH_3CN/H_2O$ and purifying the sample by HPLC (using a reversed-phase C-18 semi-preparative column, a mixture of 53% ammonium formate 0.1 M and 47% acetonitrile as a mobile phase, at flow rate of 5 ml/minute). Retention time of fluorine-18 labeled Compound 1a was 24 minutes. Fluorine-18 labeled Compound 1a was obtained after 3 hours in a radiochemical yield of 22% (decay corrected).

Radiochemical purity and specific activity were measured by HPLC on a C-18 analytical column (using a mixture of 53% ammonium formate 0.1 M and 47% acetonitrile, at a flow rate of 0.7 ml/minute). Fluorine-18 labeled Compound 1a was 8.8 minutes and radiochemical purity was 99.5%.

Specific activity was determined using a calibration curve. The UV peak intensity of purified fluorine-18 labeled Compound 1a was compared to that of the non-radiolabeled Compound 1a at known concentrations. The specific activity of fluorine-18 labeled Compound 1a was 4 Ci/mmol (n=3).

Preparation of fluorine-18 Labeled 2-Chloro-N-[4-(4,5-Dichloro-2-fluoro-phenylamino)-7-(2-{2-[2-(2-fluoro-ethoxy)-ethoxy]-ethoxy}-ethoxy)-quinazoline-6-yl]-acetamide (fluorine-18 Labeled Compound 1b)

Fluorine-18 labeled Compound 1b was prepared as described hereinabove for fluorine-18 labeled Compound 1a, using Compound 38b as a starting material. Radiochemical yield was 25% (decay corrected); radiochemical purity was 99.9%, HPLC retention time was 9 minutes, and specific activity was 2.74 Ci/mmol (n=3).

Preparation of fluorine-18 Labeled 2-Chloro-N-(4-(4,5-Dichloro-2-fluoro-phenylamino)-7-{2-[2-(2-{2-[2-(2-fluoro-ethoxy)-ethoxy]-ethoxy}-ethoxy)-ethoxy]-ethoxy}-quinazoline-6-yl)-acetamide (fluorine-18 Labeled Compound 1c)

Fluorine-18 labeled Compound 1c was prepared as described hereinabove for fluorine-18 labeled Compound 1a, using Compound 38c as a starting material. Radiochemical yield was 32% (decay corrected); radiochemical purity was 99.4%, retention time was 9.56 min, and specific activity was 0.9 Ci/mmol (n=3).

In another representative example, the preparation of fluorine-18 labeled Compound 10b is depicted in FIG. 4.

Preparation of fluorine-18 Labeled 4-Bromo/Chloro-but-2-enoic acid[4-(4,5-dichloro-2-fluoro-phenylamino)-7-(2-{2-[2-(2-fluoro-ethoxy)-ethoxy]-ethoxy}-ethoxy)-quinazoline-6-yl]-amide (fluorine-18 Labeled Compound 44b)

Fluorine-18 labeled Compound 38b was eluted with dry THF (2 ml) onto a conical vial maintained at 0° C. 300 μL of N,N-diisopropylethylamine in THF (40 μl/ml), and 1.5 ml of Br/Cl-crotonylchloride in THF (150 mg/1.5 ml) were added and the reaction mixture was stirred for 15 minutes at 0° C., and used for the next step without any further treatment. The identity of the product was analyzed by injection of an aliquot onto a C-18 analytical column (acetate buffer 0.1M (pH=3.8): $CH_3CN$ 50:50 (v/v), flow=1 ml/minute): retention time=22.67 minutes (first peak), retention time=25.04 minutes (second peak).

Preparation of fluorine-18 Labeled 4-Dimethy-lamino-but-2-enoic acid[4-(4,5-dichloro-2-fluoro-phenylamino)-7-(2-{2-[2-(2-fluoro-ethoxy)ethoxy]-ethoxy}-ethoxy)-quinazoline-6-yl]-amide (fluorine-18 Labeled Compound 10b)

Dimethylamine (1.5 ml) in THF (2.0 M) was added to the solution containing fluorine-18 labeled Compound 44b at 0° C. and the reaction proceeded for 15 minutes. The solvent was thereafter evaporated under argon to a volume of 500 μl, and a mixture of $CH_3CN:H_2O$ 50:50 (v/v) was thereafter added. The fluorine-labeled crude product was purified by a HPLC reversed-phase C-18 column (retention time=18 minutes, ammonium formate 0.1 M:acetonitrile 53:47 (v/v), flow=7 ml/minute), and was obtained after a total synthesis time, including purification and formulation of 3.5 hours, with a 15% radiochemical yield and specific activity of 1,890 Ci/mmol, and 98% radiochemical purity (n=15).

As shown in FIG. 4, flurine-18 labeled Compounds 1a-c and 10b are obtained in a three-step radiosynthesis, while the first and the second steps are both performed in two automated commercial modules (Nuclear Interface) associated with an automated procedure that was developed for the labeling and the reduction procedures. The first radiochemical step involves radiolabeling of Compounds 32a-c with fluorine-18 and is performed in DMSO at 120° C. for 10 minutes, using Kryptofix®[222] to give the desired fluorine-18 labeled Compounds 35a-c in a radiochemical purity higher than 90%, and radiochemical yields of 60%, 62% and 65%, decay corrected, respectively). The second radiochemical step involves the reduction of the nitro group to amine, and is performed with hydrazine monohydrate and Ra—Ni at 60° C. for 10 minutes, to afford fluorine-18 labeled Compounds 38a-c in a radiochemical purity higher than 90%, and radiochemical yields of 37%, 40% and 50% decay corrected, respectively). The final step involves condensation with chloroacetyl chloride in the presence of N,N-DIPEA. Purification by semi-preparative HPLC column gave fluorine-18 labeled Compounds 1a-c in a radiochemical purity higher than 99% and radiochemical yields of 22%, 25% and 32% (decay corrected), respectively.

Fluorine-18 labeled Compounds 38a-c are alternatively reacted with bromo/chloro crotonylchloride in the presence of diisopropylethylamine at 0° C. followed by reaction with dimethylamine, to thereby provide fluorine-18 labeled Compound 10b (fluorine-18 labeled ML04). The crude product is purified by semi-preparative HPLC column to give the fluorine-18 labeled compound with a radiochemical purity >99%, decay corrected total radiochemical yield of 15-32%, specific activity of 2,000-4,000 Ci/mmol (n=15), and a total radiosynthesis time of approx. 3 hours, including purification and formulation.

Preparation of Radiolabeled 4-anilinoquinazolinyl amides Substituted by a Polyalkylene Glycol Moiety—General Procedure III (One-Step Radiosyntheses)

In another alternative synthetic pathway, radiolabeled compounds according to the present embodiments are prepared by radiolabeling the polyalkylene glycol moiety in a one-step radiosynthesis. Thus, for example, a 6-nitro-4-anilinoquinazoline substituted by a polyalkylene glycol moiety terminating with a hydroxy group, prepared as described hereinabove, is converted into a corresponding 6-nitro-4-anilinoquinazoline substituted by a polyalkylene glycol derivative terminating with a hydroxy group, which is thereafter reacted as described hereinabove to produce [4-(phenylamino)-quinazoline-6-yl]amides substituted by the polyalkylene glycol moiety. The hydroxy group in the polyalkylene glycol moiety is optionally and preferably activated and is then reacted with a radioactive atom, so as to produce the final radiolabeled product.

Preparation of fluorine-18 Labeled Compounds

A [4-(phenylamino)-quinazoline-6-yl]amide substituted by a polyalkylene glycol moiety terminating with hydroxy group, prepared as described hereinabove, is activated by e.g., esterification with methanesulfonic acid, and the resulting ester is reacted with a [F-18]fluoride ion, so as to produce the final product.

Preparation of Radioactive bromine or Radioactive Iodine Labeled Compounds

A [4-(phenylamino)-quinazoline-6-yl]amide substituted by a polyalkylene glycol derivative terminating with a halide (halogen) group, prepared as described hereinabove, is reacted with bistributyltin, using tetrakis(triphenylphosphine)palladium as catalyst and the obtained stanylated product is thereafter reacted with a radioactive bromine or a radioactive iodine, in the presence of an oxidizing agent, so as to produce a radioactive bromine labeled or radioactive iodine labeled [4-(phenylamino)-quinazoline-6-yl]amide substituted by a radiolabeled polyalkylene glycol moiety.

Figure 8:
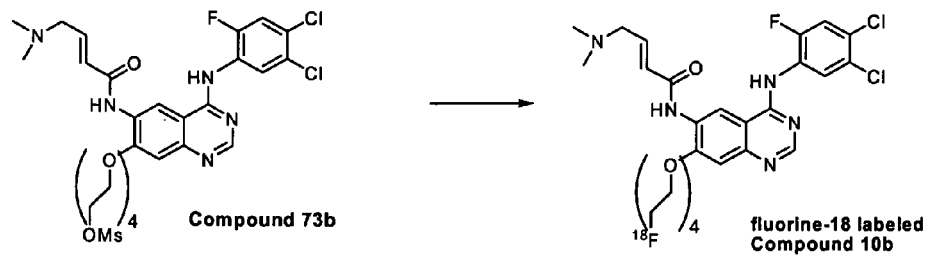
FIG. 8 is a scheme presenting a representative one-step radiosynthetic route for preparing a representative example of a fluorine-18 labeled compound according to the present embodiments (fluorine-18 labeled Compound 1b)

As a representative example, the preparation of fluorine-18 labeled Compound 10b is described hereinbelow and is depicted in FIG. 8.

Preparation of fluorine-18 Labeled 4-Dimethylamino-but-2-enoic acid [4-(4,5-dichloro-2-fluorophenylamino)-7-(2-{2-[2-(2-fluoro-ethoxy)ethoxy]-ethoxy}-ethoxy)-quinazoline-6-yl]-amide (fluorine-18 Labeled Compound 10b)

[$^{18}$O]H$_2$O/$^{18}$F$^-$ was trapped and then transferred through an ion exchange column (preactivated with 0.8 ml EtOH and 3 ml HPLC water) and by elution with 0.5 ml potassium carbonate (2.5 mg/0.5 ml) and 1 ml Kryptofix® 222 (18 mg/ml CH$_3$CN). The solvent was removed by azeotropic distillation at 95° C. under reduced pressure for 3 minutes. A solution of the mesylate derivative Compound 73b (5 mg/0.4 ml DMSO) was added to the reactor containing the dried $^{18}$F. The solution was heated at 100° C. for 10 minutes. The reaction mixture was cooled to 30° C., and 13 ml of water was added to the solution, and loaded on a C-18 cartridge (Waters Sep-Pak, preactivated with 5 ml EtOH and 10 ml of sterile water). Fluorine-18 labeled Compound 10b was eluted with EtOH (1 ml) to the collect vail in the module that contains acetonitrile/water (1 ml), and was injected to a semi-preparative C-18 column (50% ammonium formate, 48% acetonitrile, 2% THF, flow=12 ml/minute). The product was obtained with retention time of 26 minutes, 40% radiochemical purity, 7% radiochemical yield (decay corrected), and specific activity of 1500 Ci/mmol (n=2).

Characterization

Material and Methods:
Preliminary studies were conducted in order to characterize the lipophilicity and water solubility of the novel compounds, as follows:

Partition coefficient determination: Compounds 1a-c and 10b, ML04 and ML05 (3 mg) were dissolved in sodium phosphate buffer (0.1 M, pH 7.4, 5 ml) and 1-octanol (1 ml) and the resulting mixture was vortexed for 2 minutes, filtered, and maintained at room temperature for 10 minutes. The reaction mixture was then centrifuged at 4000 g for 10 minutes. Fifty (50) μl portions were taken from the organic (1-octanol) and from the aqueous (buffer) layers, and were dissolved in 0.45 ml acetonitrile. The samples were analyzed by HPLC system (C-18 analytical column, a mixture of 55% acetonitrile:45% acetate buffer 0.1 M, pH 3.8 as a mobile phase, flow rate of 1 ml/minute). The partition coefficients (Log P) were determined by the concentration ratio of the tested compound in the organic phase and the aqueous phase. Measurements were performed in triplicate.

Water Solubility Determination:
DMSO (1 ml) and MOPS buffer pH 7.4 (1 ml) were separately added to test tubes containing the tested compound (Compounds 1a-c and 10b, ML04 or ML05), such that for each compound, two test tubes were prepared. The tubes were sonicated at room temperature for 20 minute, left intact for 10 minutes, and were then filtered through a 0.45 μm filter. Each of the DMSO solutions was diluted 10-folds with DMSO. A 50 μl sample of each solution was analyzed by HPLC (using C-18 analytical column, a mixture of 55% CH$_3$CN:45% acetate buffer 0.1 M, pH 3.8, as a mobile phase at a flow rate of 1 ml/minute, and a UV detector operated at 254 nm). Measurements were performed in triplicate.

Experimental Results:
The preliminary data obtained clearly indicate that substituting anilinoquinazolines with polyalkylene glycol at position 7 of the quinazoline significantly serves as an efficient and flexible tool for adjusting the lipophilicity and the solubility and biostability of anilinoquinazolines as desired. Thus, these features can be controlled, for example, by increasing/decreasing the length of the alkylene chain in the polyalkylene glycol moiety, by manipulating the chemical structure of the polyalkylene glycol moiety and by manipulating the chemical nature of the end group of the polyalkylene glycol moiety.

It is noteworthy that Compound 10b was found to exhibit a decreased lipophilicity (Log P=3.7), as compared with ML-04 (a corresponding molecule devoid of an alkylene glycol moiety and having Log P of 3.9) and a significantly improved solubility (3.5 μg/ml) as compared with ML04 (0.14 μg/ml).

Activity Assays

Materials and Methods:
Irreversibility Test Protocol: The inhibitory potency of compounds 1a-c, as well as the irreversible nature of EGFR inhibition thereof were evaluated in intact A431 cells, according to published procedures (Smail et al., 1999). In brief, A431 human epidermoid vulval carcinoma were grown in six-well plates for 48 hours and further maintained in serum-free media for additional 18 hours. Duplicate sets of cells were incubated with increasing concentrations of the tested inhibitor for one hour. One set of the cells was thereafter stimulated with EGF, immediately after removal of the tested inhibitor. Another set of the cells was washed to remove the inhibitor, and EGF stimulation was carried out 8 hours after removal of the inhibitor from the medium. Cell lysates were prepared and loaded onto SDS-PAGE (8% acryl amide) for Western Blot analysis, and the extent of EGFR phosphorylation was evaluated by measuring the signal intensity of the corresponding phosphotyrosine band using a mix of anti-phosphotyrosine antibodies, PY20 (Santa Cruz Biotechnology Inc.) and 4G10 (produced from Su4G10 hybridoma cells). The degree of EGFR phosphorylation was measured for each set of cells and the IC$_{50}$ values of Compounds 1a-c and 10b, vis-à-vis the level of EGFR's phosphotyrosine content were determined. A minimum of two different assays with similar results were considered. Each experiment was performed in duplicates. According to this assay, an 80% inhibition of phosphorylation (or more), 8 hour after removal of the inhibitor, compared to the 1 hour control, suggested that the compound was irreversible, whilst a 20-80% inhibition classified the compound as a partially-irreversible one.

Cell growth inhibition: The effect of the compounds presented herein on cell growth was tested in human glioblastoma U87MG wt EGFR and U87MG parental cell lines, each expressing EGFR to a different extent.

Cells were seeded in 96-well plates and grown in a DMEM medium supplemented with 10% FCS and antibiotics (penstrep). Twelve hours post seeding, the tested compound (Compound 1a, 1b or 1c) was added to the growth medium of the cells at increasing concentrations, in a 0.1% ethanol and 0.05% DMSO vehicle (percentages representing final concentrations). Next, 24 hours following addition of the tested inhibitor to the medium, cells in one plate were fixed in 0.5% gluteraldehyde for 10 minutes at room temperature, rinsed thrice with doubly distilled water (DDW) and left to dry overnight in a hood. The remaining plates were similarly treated in 24 hours intervals, during additional four days. The plates were thereafter wetted with borate buffer (0.1 M, pH 8.5, 200 µl/well) and incubated with methylene blue (0.1% in 0.1 M borate buffer, 200 µl/well) while shaking, for 1 hour at room temperature. Residual amounts of methylene blue were fully removed from the plates by repeatedly soaking in DDW, and thereafter drying overnight in a hood. HCl (0.1 M, 200 µl/well) was then added to extract the stain, and the plates were analyzed in an ELISA reader at a wavelength of 630 nm.

Experimental Results:

The inhibitory potency of exemplary compounds according to the present embodiments, as well as the extent of their irreversible inhibition of the EGFR were first evaluated in intact A431 cells, using the protocol described hereinabove. The $IC_{50}$ values were determined by the extent of EGFR phosphorylation at each inhibitor concentration either immediately after or 8 hours post removal of the tested inhibitor from the medium.

Figure 5A:
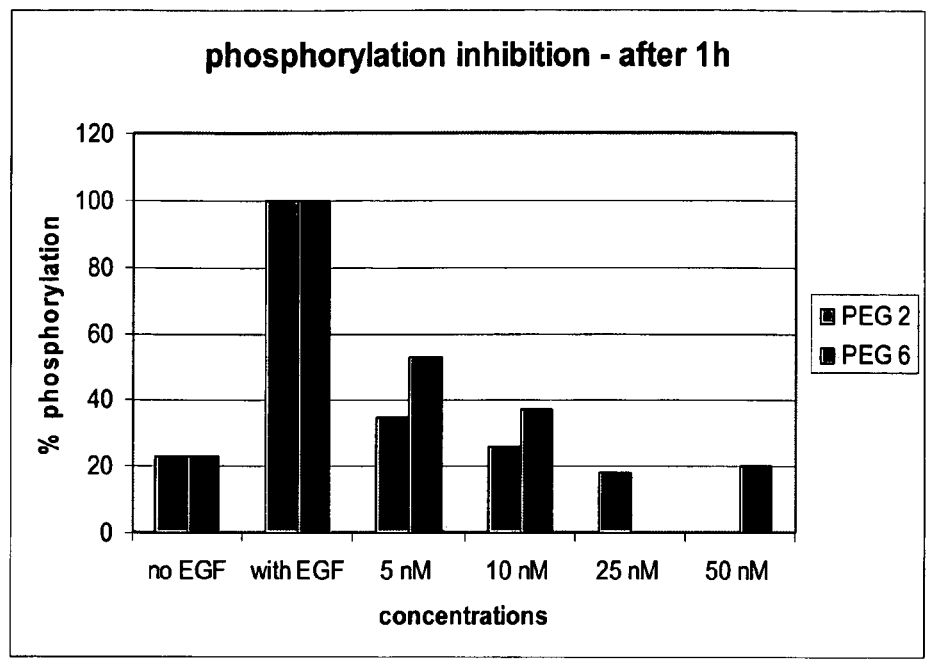
FIGS. 5*a-b* are bar graphs presenting the EGFR autophosphorylation level in A431 cells following incubation with various concentrations of Compounds 1a (purple bars, denoted as PEG 2) and Compound 1c (violet bars, denoted as PEG 6) and EGF stimulation-lysis after 1 hour incubation (FIG. 5*a*) and following 8 hours post-incubation in an inhibitor-free media (FIG. 5*b*)
Figure 5B:
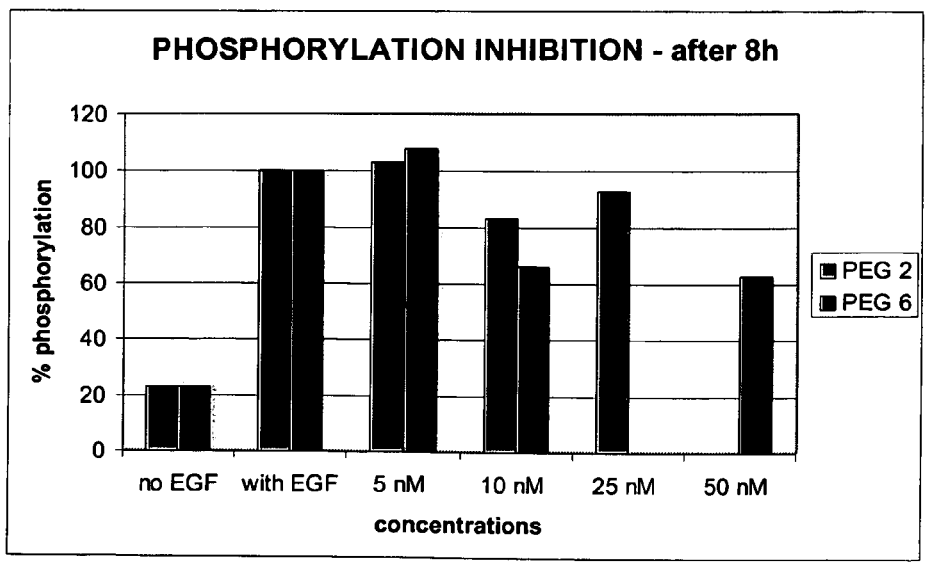

The results obtained for Compounds 1a and 1c are presented in FIGS. 5a (EGF stimulation immediately after removal of the inhibitor) and 5b (EGF stimulation 8 hours after removal of the inhibitor), and clearly indicate the ability of the compounds described herein to irreversibly bind to the EGFR.

Figure 6A:
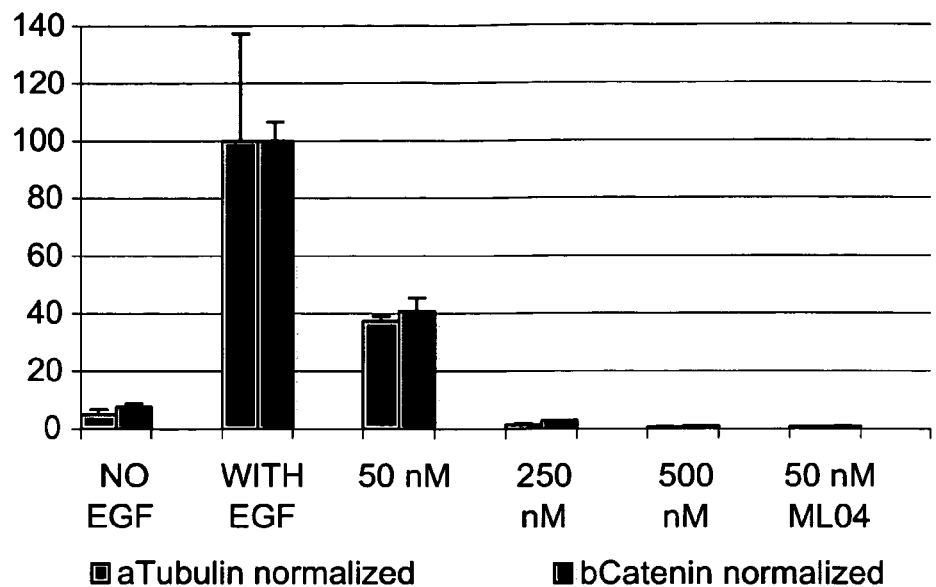
FIGS. 6*a-b* are bar graphs presenting the EGFR autophosphorylation level in A431 cells following incubation with various concentrations of Compounds 1b and EGF stimulation-lysis after 1 hour incubation (FIG. 6*a*) and following 8 hours post-incubation in an inhibitor-free media (FIG. 6*b*) (results were normalized using alpha-tubulin (orange bars) and beta-catenin (brown bars) as a reference)
Figure 6B:
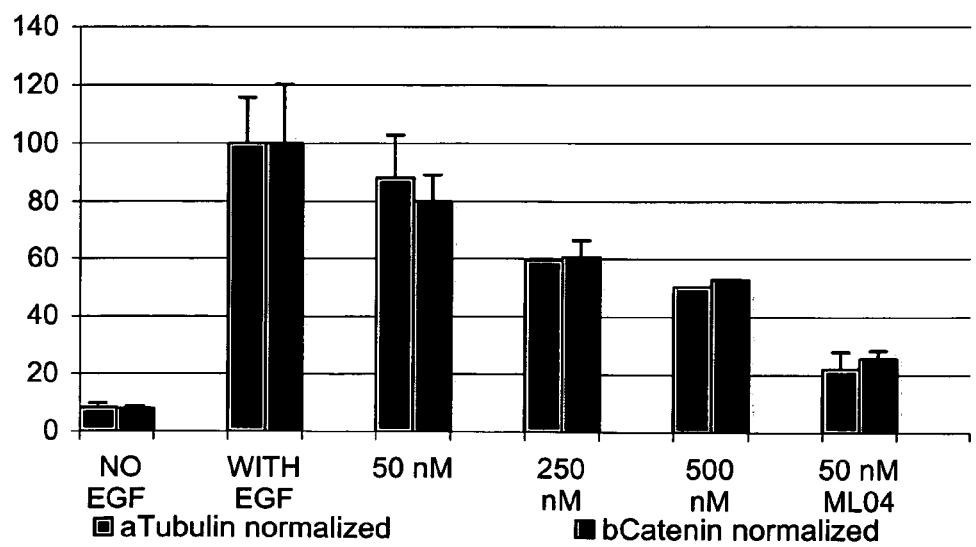

The results obtained for Compound 1b, upon normalization using alpha-tubulin and beta-catenin as references, are presented in FIGS. 6a (EGF stimulation immediately after removal of the inhibitor) and 6b (EGF stimulation 8 hours after removal of the inhibitor), and further clearly indicate the ability of the compounds described herein to irreversibly bind to the EGFR.

The $IC_{50}$ values of compounds 1a-c, vis-à-vis the level of EGFR's phosphotyrosine content, were 5-40 nM. The irreversible inhibitory characteristic was somewhat effected. Compound 10b, however, showed a preserved potency, yielding an $IC_{50}$ of 5 nM, and an irreversible inhibitory characteristic.

Manipulating the chemical structure and chain length of the polyalkylene glycol moiety may further affect the nature and extent of binding to the receptor (e.g., to cys-773 on the receptor binding site). The inhibitory effect of the compounds described herein on cell growth was tested with human glioblastoma U87MG wt EGFR and U87MG parental cells, which express EGFR to different extents.

Figure 7:
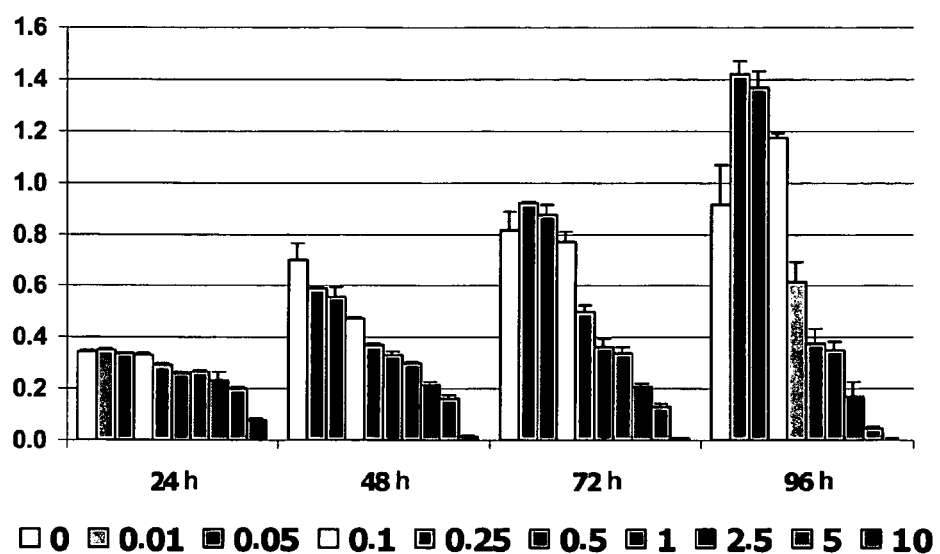
FIG. 7 presents bar graphs demonstrating the inhibitory effect of various concentrations of Compound 1b (denoted as PEG-ML05) on cell growth of U87MG wt EGFR cells following 24 hours, 28 hours, 72 hours and 96 hours incubation.

The obtained results demonstrated a high inhibition potency of the compounds, with a cell-growth median inhibitory concentration of 0.5-1 µM for both cell lines. FIG. 7 presents, for example, the data obtained in U87MG wt EGFR cells upon incubation with various concentration of Compound 1b.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

List of References Cited

Alauddin, M. M., and Conti, P. S. (1998). Synthesis and preliminary evaluation of 9-(4-[$^{18}$F]-fluoro-3-hydroxymethylbutyl)guanine([$^{18}$F]FHBG): A new potential imaging agent for viral infection and gene therapy using PET. Nucl. Med. Biol. 25, 175-80.

Artega, C. L. (2001). The epidermal growth factor receptor: from mutant oncogene in nonhuman cancers to therapeutic target in human neoplasia, J. Clin. Oncol. 19, 32-40.

Artega, C. L., Ramsey, T. T., Shawver, L. K., and Guyer, C. A. (1997). Unliganded epidermal growth factor receptor dimerization induced by direct interaction of quinazolines with the ATP binding site. J. Biol. Chem. 272, 23, 247-54.

Baselga, J., and Averbuch, S. D. (2000). ZD1839 ('Iressa') as an anticancer agent. Drugs, 60 Suppl 1, 33-40; discussion 41-2.

Ben-David, I., Rozen, Y., Ortu, G., and Mishani, E. (2003). Radiosynthesis of ML03, a novel positron emission tomography biomarker for targeting epidermal growth factor receptor via the labeling synthon: [C11] Acryloyl chloride. Appl. Rad. Isotp., 58 (2), 209-17.

Bonasera, T. A., Ortu, G., Rozen, Y., Krais, R., Freedman, N. M., Chisin, R., Gazit, A., Levitzki, A.; and Mishani, E. (2001). Potential (18)F-labeled biomarkers for epidermal growth factor receptor tyrosine kinase. Nucl. Med. Biol. 28, 359-74.

Chaffee S., Mary A., Stiehm E. R., Girault D., Fischer A., and Hershfield M. S. (1992). IgG antibody response to polyethylene glycol-modified adenosine deaminase in patients with adenosine deaminase deficiency. J Clin. Invest. 89, 1643-51.

Faaland, C. A. Mermelstein, F. H., Hayashi, J., and Laskin, J. D. (1991). Rapid uptake of tyrphostin into A431 human epidermoid cells is followed by delayed inhibition of epidermal growth factor (EGF)-stimulated EGF receptor tyrosine kinase activity. Mol. Cell. Biol. 11, 2697-703.

Fry, D. W., Bridges, A. J., Denny, W. A., Doherty, A., Greis, K. D. Hicks, J. L., Hook, K. E., Keller, P. R., Leopold, W. R., Loo, J. A., McNamara, D. J., Nelson, J. M., Sherwood, V., Smaill, J. B., Trumpp-Kallmeyer, S., and Dobrusin, E. M. (1998). Specific, irreversible inactivation of the epidermal growth factor receptor and erbB2, by new class of tyrosine kinase inhibitor. Proc. Natl. Acad. Sci. USA 95, 12022-7.

Fry, D. W., Kraker, A. J., McMichael, A., Ambroso, L. A., Nelson, J. M., Leopold, W. R., Connors, R. W., and Bridges, A. J. (1994). A specific inhibitor of the epidermal growth factor receptor tyrosine kinase. Science 265, 1093-95.

Gazit, A., Chen, J., App, H., McMahon, G., Hirth, P., Chen, I., and Levitzki, A. (1996). Tyrphostins IV-highly potent inhibitors of EGF receptor kinase. B. Structure-activity relationship study of 4-anilidoquinazolines. Bioorg. Med. Chem. 4, 1203-7.

Han, Y., Caddy, C. G., Nanda, A., Cavenee, W. K., and Huang, H. J. (1996). Tyrphostin AG 1478 preferentially inhibits human glioma cells expressing truncated rather than wild-type epidermal growth factor receptors. Cancer. Res. 56, 3859-61.

James, M., Lippman, R., and Lippman, M. (2004). Breast cancer. Research and Treatment. 83, 99-107.

Johnstrom P., Fredriksson A., Thorell J. O., and Stone-Elander S. J. (1998). Labelled Cpd. Radiopharm. 41, 623.

Johnstrom, P., Fredriksson, A., Thorell, J. O., Hassan, M., Kogner, P., Borgstrom, P., Ingvar, M., and Stone-Elander, S. (1997). Synthesis and in vivo biodistribution of tyrosine kinase inhibitor, [mehoxy-$^{11}$C]PD 153035. J. Label. Compds. Radiopharm. 40, 377-79.

Le Chevalier, T. and Lynch, T. (2004). Adjuvant treatment of lung cancer: current status and potential applications of new regimens. Lung Cancer Suppl 2, S33-9.

Lehel, S. Z., Horváth, G., Boros, I., Márián, T., and Trón, L. (2002). The nucleophilic reaction for [$^{18}$F]fluoride-ion on the series of N$^6$-benzoyl-2',3'-isopropylideneadenosine-5'-sulfonates. J. Radioanal. Nucl. Chem. 251, 413-16.

Levitzki, A. (2003). EGF receptor as a therapeutic target. Lung Cancer 41 Suppl 1, S9-14.

Levitzki, A., and Gazit, A. (1995). Science 267, 1782-88.

MacMahon, S., Fong, R., Bran, P. S., Safonov, I., Wilson, S. R., and Schuster, D. I. (2001). J. Org. Chem. 66 5449-55.

Mishani, E., Abourbeh, G., Jacobson, O., Dissoki, S., Ben-Daniel, R., and Levitzki, A. (2005). High affinity EGFR irreversible inhibitors with diminished chemical reactivities as PET imaging agent candidates of EGFR irreversible overexpressing tumors. J. Med. Chem. 48, 5337-48.

Mishani, E., Bonasera, T. A., Rozen, Y., Ortu, G., Gazit, A., and Levitzki, A. (1999). Fluorinated EGFR-TK inhibitors based tracers for PET. J. Labelled. Compd. Radiopharm. 42, suppl. 1, S27-S29.

Mishani. E.; Abourbeh. G.; Rozen. Y.; Jacobson. O.; Laky. D.; Ben David. I.; Levitzki. A.; Saul. M. (2004) Novel carbon-11 labeled 4-dimethylamino-but-2-enoicacid[4-(phenylamino)-quinazoline-6-yl]-amides: potential PET bioprobes for molecular imaging of EGFR-positive tumors. Nucl. Med. Biol. 31: 469-476.

Mishani E., Ben-david I., Rozen Y., Laki d., Bocher M. and Chisin R. (2001) *J. Labl. Comp. Radiopharm.* 44, 379.

Miyaji, K., Tani, E. Shinado, H., Nakano, A. and Todunaga, T. (1994). Effect of tyrphostin on cell growth and tyrosine kinase activity of epidermal growth factor receptor in human gliomas. J. Neurosurg. 81, 411-9.

Nelson, J. M., and Fry, D. W. (1997). Cytoskeletal and morphological changes associated with the specific suppression of the epidermal growth factor receptor tyrosine kinase activity in A431 human epidermoid carcinoma. Exp. Cell. Res. 233, 383-90.

Mulholland, G. K., Zheng, Q-H., Winkle, W. L., and Carlson, K. A. (1997). Synthesis and biodistribution of new C-11 and F-18 labeled epidermal growth factor receptor ligands. J. Nucl. Med. 38, Suppl., 141P.

Mulholland, G. K., Winkle, W., Mock, B. H., and Sledge, G. (1995). Radioiodinated epidermal growth factor receptor ligands as tumor probes. Dramatic potentiation of binding to MDA-468 cancer cells in presence of EGF. J. Nucl. Med. 36, Suppl, 71P.

Paez, J. G., Janne, P. A., Lee, J. C., Tracy, S., Greulich, H., Gabriel, S., Herman, P., Kaye, F. J., Lindeman, N., Boggon, T. J., Naoki, K., Sasaki, H., Fujii, Y., Eck, M. J., Sellers, W. R., Johnson, B. E., and Meyerson, M. (2004). EGFR mutations in lung cancer: correlation with clinical response to gefitinib therapy. Science 4, 304, 1497-500.

Pyatak P. S., Abuchowski A., and Davis F. F. (1980) Preparation of a Polyethylene Glycol: Superoxide Dismutase Adduct, and an Examination of its Blood Circulating Life and Anti-Inflammatory Activity", Res. Commun. Chem. Pathol. Pharmacol., vol. 29, No. 1, pp. 113-127.

Rae. J. M. and Lippman. M. E. (2004) Breast cancer. Research and Treatment 83, 99-107.

Shimada, Y., and Imamura, M. (1996). Prognostic factors for esophageal cancer-from the view point of molecular biology. Gan. To Kagaku Ryoho. 23, 972-81.

Smaill, J. B., Rewcastle, G. W., Loo, J. A., Greis, K. D., Chan, O. H., Reyner, E. L., Lipka, E., Showalter, H. D. H., Vincent, P. W., Elliott, W. L., and Denny, W. A. (2000). Tyrosine kinase inhibitors. 17. Irreversible inhibitors of the epidermal growth factor receptor: 4-(Phenylamino)quinazoline- and 4-(phenylamino)pyrido[3,2-d]pyrimidine-6-acrylamides bearing additional solubilizing functions. J. Med. Chem. 43, 1380-1397.

Smaill, J. B., Palmer, B. D., Rewcastle, G. W., Denny, W. A., McNamara, D. J., Dobrusin, E. M., Bridges, A. J., Zhou, H., Showalter, H. D., Winters, R. T., Leopold, W. R., Fry, D. W., Nelson, J. M., Slintak, V., Elliot, W. L., Roberts, B. J., Vincent, P. W., and Patmore, S. J. (1999). Tyrosine kinase inhibitors. 15. 4-(Phenylamino)quinazoline and 4-(phenylamino)pyrido[d]pyrimidine acrylamides as irreversible inhibitors of the ATP binding site of the epidermal growth factor receptor. J. Med. Chem. 42, 1803-15.

Takano, T., Ohe, Y., Sakamoto, H., Tsuta, K., Matsuno, Y., Tateishi, U., Yamamoto, S., Nokihara, H., Yamamoto, N., Sekine, I., Kunitoh, H., Shibata, T., Sakiyama, T., Yoshida, T., and Tamura, T. (2005). Epidermal growth factor receptor gene mutations and increased copy numbers predict gefitinib sensitivity in patients with recurrent non-small-cell lung cancer. J. Clin. Oncol. 23, 6829-37.

Tokunaga, A., Onda, M., Okuda, T., Fujita, I., Mizutani, T., Kiyana, T., Yoshiynki, T., Nishi, K., and Matsukura, N. (1995). Clinical significance of epidermal growth factor (EGF), EGF receptor, and c-erbB-2 in human gastric cancer. Cancer 75,1418-25.

Tsou, H-R., Mamuya, N., Johnson, B. D. Reich, M. F., Gruber, B. C., Ye, F., Nilakantan, R., Shen, R., Discafani, C., DeBlance, R., Davis, R., Koehn, F. E., Greenberger, L. M., Wang, Y-F., and Wissner, A. (2001). 6-substituted-4-(3-bromophenylamino)quinazolines as putative irreversible inhibitors of the epidermal growth factor receptor (EGFR) and human epidermal growth factor receptor (HER-2) tyrosine kinases with enhanced antitumor activity. J. Med. Chem. 44, 2719-2734.

What is claimed is:

1. A radiolabeled compound having the general Formula I*:

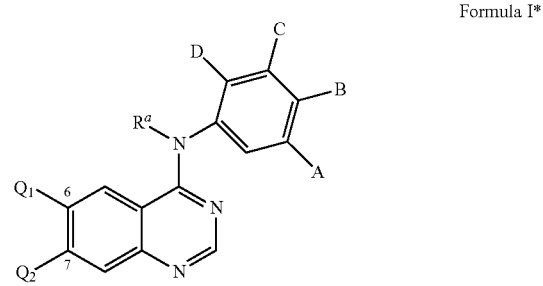

Formula I* and comprising a radiolabeled polyalkylene glycol or a non-radiolabeled polyalkylene glycol moiety being covalently attached at position 7 of the compound having said Formula I, wherein:

Q1 is X—W(=Y)—Z and Q2 is absent,

X is —NR$^1$;

W is selected from the group consisting of a non-radioactive carbon and a radioactive carbon;

Y is selected from the group consisting of oxygen and sulfur;

Z is selected from the group consisting of —$R^2C$=$CHR^3$ and —$CR^4R^5R^6$;

$R^a$ is selected from the group consisting of hydrogen or alkyl having 1-8 carbon atoms;

A, B, C and D are each independently selected from the group consisting of hydrogen, a first non-radioactive derivatizing group and a first radioactive derivatizing group selected from a radioactive bromine, a radioactive iodine and a radioactive fluorine;

$R^1$ is selected from the group consisting of hydrogen, and substituted or nonsubstituted alkyl having 1-6 carbon atoms;

$R^2$ is selected from the group consisting of hydrogen, halogen and alkyl having 1-6 carbon atoms;

$R^3$ is selected from the group consisting of hydrogen, halogen, carboxy, alkenyl, alkoxy, carbonyl, substituted or non-substituted alkyl having 1-6 carbon atoms, substituted or non-substituted phenyl and substituted or non-substituted alkyl having 1-6 carbon atoms at least one being a radioactive carbon;

$R^4$ is a leaving group; and $R^5$ and $R^6$ are each independently selected from the group consisting of hydrogen and a second derivatizing group, and wherein said polyalkylene glycol moiety has a general Formula II*:

$$-[U(CR'R'')m]nV \qquad \text{Formula II*}$$

wherein:

m is an integer from 1 to 6;

n is an integer from 2 to 10;

U is O, S or NR''';

V is selected from the group consisting of a radioactive third derivatizing group and a non-radioactive third derivatizing group selected from the group consisting of a radioactive atom, hydroxyl, thiol, amine, alkyl, cycloalkyl, halogen, haloalkyl, alkoxy, thioalkoxy, thiophenyl, alkenyl, alkynyl, amide, carboxylate, thiocarboxylate, sulfinyl, sulfonyl, carbamyl, thiocarbamyl, nitro and cyano; and R', R'' and R''' are each independently selected from the group consisting of hydrogen, alkyl, and cycloalkyl, the compound comprising at least one radioactive atom.

2. The radiolabeled compound of claim 1, wherein V is a non-radioactive derivatizing group selected from the group consisting of hydroxy and halogen.

3. The radiolabeled compound of claim 1, wherein said leaving group is selected from the group consisting of alkoxy and halogen.

4. The radiolabeled compound of claim 1, wherein Y is oxygen.

5. The radiolabeled compound of claim 1, wherein W is said radioactive carbon.

6. The radiolabeled compound of claim 1, wherein at least one of A, B, C and D is said first radioactive derivatizing group.

7. The radiolabeled compound of claim 1, wherein said at least one radioactive atom forms a part of said polyalkylene glycol moiety.

8. The radiolabeled compound of claim 7, wherein V in said Formula II* is said radioactive third derivatizing group.

9. The radiolabeled compound of claim 7, wherein said radioactive third derivatizing group comprises at least one radioactive atom selected from the group consisting of a radioactive carbon, a radioactive fluorine, a radioactive bromine and a radioactive iodine.

10. The radiolabeled compound of claim 9, wherein V is a radioactive fluorine.

11. The radiolabeled compound of claim 1, wherein Z is —$CR^4R^5R^6$.

12. The radiolabeled compound of claim 1, wherein Z is $R^2C$=$CHR^3$.

13. The radiolabeled compound of claim 12, wherein said $R^3$ is a substituted alkyl having 1-6 carbon atoms.

14. The radiolabeled compound of claim 13, wherein said substituted alkyl comprises a radioactive atom.

15. The radiolabeled compound of claim 13, wherein said substituted alkyl comprises a substituted amino group.

16. The radiolabeled compound of claim 15, wherein said substituted amino group comprises a radioactive atom.

17. The radiolabeled compound of claim 15, wherein said substituted amino group comprises a hydroxyalkyl group.

18. The radiolabeled compound of claim 1, further comprising at least one hydroxy-containing moiety being covalently attached thereto.

19. The radiolabeled compound of claim 18, wherein said hydroxy-containing moiety is selected from the group consisting of group hydroxy, a hydroxyalkyl and an additional polyalkylene glycol moiety.

20. A pharmaceutical composition comprising the radiolabeled compound of claim 1 and a pharmaceutically acceptable carrier.

21. A method of monitoring the level of epidermal growth factor receptor within a body of a patient, the method comprising:
(a) administering to the patient the radiolabeled compound of claim 1; and
(b) employing a nuclear imaging technique for monitoring a distribution of the compound within the body or within a portion thereof.

22. A method of radiotherapy comprising administering to a patient a therapeutically effective amount of the pharmaceutical composition of claim 20.

23. A method of inhibiting cell proliferation, the method comprising subjecting the cell to the radiolabeled compound of claim 1.

24. A method of synthesizing a radiolabeled compound having the general Formula V:

Formula V wherein:

X is —$NR^1$

W is carbon;

Y is selected from the group consisting of oxygen and sulfur;

Z is selected from the group consisting of —$R^2C$=$CHR^3$ and —$CR^4R^5R^6$;

$R^a$ is selected from the group consisting of hydrogen or alkyl having 1-8 carbon atoms;

A, B, C and D are each independently selected from the group consisting of hydrogen, a fluorine-18 and a first derivatizing group, provided that at least one of A, B, C and D is said fluorine-18;

$R^1$ is selected from the group consisting of hydrogen, and substituted or non-substituted alkyl having 1-6 carbon atoms;

$R^2$ is selected from the group consisting of hydrogen, halogen and alkyl having 1-6 carbon atoms;

$R^3$ is selected from the group consisting of hydrogen, halogen, carboxy, alkenyl, alkoxy, carbonyl, substituted or non-substituted alkyl having 1-6 carbon atoms and substituted or non-substituted phenyl;

$R^4$ is a leaving group;

$R^5$ and $R^6$ are each independently selected from the group consisting of hydrogen and a second derivatizing group;

m is an integer from 1 to 6;

n is an integer from 2 to 10;

U is O, S or NR''';

V is a third derivatizing group selected from the group consisting of a radioactive group, hydroxyl, thiol, amine, alkyl, cycloalkyl, halogen, haloalkyl, alkoxy, thioalkoxy, aryloxy, thioaryloxy, alkenyl, alkynyl, amide, carboxylate, thiocarboxylate, sulfinyl, sulfonyl, carbamyl, thiocarbamyl, nitro and cyano; and R', R'' and R''' are each independently selected from the group consisting of hydrogen, alkyl, and cycloalkyl, the method comprising:

coupling a fluorine-18 labeled 4-anilinoquinazoline derivatized by said $R^a$, A, B, C and D and substituted at the quinazoline ring by a first and a second reactive groups, with a polyalkylene glycol derivatized by said R', R'', R''' and V and substituted by a third reactive group capable of reacting with said second reactive group, to thereby produce a fluorine-18 labeled 4-anilinoquinazoline substituted by said first reactive group and further substituted by said polyalkylene glycol moiety;

and reacting said fluorine-18 labeled 4-anilinoquinazoline substituted by said first reactive group and by said polyalkylene glycol moiety with a reactive carboxylic derivative that comprises said Z at the α position, thereby producing the compound having the general Formula V.

25. The radiolabeled compound of claim 1, further comprising at least one radiolabeled or a non-radiolabeled hydroxy-containing moiety being covalently attached thereto, the compound comprising at least one radioactive atom.

26. The radiolabeled compound of claim 25, wherein said leaving group is selected from the group consisting of alkoxy and halogen.

27. The radiolabeled compound of claim 25, wherein Y is oxygen.

28. The radiolabeled compound of claim 25, wherein Z is —$CR^4R^5R^6$.

29. The radiolabeled compound of claim 25, wherein Z is —$R^2C$=$CHR^3$.

30. The radiolabeled compound of claim 29, wherein said $R^3$ is a substituted alkyl having 1-6 carbon atoms.

31. The radiolabeled compound of claim 30, wherein said substituted alkyl comprises a substituted amino group.

32. The radiolabeled compound of claim 31, wherein said substituted amino group comprises a hydroxyalkyl group.

33. The radiolabeled compound of claim 25, wherein said hydroxy-containing moiety is selected from the group consisting of group hydroxy, a hydroxyalkyl and an additional polyalkylene glycol moiety.

34. A pharmaceutical composition comprising the radiolabeled compound of claim 25 and a pharmaceutically acceptable carrier.

35. A method of monitoring the level of epidermal growth factor receptor within a body of a patient, the method comprising:

(a) administering to the patient the radiolabeled compound of claim 25; and (b) employing a nuclear imaging technique for monitoring a distribution of the compound within the body or within a portion thereof.

36. A method of radiotherapy comprising administering to a patient a therapeutically effective amount of the pharmaceutical composition of claim 34.

37. A method of inhibiting cell proliferation, the method comprising subjecting the cell to the radiolabeled compound of claim 25.

* * * * *